(12) United States Patent
Benfatti et al.

(10) Patent No.: US 10,336,691 B2
(45) Date of Patent: Jul. 2, 2019

(54) PESTICIDALLY ACTIVE OXIME AND HYDRAZONE DERIVATIVES

(71) Applicant: Syngenta Participations AG, Basel (CH)

(72) Inventors: Fides Benfatti, Stein (CH); Andre Jeanguenat, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/579,422

(22) PCT Filed: Jun. 1, 2016

(86) PCT No.: PCT/EP2016/062335
§ 371 (c)(1),
(2) Date: Dec. 4, 2017

(87) PCT Pub. No.: WO2016/193284
PCT Pub. Date: Dec. 8, 2016

(65) Prior Publication Data
US 2018/0141898 A1    May 24, 2018

(30) Foreign Application Priority Data

Jun. 5, 2015  (EP) .................... 15170862

(51) Int. Cl.
| | | |
|---|---|---|
| *C07C 271/60* | (2006.01) | |
| *C07C 281/14* | (2006.01) | |
| *C07C 337/08* | (2006.01) | |
| *A01N 47/24* | (2006.01) | |
| *A01N 47/34* | (2006.01) | |

(52) U.S. Cl.
CPC .......... *C07C 281/14* (2013.01); *A01N 47/24* (2013.01); *A01N 47/34* (2013.01); *C07C 271/60* (2013.01); *C07C 337/08* (2013.01); *C07C 2602/08* (2017.05)

(58) Field of Classification Search
CPC .... A01N 47/24; A01N 47/34; C07C 2602/08; C07C 271/60; C07C 281/14; C07C 337/08
See application file for complete search history.

(56) References Cited

FOREIGN PATENT DOCUMENTS

WO    2011/017504 A1    2/2011

OTHER PUBLICATIONS

Nagata et. al., Pest Management Science, 2003, Society of Chemical Industry, vol. 60, pp. 399-407 (Year: 2003).*
ISR & Written Opinion for PCT/EP2016/062335, dated Aug. 2, 2016.

* cited by examiner

*Primary Examiner* — Sarah Pihonak
(74) *Attorney, Agent, or Firm* — Toni-Junell Herbert; BakerHostetler

(57) ABSTRACT

The present invention relates to compounds of formula (I) as defined herein, to processes for preparing them, to pesticidal, in particular insecticidal, acaricidal, molluscicidal and nematicidal compositions comprising them and to methods of using them to combat and control pests such as insect, acarine, mollusc and nematode pests.

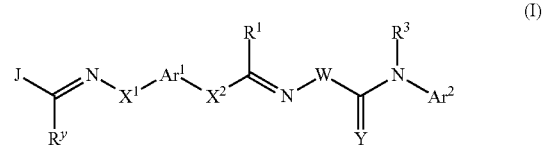

11 Claims, No Drawings

PESTICIDALLY ACTIVE OXIME AND HYDRAZONE DERIVATIVES

RELATED APPLICATION INFORMATION

This application is a 371 of International Application No. PCT/EP2016/062335, filed 01 Jun. 2016, which claims priority to EP patent application No. 15170862.5, filed 05 Jun. 2015, the contents of which are incorporated herein by reference herein.

The present invention relates to compounds of formula (I), to processes for preparing them, to pesticidal, in particular insecticidal, acaricidal, molluscicidal and nematicidal compositions comprising them and to methods of using them to combat and control pests such as insect, acarine, mollusc and nematode pests.

Heterocyclic compounds with pesticidal activity are known and described, for example, in WO09/102736, WO11/017505, WO12/109125, WO13/116052, WO13/116053 and WO14/011429. There have now been found novel pesticidal active oximes and hydrazones.

Accordingly, embodiment 1 is a compound of formula (I),

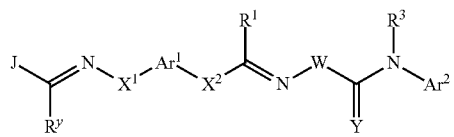

wherein, $Ar^1$ and $Ar^2$ are independently selected from phenyl, thienyl, pyridyl, pyrimidinyl, pyrazinyl, pyridazinyl, furanyl, pyrazolyl, thiazolyl, imidazolyl, oxazolyl and isoxazolyl, wherein said phenyl, thienyl, pyridyl, pyrimidinyl, pyrazinyl, pyridazinyl, furanyl, pyrazolyl, thiazolyl, imidazolyl, oxazolyl and isoxazolyl are unsubstituted or substituted by one to three substituents independently selected from $C_1$-$C_6$alkyl, $C_2$-$C_6$alkenyl, $C_2$-$C_6$alkynyl, $C_{3\text{-}8}$cycloalkyl$C_{0\text{-}6}$alkyl, $C_1$-$C_6$haloalkyl, $C_2$-$C_6$haloalkenyl, $C_2$-$C_6$haloalkynyl, $C_{3\text{-}8}$halocycloalkyl$C_{0\text{-}6}$alkyl, $C_1$-$C_3$haloalkyl-$C_3$-$C_6$cycloalkyl, heterocyclyl$C_{0\text{-}6}$alkyl, halogen, cyano, cyano-$C_1$-$C_4$alkyl, cyano-$C_3$-$C_6$cycloalkyl, nitro, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, —S—$C_1$-$C_6$haloalkyl, —S(O)—$C_1$-$C_6$haloalkyl, —S(=O)$_2$ $C_1$-$C_6$haloalkyl, —S(=O)(=NH)$C_1$-$C_6$haloalkyl, $C_1$-$C_6$alkylamino, $C_2$-$C_6$dialkylamino, $C_3$-$C_6$cycloalkylamino, $C_1$-$C_6$alkyl-$C_3$-$C_6$cycloalkylamino, $C_2$-$C_6$alkylcarbonyl, CHO, $C_2$-$C_6$alkoxycarbonyl, $C_2$-$C_6$haloalkoxycarbonyl, $C_1$-$C_6$alkylaminocarbonyl, $C_1$-$C_6$haloalkylaminocarbonyl or $C_1$-$C_4$ dialkylaminocarbonyl;

$X^1$ is O or $NR^6$;
$X^2$ is a bond or $(CR^4R^5)_n$;
n is 1 or 2;
W is O or $NR^2$
Y is oxygen or sulfur;
$R^1$ and $R^y$ are independently hydrogen, $C_1$-$C_6$-alkyl, halo-$C_1$-$C_6$-alkyl, $C_3$-$C_6$-cycloalkyl or $C_1$-$C_3$-alkoxy; $R^6$, $R^2$ and $R^3$ are independently selected from hydrogen, $C_1$-$C_6$alkyl, $C_1$-$C_6$-haloalkyl, $C_3$-$C_6$-cycloalkyl$C_{0\text{-}6}$alkyl, $C_{3\text{-}8}$halocycloalkyl$C_{0\text{-}6}$alkyl, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, —S(O)—$C_1$-$C_6$alkyl, —S(=O)$_2$ $C_1$-$C_6$alkyl, —S(O)—$C_1$-$C_6$haloalkyl, —S(=O)$_2$ $C_1$-$C_6$haloalkyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy and —C(=N—$C_1$-$C_4$alkoxy)-$C_1$-$C_4$alkyl; provided that when $R_2$ and $R_3$ are different from hydrogen, $R_2$ and $R_3$ is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, halogen, cyano, nitro, $C_1$-$C_6$alkoxy, $C_1$-$C_6$haloalkoxy, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl and $C_2$-$C_8$ dialkylaminocarbonyl;

$R^4$ and $R^5$ are independently selected from hydrogen, $C_1$-$C_6$-alkyl, $C_1$-$C_6$-haloalkyl, $C_3$-$C_6$-cycloalkyl and $C_1$-$C_6$-alkoxy;

J is phenyl or heteroaryl;

or J and $R^y$ together with carbon atom to which they are attached form a 9 to 11 membered fused bicyclic ring system; wherein said phenyl, heteroaryl or 9 to 11 membered fused bicyclic ring system is unsubstituted or substituted with one to three substituents independently selected from $C_1$-$C_6$alkyl, $C_2$-$C_6$alkenyl, $C_2$-$C_6$alkynyl, $C_{3\text{-}8}$cycloalkyl$C_{0\text{-}6}$alkyl, $C_1$-$C_6$haloalkyl, $C_2$-$C_6$haloalkenyl, $C_2$-$C_6$haloalkynyl, $C_{3\text{-}8}$halocycloalkyl$C_{0\text{-}6}$alkyl, $C_1$-$C_3$haloalkyl-$C_3$-$C_6$cycloalkyl, heterocyclyl$C_{0\text{-}6}$alkyl, halogen, cyano, cyano-$C_1$-$C_4$alkyl, cyano-$C_3$-$C_6$cycloalkyl, nitro, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, $C_1$-$C_6$alkylamino, $C_2$-$C_6$dialkylamino, $C_3$-$C_6$cycloalkylamino, $C_1$-$C_6$alkyl-$C_3$-$C_6$cycloalkylamino, $C_1$-$C_6$alkylcarbonyl, CHO, $C_1$-$C_6$alkoxycarbonyl, $C_1$-$C_6$haloalkoxycarbonyl, $C_1$-$C_6$alkylaminocarbonyl, $C_1$-$C_6$haloalkylaminocarbonyl and $C_1$-$C_4$ dialkylaminocarbonyl;

or an agrochemically acceptable salt, stereoisomer, tautomer, N-oxide thereof.

Definitions

The term 'halogen' as used herein refers to a fluoro, chloro, bromo or iodo.

As used herein, the term "$C_{2\text{-}6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1\text{-}4}$alkyl" is to be construed accordingly. Examples of $C_{1\text{-}6}$alkyl include, but are not limited to, methyl, (R)-methyl, ethyl, n-propyl, 1-methylethyl (iso-propyl), n-butyl, n-pentyl and 1,1-dimethylethyl (t-butyl).

As used herein, the term "$C_{2\text{-}6}$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "$C_{2\text{-}4}$alkenyl" is to be construed accordingly. Examples of $C_{2\text{-}6}$alkenyl include, but are not limited to, ethenyl, prop-1-enyl, but-1-enyl, pent-1-enyl, pent-4-enyl and penta-1,4-dienyl.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "C2-4alkynyl" is to be construed accordingly. Examples of C2-6alkynyl include, but are not limited to, ethynyl, prop-1-ynyl, but-1-ynyl, pent-1-ynyl, pent-4-ynyl and penta-1,4-diynyl.

As used herein, the term "$C_{1-6}$haloalkyl" refers to $C_{1-6}$alkyl radical, as defined above, substituted with one or more of the same or different halogen atoms, as defined above. Examples of halogen$C_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term '$C_{2-6}$haloalkenyl' as used herein refers to a $C_{2-6}$ alkenyl radical, as defined herein, substituted with one or more of the same or different halogen atoms, e.g for example, 2,2-difluorovinyl or 1,2-dichloro-2-fluoro-vinyl.

As used herein, the term '$C_{2-6}$haloalkynyl' as used herein refers to a $C_{2-6}$ alkynyl radical, as defined herein, substituted with one or more of the same or different halogen atoms, for example 1-chlor-prop2-ynyl.

As used herein, the term "$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, isopropoxy, butoxy, isobutoxy, pentoxy, and hexoxy.

As used herein, the term "$C_{1-6}$haloalkoxy" refers to $C_{1-6}$alkoxy radical, as defined above, substituted by one or more halo radicals, as defined above. Examples of halogen$C_{1-6}$alkoxy include, but are not limited to, trifluoromethoxy, difluoromethoxy, fluoromethoxy, trichloromethoxy, 2,2,2-trifluoroethoxy, 1,3-dibromopropan-2-yloxy, 3-bromo-2-fluoropropyloxy and 1,4,4-trifluorobutan-2-yloxy.

As used herein, the term "$C_{1-6}$alkylcarbonyl" refers to a radical of the formula —C(=O)—$R_a$ where $R_a$ is a $C_{1-6}$alkyl radical as defined above.

As used herein, the term "$C_{1-6}$alkylcarbonyl$C_{1-6}$alkyl" refers to a radical of the formula —$R_a$—C(=O)—$R_a$ where each $R_a$ is independently a $C_{1-6}$alkyl radical as defined above. The carbon atom of the carbonyl group may be bonded to any carbon atom in either alkyl radical.

As used herein, the term "$C_{1-6}$alkoxycarbonyl" refers to a radical of the formula —C(=O)—O—$R_a$ where $R_a$ is a $C_{1-6}$alkyl radical as defined above.

As used herein, the term "$C_{1-6}$alkoxycarbonyl$C_{1-6}$alkyl" refers to a radical of the formula —$R_a$—C(=O)—O—$R_a$ where each $R_a$ is independently a $C_{1-6}$alkyl radical as defined above.

As used herein, the term "$C_{1-6}$alkylamino" refers to a radical of the formula —NH—$R_a$ where $R_a$ is a $C_{1-6}$alkyl radical as defined above.

As used herein, the term "$C_{1-6}$dialkylamino" refers to a radical of the formula —N($R_a$)—$R_a$ where each $R_a$ is a $C_{1-6}$alkyl radical, which may be the same or different, as defined above.

As used herein, the term "$C_{3-8}$cycloalkyl$C_{0-6}$alkyl" refers to a stable non-aromatic monocyclic hydrocarbon radical consisting solely of carbon and hydrogen atoms, having from three to eight carbon atoms, and which is saturated or unsaturated and attached to the rest of the molecule by a single bond or by a $C_{1-6}$alkyl radical as defined above. Examples of $C_{3-8}$cycloalkyl$C_{0-6}$alkyl include, but are not limited to, cyclopropyl, cyclopropyl-methyl, cyclobutyl, cyclobutyl-ethyl, cyclopentyl, cyclopentyl-propyl, cyclohexyl, cycloheptyl and cyclooctyl.

As used herein, the term "$C_{3-8}$halocycloalkyl$C_{0-6}$alkyl" as used herein refers to a $C_{3-8}$cycloalkyl$C_{0-6}$alkyl radical as defined herein substituted with one or more of the same or different halogen atoms.

As used herein, the term "heterocyclyl" or "heterocyclic" refers to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

As used herein, the term "heterocyclyl$C_{0-6}$alkyl" refers to a heterocyclic ring as defined above which is attached to the rest of the molecule by a single bond or by a $C_{1-6}$alkyl radical as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

The term "9 to 11 membered fused bicyclic ring system" includes but is not limited to the following ring systems indolinyl, indanyl, indolyl, isoindolinyl, isoindolyl, indenyl, benzofuranyl, benzothiophenyl, indazolyl, benzimidazolyl, benzothiazolyl, benzoxazolyl, benzoxazinyl, benzopyranyl, benzothiopyranyl, quinolinyl, isoquinolinyl, chromenyl, cinnolinyl, phthalazinyl, quinazolinyl, quinoxalinyl, naphthyridinyl, furopyridinyl, naphthyl, dihydrobenzoxazinyl, dihydrochromenyl, dihydrobenzodioxinyl, tetrahydroquinolinyl, tetrahydroquinoxalinyl, tetrahydronaphthalenyl dihydrobenzofuranyl, dihydrobenzopyranyl, dihydrobenzothiopyranyl, dihydrobenzothiophenyl, dihydrodioxinopyridinyl, dihydroindenyl, dihydropyrrolopyridinyl, dihydropyrrolopyrimidinyl, dihydropyrrolopyrazinyl, dihydropyrrolopyridazinyl, pyrrolopyridinyl, pyrrolopyrazinyl, pyrrolopyridazinyl, pyrrolopyrimidinyl, furopyrimidinyl, furopyrazinyl, furopyridazinyl, thienopyridinyl, thienopyrazinyl, thienopyridazinyl, thienopyrimidinyl, pyrazolopyridinyl, pyrazolopyrazinyl, pyrazolopyridazinyl, pyrazolopyrimidinyl, imidazopyridinyl, imidazopyrazinyl, imidazopyridazinyl, imidazopyrimidinyl, thiazolopyridinyl, thiazolopyrazinyl, thiazolopyridazinyl, thiazolopyrimidinyl, oxazolopyridinyl, oxazolopyrazinyl, oxazolopyridazinyl, oxazolopyrimidinyl, pyridopyrazinyl, pyridopyridazinyl, pyridopyrimidinyl, pyridooxazinyl, pyrazinooxazinyl, pyridazinooxazinyl, pyrimidooxazinyl, dihydropyridooxazinyl, dihydropyrazinooxazinyl, dihydropyridazinooxazinyl, dihydropyrimidooxazinyl, dihydropyranopyridinyl, dihydropyranopyrazinyl, dihydropyranopyridazinyl, dihydropyrimidinyl, pyranopyridinyl, pyranopyrimidinyl, pyranopyrazinyl, pyranopyridazinyl, dihydrodioxinopyridinyl, dihydrodioxinopyrazinyl, dihydrodioxinopyridazinyl, dihydrodioxinopyrimidinyl, tetrahydronaphthyridinyl, tetrahydropyridopyridazinyl, tetrahydropyridopyrazinyl, tetrahydropyridopyrimidinyl, tetrahydropyrazinopyridazinyl, tetrahydropteridinyl, tetrahydropyrazinopyrazinyl, tetrahydroquinolinyl, tetrahydrocinnolinyl, tetrahydroquinazolinyl, tetrahydroquinoxalinyl, thiinopyridinyl, thiinopyrazinyl, thiinopyridazinyl, thiinopyrimidinyl, dihydrothiinopyridinyl, dihydrothiinopyrazinyl, dihydrothiinopyridazinyl, dihydrothiinopyrimidinyl, dihydrofuropyridinyl, dihydrofuropyrazinyl, dihydrofuropyridazinyl, dihydrofuropyrimidinyl, dihydrothienopyridinyl, dihydrothienopyrazinyl, dihydrothienopyridazinyl, dihydrothienopyrimidinyl, dihydrocyclopentapyridinyl, dihydrocyclopentapyrazinyl, dihydrocyclopentapyridazinyl, dihydrocyclopentapyrimidinyl, quinolinonyl, naphtyridinonyl, pyridopyrazinonyl, pyridopyridazinonyl and pyridopyrimidinonyl.

As used herein, when one embodiment refers to several other embodiments by using the term "according to any one of", for example "according to any one of embodiments 1 to 22", then said embodiment refers not only to embodiments indicated by the integers such as 1 and 2 but also to embodiments indicated by numbers with a decimal component such as 22.1.

Cyano means a —CN group. Amino means an —$NH_2$ group. Hydroxyl or hydroxy stands for an —OH group.

The presence of one or more C=N double bonds in a compound of formula (I) means that the compounds may occur in E or Z isomeric forms. Formula (I) is intended to include all those possible stereoisomeric forms and mixtures thereof.

The presence of one or more possible asymmetric carbon atoms in a compound of formula (I) means that the compounds may occur in optically stereoisomeric forms, i.e. enantiomeric or diastereomeric forms. Also atropisomers may occur as a result of restricted rotation about a single bond. Formula (I) is intended to include all those possible stereoisomeric forms and mixtures thereof. The present invention includes all those possible stereoisomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide or in salt form, e.g. an agronomically usable salt form.

Embodiment 2: A compound according to embodiment 1, wherein $Ar^1$ and $Ar^2$ are independently of each other phenyl, thienyl, pyridyl, pyrimidinyl, pyrazinyl, pyridazinyl, furanyl, wherein said phenyl, thienyl, pyridyl, pyrimidinyl, pyrazinyl, pyridazinyl, furanyl is unsubstituted or substituted by one to three substituents independently selected from $C_1$-$C_6$alkyl, $C_2$-$C_6$alkenyl, $C_2$-$C_6$alkynyl, $C_{3-8}$cycloalkyl$C_{0-6}$alkyl, $C_1$-$C_6$haloalkyl, $C_2$-$C_6$haloalkenyl, $C_2$-$C_6$haloalkynyl, $C_{3-8}$halocycloalkyl$C_{0-6}$alkyl, $C_1$-$C_3$haloalkyl-$C_3$-$C_6$cycloalkyl, heterocyclyl$C_{0-6}$alkyl, halogen, cyano, cyano-$C_1$-$C_4$alkyl, cyano-$C_3$-$C_6$cycloalkyl, nitro, $C_1$-$C_6$alkoxy, $C_1$-$C_4$haloalkoxy, $C_1$-$C_4$alkoxy-$C_1$-$C_4$alkyl, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, $C_1$-$C_6$alkylamino, $C_2$-$C_6$dialkylamino, $C_3$-$C_6$cycloalkylamino, $C_1$-$C_6$alkyl-$C_3$-$C_6$cycloalkylamino, $C_1$-$C_6$alkylcarbonyl, CHO, $C_1$-$C_6$alkoxycarbonyl, $C_2$-$C_6$haloalkoxycarbonyl, $C_1$-$C_6$alkylaminocarbonyl, $C_1$-$C_6$haloalkylaminocarbonyl and $C_1$-$C_4$ dialkylaminocarbonyl.

Embodiment 3: A compound according to embodiment 1 or 2, wherein $Ar^1$ is phenyl which is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, heterocyclyl$C_{0-6}$alkyl, halogen, cyano, nitro, $C_1$-$C_6$alkoxy, $C_1$-$C_6$haloalkoxy, —S—$C_1$-$C_6$alkyl, —S(O)—$C_1$-$C_6$alkyl, —S(=O)$_2$ $C_1$-$C_6$alkyl, —S(=O)(=NH)$C_1$-$C_6$alkyl, $C_2$-$C_6$alkylcarbonyl, CHO, $C_2$-$C_6$alkoxycarbonyl and $C_2$-$C_6$haloalkoxycarbonyl.

Embodiment 4: A compound according to any one of embodiments 1 to 3, wherein $Ar^1$ is phenyl which is unsubstituted or substituted by one to three substituents independently selected from $C_1$-$C_6$alkyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_6$alkoxy and $C_1$-$C_6$haloalkoxy.

Embodiment 4.1: A compound according to any one of embodiments 1 to 3, wherein $Ar^1$ is unsubstituted phenyl.

Embodiment 5: A compound according to any one of embodiments 1 to 4, wherein $Ar^2$ is phenyl which is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, $C_1$-$C_6$alkoxy, $C_1$-$C_6$haloalkoxy and —S— $C_1$-$C_6$alkyl.

Embodiment 6: A compound according to any one of embodiments 1 to 5, wherein $Ar^2$ is phenyl which is unsubstituted or substituted by one to three substituents independently selected from $C_1$-$C_4$alkyl, $C_1$-$C_4$haloalkyl, halogen, $C_1$-$C_4$alkoxy and $C_1$-$C_4$haloalkoxy.

Embodiment 7: A compound according to any one of embodiments 1 to 6, wherein $X^1$ is O or $NR^6$; $R^6$ is selected from hydrogen, $C_1$-$C_6$alkyl, $C_1$-$C_6$haloalkyl, $C_3$-$C_6$cycloalkyl, halo-$C_3$-$C_6$cycloalkyl, $C_2$-$C_6$alkenyl, $C_2$-$C_6$haloalkenyl, $C_2$-$C_6$-alkynyl, $C_2$-$C_6$haloalkynyl, $C_1$-$C_6$alkoxy-$C_1$-$C_6$alkyl, —S—$C_1$-$C_6$alkyl, —S(O)—$C_1$-$C_6$alkyl, —S(=O)$_2$ $C_1$-$C_6$alkyl, $C_1$-$C_6$alkylcarbonyl, $C_1$-$C_6$alkoxycarbonyl, $C_1$-$C_6$alkylaminocarbonyl, $C_1$-$C_6$dialkylaminocarbonyl, $C_1$-$C_6$alkoxycarbonyloxy, $C_1$-$C_6$alkylaminocarbonyloxy, $C_1$-$C_6$dialkylaminocarbonyloxy and —C(=N—$C_1$-$C_4$alkoxy)-$C_1$-$C_4$alkyl; preferably $R^6$ is hydrogen or $C_1$-$C_6$alkyl; more preferably $R^6$ is hydrogen or $C_1$-$C_3$alkyl; most preferably $R^6$ is hydrogen or methyl.

Embodiment 8: A compound according to any one of embodiments 1 to 7, wherein $X^2$ is a bond or $(CR^4R^5)_n$; n is 1 or 2; $R^4$ and $R^5$ are independently selected from hydrogen, $C_1$-$C_6$alkyl, halo-$C_1$-$C_6$alkyl, $C_3$-$C_6$cycloalkyl and $C_1$-$C_6$alkoxy; preferably $R^4$ and $R^5$ are independently selected from hydrogen and $C_1$-$C_6$alkyl.

Embodiment 9: A compound according to any one of embodiments 1 to 7, wherein $X^2$ is a bond.

Embodiment 10: A compound according to any one of embodiments 1 to 9, wherein W is O or $NR^2$; $R^2$ is selected from hydrogen, $C_1$-$C_6$alkyl, $C_1$-$C_6$haloalkyl, $C_3$-$C_6$cycloalkyl, halo-$C_3$-$C_6$cycloalkyl, $C_2$-$C_6$alkenyl, $C_2$-$C_6$haloalkenyl, $C_2$-$C_6$-alkynyl, $C_2$-$C_6$haloalkynyl, $C_1$-$C_6$alkoxy-$C_1$-$C_6$alkyl, S—$C_6$-$C_6$alkyl, —S(O)—$C_1$-$C_6$alkyl, —S(=O)$_2$ $C_1$-$C_6$alkyl, $C_1$-$C_6$alkylcarbonyl, $C_1$-$C_6$alkoxycarbonyl, $C_1$-$C_6$alkylaminocarbonyl, $C_1$-$C_6$dialkylaminocarbonyl, $C_1$-$C_6$alkoxycarbonyloxy, $C_1$-$C_6$alkylaminocarbonyloxy, $C_1$-$C_6$dialkylaminocarbonyloxy and —C(=N—$C_1$-$C_4$alkoxy)-$C_1$-$C_4$alkyl, preferably $R^2$ is hydrogen or $C_1$-$C_6$alkyl; more preferably $R^2$ is hydrogen or $C_1$-$C_3$alkyl; most preferably $R^2$ is hydrogen or methyl.

Embodiment 11: A compound according to any one of embodiments 1 to 9, wherein $R^1$ is hydrogen, $C_1$-$C_6$-alkyl, $C_1$-$C_6$haloalkyl, $C_3$-$C_6$-cycloalkyl or $C_1$-$C_6$-alkoxy; preferably, $R^1$ is hydrogen or $C_1$-$C_6$-alkyl; more preferably, $R^1$ is hydrogen or $C_1$-$C_3$-alkyl; most preferably $R^1$ is hydrogen or methyl.

Embodiment 12: A compound according to any one of embodiments 1 to 11, wherein $R^y$ is hydrogen, $C_1$-$C_6$-alkyl, halo-$C_1$-$C_6$-alkyl, $C_3$-$C_6$-cycloalkyl, $C_1$-$C_3$-alkoxy; preferably, $R^y$ is $C_1$-$C_6$-alkyl; more preferably, $R^y$ is $C_1$-$C_3$-alkyl; most preferably $R^y$ is methyl.

Embodiment 13: A compound according to any one of embodiments 1 to 12, wherein J is a group selected from $J^{1'}$ to $J^{12}$:

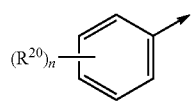 $J^{1'}$

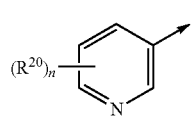 $J^{2'}$

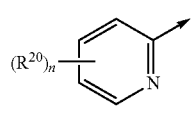 $J^{3'}$

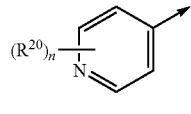 $J^{4'}$

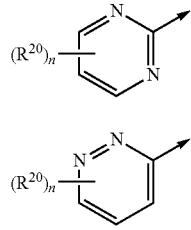 $J^5$ $J^6$

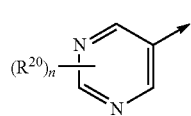 $J^7$

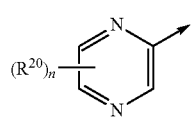 $J^8$

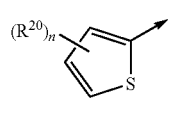 $J^9$

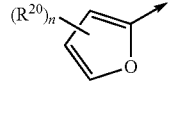 $J^{10}$

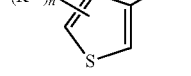 $J^{11}$

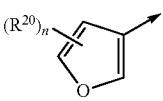 $J^{12}$ wherein n is 0, 1 or 2 and $R^{20}$ is independently selected from hydrogen, $C_1$-$C_6$alkyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_6$alkoxy, and $C_1$-$C_6$haloalkoxy.

Embodiment 14: A compound according to any one of embodiments 1 to 12, wherein J is selected from:

$J^{1'}$ $J^{2'}$ $J^{3'}$ $J^9$ $J^{11}$ more preferably J is selected from:

$J^{1'}$ $J^{9'}$ most preferably J is $J^{1'}$

Embodiment 15: A compound according to any one of embodiments 1 to 14, of formula (I)

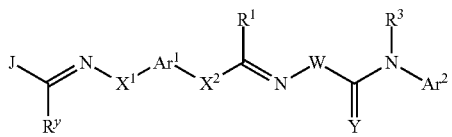
(I)

wherein
Ar$^1$ is phenyl which is unsubstituted or substituted by one to three substituents independently selected from C$_1$-C$_6$alkyl, C$_3$-C$_6$cycloalkyl, C$_1$-C$_6$haloalkyl, C$_3$-C$_6$halocycloalkyl, C$_1$-C$_3$haloalkyl-C$_3$-C$_6$cycloalkyl, C$_3$-C$_6$cycloalkoxy, halogen, C$_1$-C$_6$alkoxy and C$_1$-C$_6$haloalkoxy;

Ar$^2$ is phenyl which is unsubstituted or substituted by one to three substituents independently selected from C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_3$-C$_6$halocycloalkyl, C$_1$-C$_3$haloalkyl-C$_3$-C$_6$cycloalkyl, C$_3$-C$_6$cycloalkoxy, halogen, cyano, C$_1$-C$_6$alkoxy, C$_1$-C$_6$haloalkoxy and —S—C$_1$-C$_6$alkyl;

X$^1$ is O or NR$^6$;
X$^2$ is a bond, —CH$_2$— or —CH$_2$CH$_2$—;
W is O or NR$^2$;
Y is oxygen or sulfur;
R$^1$ is hydrogen or C$_1$-C$_6$alkyl;
R$^2$ is selected from hydrogen, C$_1$-C$_6$alkyl and C$_1$-C$_6$haloalkyl;
R$^3$ is selected from hydrogen, C$_1$-C$_6$alkyl and C$_1$-C$_6$haloalkyl;
R$^6$ is hydrogen or C$_1$-C$_6$alkyl;
J is a group selected from J$^{1'}$, J$^{2'}$, J$^{3'}$, J$^9$ and J$^{11}$:

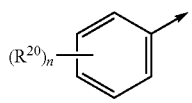
J$^{1'}$

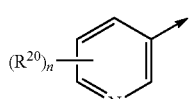
J$^{2'}$

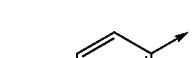
J$^{3'}$

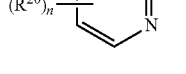
J$^9$

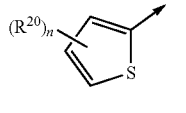
J$^{11}$

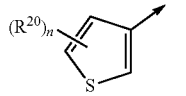

wherein n is 0, 1 or 2, and R$^{20}$ is independently selected from hydrogen, C$_3$-C$_6$halocycloalkyl and C$_1$-C$_6$haloalkoxy;

R$^y$ is C$_1$-C$_6$alkyl; or
J and R$^y$ together with the carbon atom to which they are attached form a bicyclic ring of formula

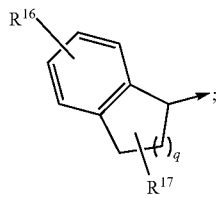

q is 1 or 2;
R$^{16}$ and R$^{17}$ are independently selected from hydrogen, C$_3$-C$_6$halocycloalkyl and C$_1$-C$_6$haloalkoxy; or an agrochemically acceptable salt, stereoisomer, tautomer, N-oxide thereof.

Embodiment 16: A compound according to any one of embodiments 1 to 15, of formula (I)

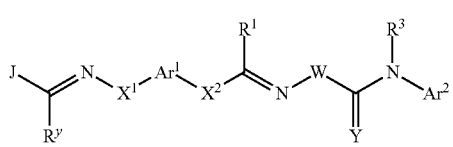
(I)

wherein
Ar$^1$ is phenyl which is unsubstituted or substituted by one to three substituents independently selected from C$_1$-C$_6$alkyl, C$_3$-C$_6$cycloalkyl, C$_1$-C$_6$haloalkyl, C$_3$-C$_6$halocycloalkyl, C$_1$-C$_3$haloalkyl-C$_3$-C$_6$cycloalkyl, C$_3$-C$_6$cycloalkoxy, halogen, C$_1$-C$_6$alkoxy and C$_1$-C$_6$haloalkoxy;

Ar$^2$ is phenyl which is unsubstituted or substituted by one to three substituents independently selected from C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_3$-C$_6$halocycloalkyl, C$_1$-C$_3$haloalkyl-C$_3$-C$_6$cycloalkyl, C$_3$-C$_6$cycloalkoxy, halogen, cyano, C$_1$-C$_6$alkoxy, C$_1$-C$_6$haloalkoxy and —S—C$_1$-C$_6$alkyl;

X$^1$ is O or NR$^6$;
X$^2$ is a bond, —CH$_2$— or —CH$_2$CH$_2$—;
W is O or NR$^2$;
Y is oxygen or sulfur;
R$^1$ is hydrogen or C$_1$-C$_6$alkyl;
R$^2$ is selected from hydrogen, C$_1$-C$_6$alkyl and C$_1$-C$_6$haloalkyl;
R$^3$ is selected from hydrogen, C$_1$-C$_6$alkyl and C$_1$-C$_6$haloalkyl;
R$^6$ is hydrogen or C$_1$-C$_6$alkyl;
J is a group selected from J$^{1'}$, J$^{2'}$, J$^{3'}$, J$^9$ and J$^{11}$:

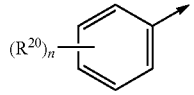
J$^{1'}$

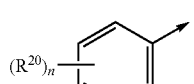
J$^{2'}$

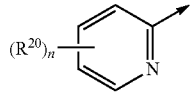
J$^{3'}$

-continued

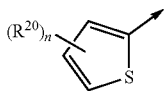

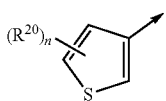

wherein n is 0, 1 or 2, and $R^{20}$ is independently selected from hydrogen, $C_3$-$C_6$halocycloalkyl and $C_1$-$C_6$haloalkoxy;

$R^y$ is $C_1$-$C_6$alkyl;

or an agrochemically acceptable salt, stereoisomer, tautomer, N-oxide thereof.

Embodiment 17: A compound according to any one of embodiments 1 to 16, of formula (Ia)

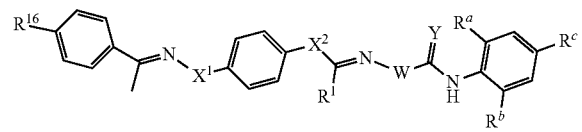

(Ia)

or formula (Ib)

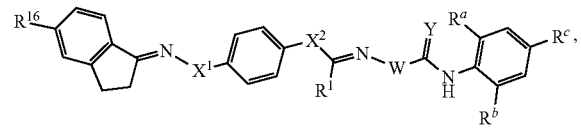

(Ib)

wherein $R^a$, $R^b$ and $R^c$ are independently selected from hydrogen, $C_1$-$C_6$alkyl, $C_1$-$C_6$haloalkyl, halogen, $C_1$-$C_6$alkoxy and $C_1$-$C_6$haloalkoxy;

$X^1$ is O or $NR^6$;
$X^2$ is a bond, —$CH_2$— or —$CH_2CH_2$—;
W is O or $NR^2$;
Y is oxygen or sulfur;
$R^1$ is hydrogen or methyl;
$R^2$ is hydrogen or $C_1$-$C_6$alkyl;
$R^6$ is hydrogen or $C_1$-$C_6$alkyl;
$R^{16}$ is $C_1$-$C_6$haloalkoxy;

or an agrochemically acceptable salt, stereoisomer, tautomer, N-oxide thereof.

Embodiment 18: A compound according to any one of embodiments 1 to 17, of formula (Ia)

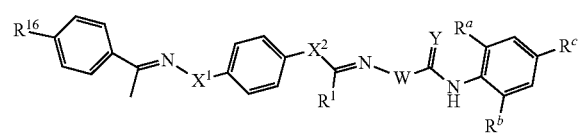

(Ia)

wherein $R^a$, $R^b$ and $R^c$ are independently selected from hydrogen, $C_1$-$C_6$alkyl, $C_1$-$C_6$haloalkyl, halogen, $C_1$-$C_6$alkoxy and $C_1$-$C_6$haloalkoxy;

$X^1$ is O or $NR^6$;
$X^2$ is a bond, —$CH_2$— or —$CH_2CH_2$—;
W is O or $NR^2$;
Y is oxygen or sulfur;
$R^1$ is hydrogen or methyl;
$R^2$ is hydrogen or $C_1$-$C_6$alkyl;
$R^6$ is hydrogen or $C_1$-$C_6$alkyl;
$R^{16}$ is $C_1$-$C_6$haloalkoxy;

or an agrochemically acceptable salt, stereoisomer, tautomer, N-oxide thereof.

Embodiment 19: A compound according to any one of embodiments 1 to 18, of formula (Ia)

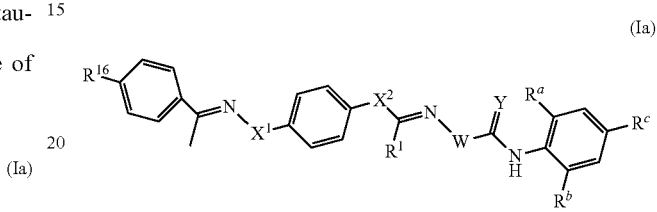

(Ia)

wherein $R^a$ is $R^b$ and $R^c$ are independently selected from hydrogen, methyl, isopropyl, trifluoromethyl, chloro, fluoro, methoxy and —$OCF_3$;

$X^1$ is selected from O, NH and $NCH_3$;
$X^2$ is a bond;
W is selected from O, NH and $NCH_3$;
Y is oxygen or sulfur;
$R^1$ is hydrogen or methyl;
$R^{16}$ is —$OCF_3$ or —$OCF_2CF_3$;

or an agrochemically acceptable salt, stereoisomer, tautomer, N-oxide thereof.

Embodiment 20: A compound according to any one of embodiments 1 to 17, of formula (Ib)

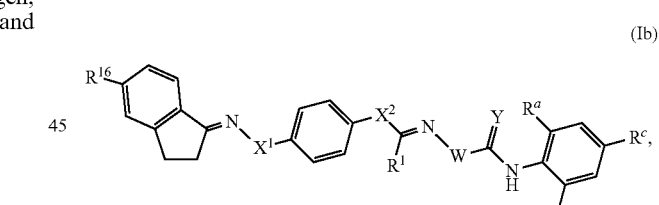

(Ib)

wherein $R^a$, $R^b$ and $R^c$ are independently selected from hydrogen, $C_1$-$C_6$alkyl, $C_1$-$C_6$haloalkyl, halogen, $C_1$-$C_6$alkoxy and $C_1$-$C_6$haloalkoxy;

$X^1$ is O or $NR^6$;
$X^2$ is a bond, —$CH_2$— or —$CH_2CH_2$—;
W is O or $NR^2$;
Y is oxygen or sulfur;
$R^1$ is hydrogen or methyl;
$R^2$ is hydrogen or $C_1$-$C_6$alkyl;
$R^6$ is hydrogen or $C_1$-$C_6$alkyl;
$R^{16}$ is $C_1$-$C_6$haloalkoxy;

or an agrochemically acceptable salt, stereoisomer, tautomer, N-oxide thereof.

Embodiment 21: A compound according to any one of embodiments 1 to 17, of formula (Ib)

(Ib)

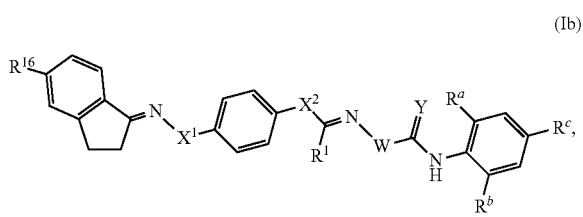

wherein $R^a$ is $R^b$ and $R^c$ are independently selected from hydrogen, methyl, isopropyl, trifluoromethyl, chloro, fluoro, methoxy and —$OCF_3$;

$X^1$ is selected from O, NH and $NCH_3$;
$X^2$ is a bond;
W is selected from O, NH and $NCH_3$;
Y is oxygen or sulfur;
$R^1$ is hydrogen or methyl;
$R^{16}$ is —$OCF_3$ or —$OCF_2CF_3$;

or an agrochemically acceptable salt, stereoisomer, tautomer, N-oxide thereof.

The compounds according to any one of embodiments 1 to 21 may be prepared according to the following Schemes 1 to 14.

Scheme 1:

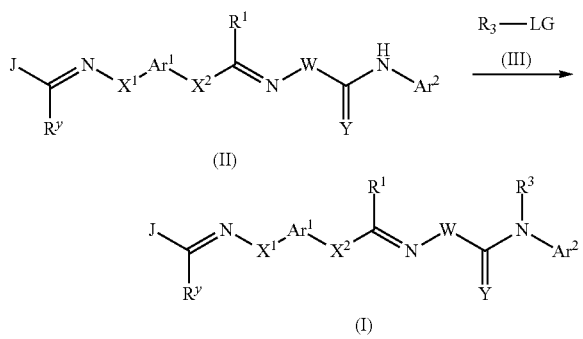

Compounds of formula (II) can be prepared, as depicted in scheme 1, by reacting compounds of formula (II) with compounds of formula (III), in the presence or in the absence of a base such as triethylamine or N,N-diisopropylethylamine, in a solvent or a solvent mixture, like, for tetrahydrofuran, DMF, dioxane or acetonitrile. The reaction temperature can preferentially range from room temperature to the boiling point of the reaction mixture. In formula (I), (II) and (III), J, $R^y$, $X^1$, $Ar^1$, $X^2$, $R^1$, W, Y and $Ar_2$ are as described above.

Scheme 2:

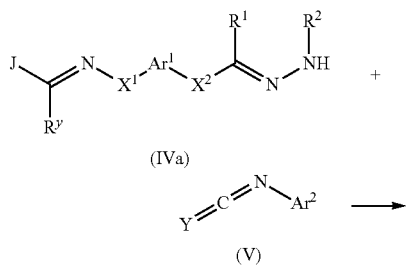

-continued

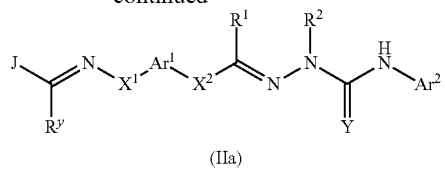

Compounds of formula (IIa) can be prepared, as depicted in scheme 2, by reacting compounds of formula (IVa) with compounds of formula (V), by methods known to those skilled in the art (see e.g. M. Smith, J. March, March's Advanced Organic Chemistry, $6^{th}$ edition, Wiley, 2007). Compounds of formula (V) can be prepared by methods known to those skilled in the art (see e.g. M. Smith, J. March, March's Advanced Organic Chemistry, $6^{th}$ edition, Wiley, 2007). In formula (IIa), (IVa) and (V), W is $NR^2$ and J, $R^y$, $X^1$, $Ar^1$, $X^2$, $R^1$, Y and $Ar_2$ are as described above.

Scheme 3:

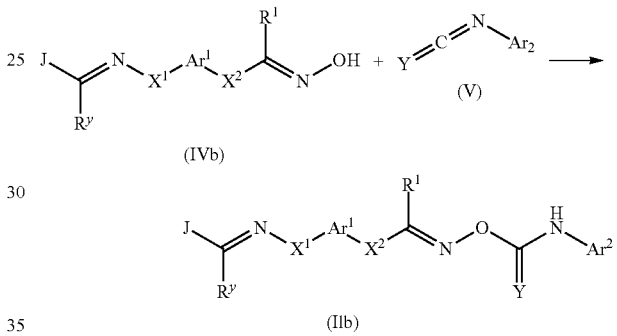

Compounds of formula (IIb) can be prepared, as depicted in scheme 3, by reacting compounds of formula (IVb) with compounds of formula (V), by methods known to those skilled in the art (see e.g. M. Smith, J. March, March's Advanced Organic Chemistry, $6^{th}$ edition, Wiley, 2007). Compounds of formula (V) can be prepared by methods known to those skilled in the art (see e.g. M. Smith, J. March, March's Advanced Organic Chemistry, $6^{th}$ edition, Wiley, 2007). In formula (lib), (IVb) and (V), W is O and J, $R^y$, $X^1$, $Ar^1$, $X^2$, $R^1$, Y and $Ar_2$ are as described above.

Scheme 4:

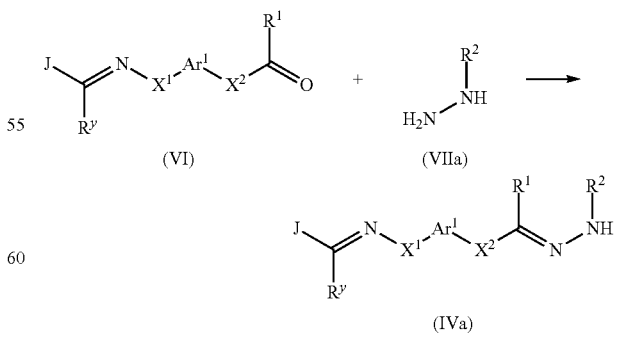

Compounds of formula (IVa) can be prepared, as depicted in scheme 4, by reacting compounds of formula (VI) with compounds of formula (VIIa), by methods known to those skilled in the art (see e.g. M. Smith, J. March, March's Advanced Organic Chemistry, 6<sup>th</sup> edition, Wiley, 2007). Compounds of formula (VIIa) can be prepared by methods known to those skilled in the art (see e.g. M. Smith, J. March, March's Advanced Organic Chemistry, 6<sup>th</sup> edition, Wiley, 2007). In formula (IVa), (VI) and (VIIa), W is NR² and J, R<sup>y</sup>, X¹, Ar¹, X² and R¹ are as described above.

Scheme 5:

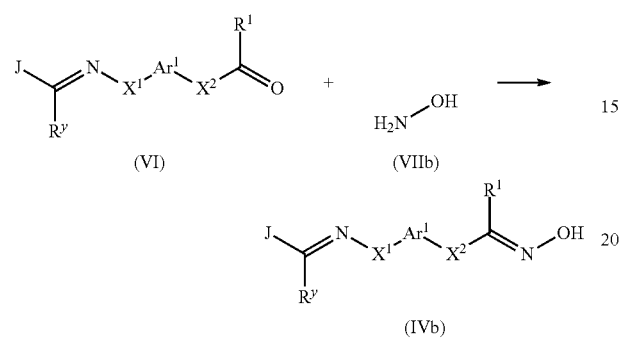

(VI)  (VIIb)

(IVb)

Compounds of formula (IVb) can be prepared, as depicted in scheme 5, by reacting compounds of formula (VI) with hydroxylamine (VIIb), by methods known to those skilled in the art (see e.g. M. Smith, J. March, March's Advanced Organic Chemistry, 6<sup>th</sup> edition, Wiley, 2007). In formula (IVb), (VI) and (VIIb), W is O and J, R<sup>y</sup>, X¹, Ar¹, X² and R¹ are as described above.

Compounds of formula (VI) can be prepared according to several methods known to those skilled in the art.

Scheme 6:

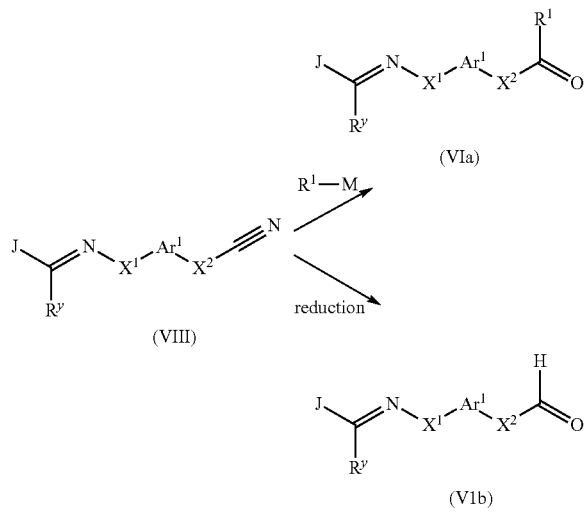

(VIa)

(VIII)

(VIb)

More specifically, compounds of formula (Via) can be prepared, as depicted in scheme 6, via addition of a compound of formula R¹—M (M is e.g. MgCl, MgBr, Li, ZnCl) to a compound of formula (VIII), by methods known to those skilled in the art (see e.g. M. Smith, J. March, March's Advanced Organic Chemistry, 6<sup>th</sup> edition, Wiley, 2007). In formula (Via) and (VIII), R¹ is not hydrogen and J, R<sup>y</sup>, X¹ and X² are as described above. Compounds of formula (VIb) can be prepared, as depicted in scheme 6, via reduction of a compound of formula (VIII) (e.g. with DIBALH), by methods known to those skilled in the art (see e.g. M. Smith, J. March, March's Advanced Organic Chemistry, 6<sup>th</sup> edition, Wiley, 2007). In formula (VIb) and (VIII), R¹ is hydrogen and J, R<sup>y</sup>, Ar¹, X¹ and X² are as described above.

Scheme 7:

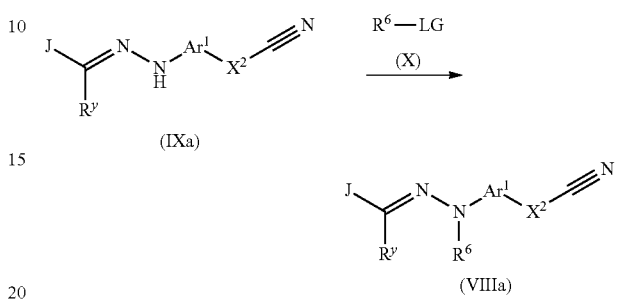

(IXa)

(VIIIa)

Compounds of formula (VIIIa) can be prepared, as depicted in scheme 7, by reacting compounds of formula (IXa) with compounds of formula (X), in the presence or in the absence of a base such as triethylamine or N,N-diisopropylethylamine, in a solvent or a solvent mixture, like, for tetrahydrofuran, DMF, dioxane or acetonitrile. The reaction temperature can preferentially range from room temperature to the boiling point of the reaction mixture. In formula (VIIIa), (IXa) and (X), X¹ is NR⁶ and J, R<sup>y</sup>, Ar¹ and X² are as described above.

Scheme 8:

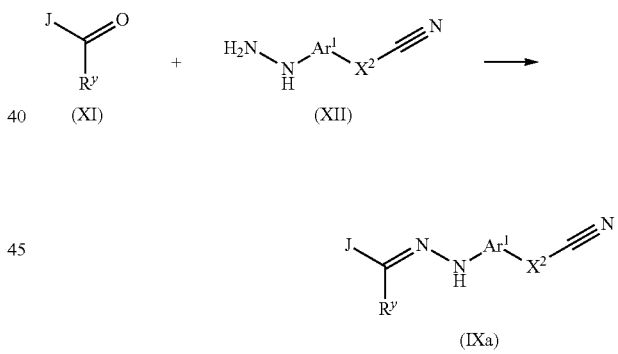

(XI)  (XII)

(IXa)

Compounds of formula (IXa) can be prepared, as depicted in scheme 8, by reacting compounds of formula (XI) with compounds of formula (XII), by methods known to those skilled in the art (see e.g. M. Smith, J. March, March's Advanced Organic Chemistry, 6<sup>th</sup> edition, Wiley, 2007). Compounds of formula (XII) can be prepared by methods (e.g. reduction of the corresponding diazonium salts) known to those skilled in the art (see e.g. M. Smith, J. March, March's Advanced Organic Chemistry, 6<sup>th</sup> edition, Wiley, 2007). When X²=direct bond, compounds of formula (XII) can be prepared starting from available materials by methods (e.g. reduction of the corresponding diazonium salts) known to those skilled in the art (see e.g. M. Smith, J. March, March's Advanced Organic Chemistry, 6<sup>th</sup> edition, Wiley, 2007). In formula (IXa), (XI) and (XII), J, R<sup>y</sup>, Ar¹ and X² are as described above.

Scheme 9:

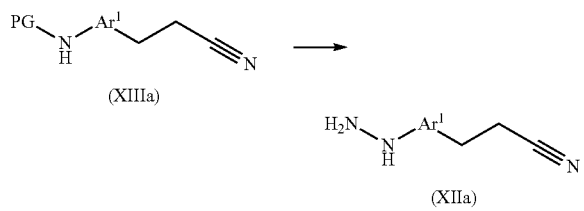

Compounds of formula (XIIa) can be prepared, as depicted in scheme 9, from compounds of formula (XIIIa), where PG=protective group (e.g. tert-butyloxycarbonyl or benzyloxycarbonyl), by methods (e.g. deprotection followed by diazonium salts formation and in situ reduction) known to those skilled in the art (see e.g. M. Smith, J. March, March's Advanced Organic Chemistry, 6$^{th}$ edition, Wiley, 2007). In formula (XIIa) and (XIIIa), Ar$^1$ is as described above.

Scheme 10:

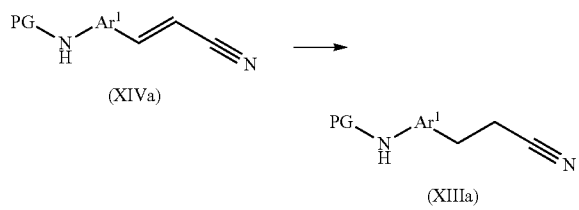

Compounds of formula (XIIIa) can be prepared, as depicted in scheme 10, from compounds of formula (XIVa), where PG=protective group (e.g. tert-butyloxycarbonyl or benzyloxycarbonyl), by methods (e.g. hydrogenation) known to those skilled in the art (see e.g. M. Smith, J. March, March's Advanced Organic Chemistry, 6$^{th}$ edition, Wiley, 2007). In formula (XIVa) and (XIIIa), Ar$^1$ is as described above.

Scheme 11:

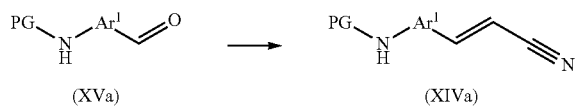

Compounds of formula (XIVa) can be prepared, as depicted in scheme 11, from compounds of formula (XVa), where PG=protective group (e.g. tert-butyloxycarbonyl or benzyloxycarbonyl), by methods (e.g. Wittig reaction) known to those skilled in the art (see e.g. M. Smith, J. March, March's Advanced Organic Chemistry, 6$^{th}$ edition, Wiley, 2007). In formula (XVa) and (XIVa), Ar$^1$ is as described above.

Scheme 12:

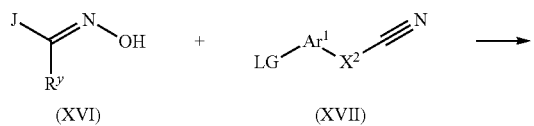

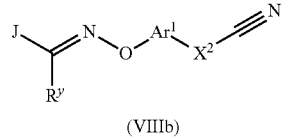

Compounds of formula (VIIIb) can be prepared, as depicted in scheme 12, by reacting compounds of formula (XVI) with compounds of formula (XVII), by methods known to those skilled in the art (see e.g. M. Smith, J. March, March's Advanced Organic Chemistry, 6$^{th}$ edition, Wiley, 2007). Compounds of formula (XVI) and (XVII) can be prepared by methods known to those skilled in the art (see e.g. M. Smith, J. March, March's Advanced Organic Chemistry, 6$^{th}$ edition, Wiley, 2007). In formula (XVII), (XVI) and (XVII), LG is a leaving group (e.g. F, NO$_2$), J, R$^y$, Ar$^1$ and X$^2$ are as described above.

Scheme 13:

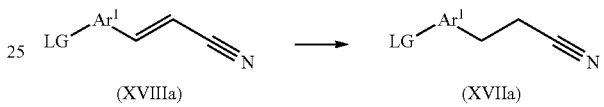

Compounds of formula (XVIIa) can be prepared, as depicted in scheme 13, from compounds of formula (XVIIIa) by methods (e.g. hydrogenation) known to those skilled in the art (see e.g. M. Smith, J. March, March's Advanced Organic Chemistry, 6$^{th}$ edition, Wiley, 2007). In formula (XVIIa) and (XVIIIa), LG is a leaving group (e.g. F, NO$_2$) and Ar$^1$ is as described above.

Scheme 14:

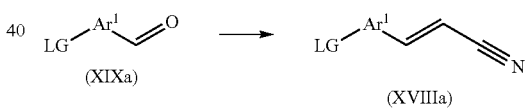

Compounds of formula (XVIIIa) can be prepared, as depicted in scheme 14, from compounds of formula (XIXa), by methods (e.g. Wittig reaction) known to those skilled in the art (see e.g. M. Smith, J. March, March's Advanced Organic Chemistry, 6$^{th}$ edition, Wiley, 2007). In formula (XIXa) and (XVIIIa), LG is a leaving group (e.g. F, NO$_2$) and Ar$^1$ is as described above.

Depending on the procedure or the reaction conditions, the compounds of formula (I), which have salt-forming properties can be obtained in free form or in the form of salts.

The compounds of formula (I) and, where appropriate, the tautomers thereof, in each case in free form or in salt form, can be present in the form of one of the stereoisomers which are possible or as a mixture of these, for example in the form of pure stereoisomers, such as antipodes and/or diastereomers, or as stereoisomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure stereoisomers and also to all stereoisomer mixtures which are possible and is to be understood in each case in this sense hereinabove and herein below, even when stereochemical details are not mentioned specifically in each case.

Diastereomer mixtures or racemate mixtures of compounds of formula (I), in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be resolved by the action of suitable agents, for example basic agents.

Pure diastereomers or enantiomers can be obtained not only by separating suitable stereoisomer mixtures, but also by generally known methods of diastereoselective or enantioselective synthesis, for example by carrying out the process according to the invention with starting materials of a suitable stereochemistry.

N-oxides can be prepared by reacting a compound of the formula (I) with a suitable oxidizing agent, for example the $H_2O_2$/urea adduct in the presence of an acid anhydride, e.g. trifluoroacetic anhydride. Such oxidations are known from the literature, for example from J. Med. Chem. 1989, 32, 2561 or WO 2000/15615.

The compounds of formula (I) and, where appropriate, the tautomers thereof, in each case in free form or in salt form, can, if appropriate, also be obtained in the form of hydrates and/or include other solvents, for example those which may have been used for the crystallization of compounds which are present in solid form.

Embodiment 22: Compounds of formula (I) according to any one of embodiments 1 to 21 are illustrated in the following Tables 1 to 48:

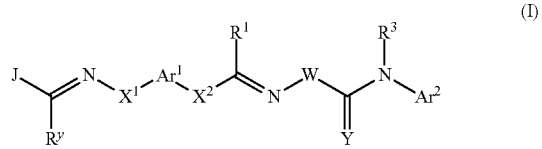
(I)

Each of Tables 1 to 24, which follows the Table A below, comprises 324 compounds of the formula (Ia) in which $X^1$, W, $R^a$, $R^b$ and $R^c$ have the values given in each row in Table A, and $X^2$, $R^1$, Y and $R^{16}$ have the values given in the relevant Tables 1 to 24. Thus for instance compound 1.001 corresponds to a compound of formula (Ia) where $X^1$, W, $R^a$, $R^b$ and $R^c$ are as defined in row 1 of Table A and where $X^2$, $R^1$, Y and $R^{16}$ are as defined in Table 1; compound 10.123 corresponds to a compound of formula (I) where $X^1$, W, $R^a$, $R^b$ and $R^c$ are as defined in row 123 of Table A and where $X^2$, $R^1$, Y and $R^{16}$ are as defined in Table 10.

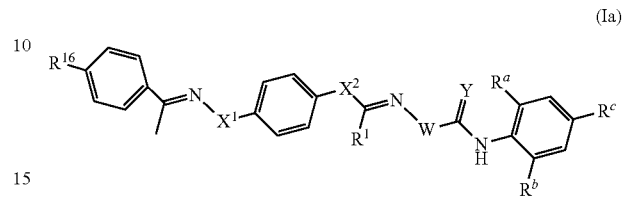
(Ia)

TABLE A

| Table A | $X^1$ | W | $R^a$ | $R^b$ | $R^c$ |
|---|---|---|---|---|---|
| 1 | O | O | $CH_3$ | $CH_3$ | H |
| 2 | NH | O | $CH_3$ | $CH_3$ | H |
| 3 | $NCH_3$ | O | $CH_3$ | $CH_3$ | H |
| 4 | O | NH | $CH_3$ | $CH_3$ | H |
| 5 | NH | NH | $CH_3$ | $CH_3$ | H |
| 6 | $NCH_3$ | NH | $CH_3$ | $CH_3$ | H |
| 7 | O | $NCH_3$ | $CH_3$ | $CH_3$ | H |
| 8 | NH | $NCH_3$ | $CH_3$ | $CH_3$ | H |
| 9 | $NCH_3$ | $NCH_3$ | $CH_3$ | $CH_3$ | H |
| 10 | O | O | iPr | $CH_3$ | H |
| 11 | NH | O | iPr | $CH_3$ | H |
| 12 | $NCH_3$ | O | iPr | $CH_3$ | H |
| 13 | O | NH | iPr | $CH_3$ | H |
| 14 | NH | NH | iPr | $CH_3$ | H |
| 15 | $NCH_3$ | NH | iPr | $CH_3$ | H |
| 16 | O | $NCH_3$ | iPr | $CH_3$ | H |
| 17 | NH | $NCH_3$ | iPr | $CH_3$ | H |
| 18 | $NCH_3$ | $NCH_3$ | iPr | $CH_3$ | H |
| 19 | O | O | Cl | $CH_3$ | H |
| 20 | NH | O | Cl | $CH_3$ | H |
| 21 | $NCH_3$ | O | Cl | $CH_3$ | H |
| 22 | O | NH | Cl | $CH_3$ | H |
| 23 | NH | NH | Cl | $CH_3$ | H |
| 24 | $NCH_3$ | NH | Cl | $CH_3$ | H |
| 25 | O | $NCH_3$ | Cl | $CH_3$ | H |
| 26 | NH | $NCH_3$ | Cl | $CH_3$ | H |
| 27 | $NCH_3$ | $NCH_3$ | Cl | $CH_3$ | H |
| 28 | O | O | $CH_3$ | H | H |
| 29 | NH | O | $CH_3$ | H | H |
| 30 | $NCH_3$ | O | $CH_3$ | H | H |
| 31 | O | NH | $CH_3$ | H | H |
| 32 | NH | NH | $CH_3$ | H | H |
| 33 | $NCH_3$ | NH | $CH_3$ | H | H |
| 34 | O | $NCH_3$ | $CH_3$ | H | H |
| 35 | NH | $NCH_3$ | $CH_3$ | H | H |
| 36 | $NCH_3$ | $NCH_3$ | $CH_3$ | H | H |
| 37 | O | O | iPr | H | H |
| 38 | NH | O | iPr | H | H |
| 39 | $NCH_3$ | O | iPr | H | H |
| 40 | O | NH | iPr | H | H |
| 41 | NH | NH | iPr | H | H |
| 42 | $NCH_3$ | NH | iPr | H | H |
| 43 | O | $NCH_3$ | iPr | H | H |
| 44 | NH | $NCH_3$ | iPr | H | H |
| 45 | $NCH_3$ | $NCH_3$ | iPr | H | H |
| 46 | O | O | Cl | H | H |
| 47 | NH | O | Cl | H | H |
| 48 | $NCH_3$ | O | Cl | H | H |
| 49 | O | NH | Cl | H | H |
| 50 | NH | NH | Cl | H | H |
| 51 | $NCH_3$ | NH | Cl | H | H |
| 52 | O | $NCH_3$ | Cl | H | H |
| 53 | NH | $NCH_3$ | Cl | H | H |
| 54 | $NCH_3$ | $NCH_3$ | Cl | H | H |
| 55 | O | O | $CH_3$ | Cl | H |
| 56 | NH | O | $CH_3$ | Cl | H |

TABLE A-continued

| Table A | $X^1$ | W | $R^a$ | $R^b$ | $R^c$ |
|---|---|---|---|---|---|
| 57 | $NCH_3$ | O | $CH_3$ | Cl | H |
| 58 | O | NH | $CH_3$ | Cl | H |
| 59 | NH | NH | $CH_3$ | Cl | H |
| 60 | $NCH_3$ | NH | $CH_3$ | Cl | H |
| 61 | O | $NCH_3$ | $CH_3$ | Cl | H |
| 62 | NH | $NCH_3$ | $CH_3$ | Cl | H |
| 63 | $NCH_3$ | $NCH_3$ | $CH_3$ | Cl | H |
| 64 | O | O | iPr | Cl | H |
| 65 | NH | O | iPr | Cl | H |
| 66 | $NCH_3$ | O | iPr | Cl | H |
| 67 | O | NH | iPr | Cl | H |
| 68 | NH | NH | iPr | Cl | H |
| 69 | $NCH_3$ | NH | iPr | Cl | H |
| 70 | O | $NCH_3$ | iPr | Cl | H |
| 71 | NH | $NCH_3$ | iPr | Cl | H |
| 72 | $NCH_3$ | $NCH_3$ | iPr | Cl | H |
| 73 | O | O | Cl | Cl | H |
| 74 | NH | O | Cl | Cl | H |
| 75 | $NCH_3$ | O | Cl | Cl | H |
| 76 | O | NH | Cl | Cl | H |
| 77 | NH | NH | Cl | Cl | H |
| 78 | $NCH_3$ | NH | Cl | Cl | H |
| 79 | O | $NCH_3$ | Cl | Cl | H |
| 80 | NH | $NCH_3$ | Cl | Cl | H |
| 81 | $NCH_3$ | $NCH_3$ | Cl | Cl | H |
| 82 | O | O | $CH_3$ | F | H |
| 83 | NH | O | $CH_3$ | F | H |
| 84 | $NCH_3$ | O | $CH_3$ | F | H |
| 85 | O | NH | $CH_3$ | F | H |
| 86 | NH | NH | $CH_3$ | F | H |
| 87 | $NCH_3$ | NH | $CH_3$ | F | H |
| 88 | O | $NCH_3$ | $CH_3$ | F | H |
| 89 | NH | $NCH_3$ | $CH_3$ | F | H |
| 90 | $NCH_3$ | $NCH_3$ | $CH_3$ | F | H |
| 91 | O | O | iPr | F | H |
| 92 | NH | O | iPr | F | H |
| 93 | $NCH_3$ | O | iPr | F | H |
| 94 | O | NH | iPr | F | H |
| 95 | NH | NH | iPr | F | H |
| 96 | $NCH_3$ | NH | iPr | F | H |
| 97 | O | $NCH_3$ | iPr | F | H |
| 98 | NH | $NCH_3$ | iPr | F | H |
| 99 | $NCH_3$ | $NCH_3$ | iPr | F | H |
| 100 | O | O | Cl | F | H |
| 101 | NH | O | Cl | F | H |
| 102 | $NCH_3$ | O | Cl | F | H |
| 103 | O | NH | Cl | F | H |
| 104 | NH | NH | Cl | F | H |
| 105 | $NCH_3$ | NH | Cl | F | H |
| 106 | O | $NCH_3$ | Cl | F | H |
| 107 | NH | $NCH_3$ | Cl | F | H |
| 108 | $NCH_3$ | $NCH_3$ | Cl | F | H |
| 109 | O | O | $CH_3$ | $CH_3$ | $OCH_3$ |
| 110 | NH | O | $CH_3$ | $CH_3$ | $OCH_3$ |
| 111 | $NCH_3$ | O | $CH_3$ | $CH_3$ | $OCH_3$ |
| 112 | O | NH | $CH_3$ | $CH_3$ | $OCH_3$ |
| 113 | NH | NH | $CH_3$ | $CH_3$ | $OCH_3$ |
| 114 | $NCH_3$ | NH | $CH_3$ | $CH_3$ | $OCH_3$ |
| 115 | O | $NCH_3$ | $CH_3$ | $CH_3$ | $OCH_3$ |
| 116 | NH | $NCH_3$ | $CH_3$ | $CH_3$ | $OCH_3$ |
| 117 | $NCH_3$ | $NCH_3$ | $CH_3$ | $CH_3$ | $OCH_3$ |
| 118 | O | O | iPr | $CH_3$ | $OCH_3$ |
| 119 | NH | O | iPr | $CH_3$ | $OCH_3$ |
| 120 | $NCH_3$ | O | iPr | $CH_3$ | $OCH_3$ |
| 121 | O | NH | iPr | $CH_3$ | $OCH_3$ |
| 122 | NH | NH | iPr | $CH_3$ | $OCH_3$ |
| 123 | $NCH_3$ | NH | iPr | $CH_3$ | $OCH_3$ |
| 124 | O | $NCH_3$ | iPr | $CH_3$ | $OCH_3$ |
| 125 | NH | $NCH_3$ | iPr | $CH_3$ | $OCH_3$ |
| 126 | $NCH_3$ | $NCH_3$ | iPr | $CH_3$ | $OCH_3$ |
| 127 | O | O | Cl | $CH_3$ | $OCH_3$ |
| 128 | NH | O | Cl | $CH_3$ | $OCH_3$ |
| 129 | $NCH_3$ | O | Cl | $CH_3$ | $OCH_3$ |
| 130 | O | NH | Cl | $CH_3$ | $OCH_3$ |
| 131 | NH | NH | Cl | $CH_3$ | $OCH_3$ |
| 132 | $NCH_3$ | NH | Cl | $CH_3$ | $OCH_3$ |
| 133 | O | $NCH_3$ | Cl | $CH_3$ | $OCH_3$ |
| 134 | NH | $NCH_3$ | Cl | $CH_3$ | $OCH_3$ |
| 135 | $NCH_3$ | $NCH_3$ | Cl | $CH_3$ | $OCH_3$ |
| 136 | O | O | $CH_3$ | H | $OCH_3$ |
| 137 | NH | O | $CH_3$ | H | $OCH_3$ |
| 138 | $NCH_3$ | O | $CH_3$ | H | $OCH_3$ |
| 139 | O | NH | $CH_3$ | H | $OCH_3$ |
| 140 | NH | NH | $CH_3$ | H | $OCH_3$ |
| 141 | $NCH_3$ | NH | $CH_3$ | H | $OCH_3$ |
| 142 | O | $NCH_3$ | $CH_3$ | H | $OCH_3$ |
| 143 | NH | $NCH_3$ | $CH_3$ | H | $OCH_3$ |
| 144 | $NCH_3$ | $NCH_3$ | $CH_3$ | H | $OCH_3$ |
| 145 | O | O | iPr | H | $OCH_3$ |
| 146 | NH | O | iPr | H | $OCH_3$ |
| 147 | $NCH_3$ | O | iPr | H | $OCH_3$ |
| 148 | O | NH | iPr | H | $OCH_3$ |
| 149 | NH | NH | iPr | H | $OCH_3$ |
| 150 | $NCH_3$ | NH | iPr | H | $OCH_3$ |
| 151 | O | $NCH_3$ | iPr | H | $OCH_3$ |
| 152 | NH | $NCH_3$ | iPr | H | $OCH_3$ |
| 153 | $NCH_3$ | $NCH_3$ | iPr | H | $OCH_3$ |
| 154 | O | O | Cl | H | $OCH_3$ |
| 155 | NH | O | Cl | H | $OCH_3$ |
| 156 | $NCH_3$ | O | Cl | H | $OCH_3$ |
| 157 | O | NH | Cl | H | $OCH_3$ |
| 158 | NH | NH | Cl | H | $OCH_3$ |
| 159 | $NCH_3$ | NH | Cl | H | $OCH_3$ |
| 160 | O | $NCH_3$ | Cl | H | $OCH_3$ |
| 161 | NH | $NCH_3$ | Cl | H | $OCH_3$ |
| 162 | $NCH_3$ | $NCH_3$ | Cl | H | $OCH_3$ |
| 163 | O | O | $CH_3$ | Cl | $OCH_3$ |
| 164 | NH | O | $CH_3$ | Cl | $OCH_3$ |
| 165 | $NCH_3$ | O | $CH_3$ | Cl | $OCH_3$ |
| 166 | O | NH | $CH_3$ | Cl | $OCH_3$ |
| 167 | NH | NH | $CH_3$ | Cl | $OCH_3$ |
| 168 | $NCH_3$ | NH | $CH_3$ | Cl | $OCH_3$ |
| 169 | O | $NCH_3$ | $CH_3$ | Cl | $OCH_3$ |
| 170 | NH | $NCH_3$ | $CH_3$ | Cl | $OCH_3$ |
| 171 | $NCH_3$ | $NCH_3$ | $CH_3$ | Cl | $OCH_3$ |
| 172 | O | O | iPr | Cl | $OCH_3$ |
| 173 | NH | O | iPr | Cl | $OCH_3$ |
| 174 | $NCH_3$ | O | iPr | Cl | $OCH_3$ |
| 175 | O | NH | iPr | Cl | $OCH_3$ |
| 176 | NH | NH | iPr | Cl | $OCH_3$ |
| 177 | $NCH_3$ | NH | iPr | Cl | $OCH_3$ |
| 178 | O | $NCH_3$ | iPr | Cl | $OCH_3$ |
| 179 | NH | $NCH_3$ | iPr | Cl | $OCH_3$ |
| 180 | $NCH_3$ | $NCH_3$ | iPr | Cl | $OCH_3$ |
| 181 | O | O | Cl | Cl | $OCH_3$ |
| 182 | NH | O | Cl | Cl | $OCH_3$ |
| 183 | $NCH_3$ | O | Cl | Cl | $OCH_3$ |
| 184 | O | NH | Cl | Cl | $OCH_3$ |
| 185 | NH | NH | Cl | Cl | $OCH_3$ |
| 186 | $NCH_3$ | NH | Cl | Cl | $OCH_3$ |
| 187 | O | $NCH_3$ | Cl | Cl | $OCH_3$ |
| 188 | NH | $NCH_3$ | Cl | Cl | $OCH_3$ |
| 189 | $NCH_3$ | $NCH_3$ | Cl | Cl | $OCH_3$ |
| 190 | O | O | $CH_3$ | F | $OCH_3$ |
| 191 | NH | O | $CH_3$ | F | $OCH_3$ |
| 192 | $NCH_3$ | O | $CH_3$ | F | $OCH_3$ |
| 193 | O | NH | $CH_3$ | F | $OCH_3$ |
| 194 | NH | NH | $CH_3$ | F | $OCH_3$ |
| 195 | $NCH_3$ | NH | $CH_3$ | F | $OCH_3$ |
| 196 | O | $NCH_3$ | $CH_3$ | F | $OCH_3$ |
| 197 | NH | $NCH_3$ | $CH_3$ | F | $OCH_3$ |
| 198 | $NCH_3$ | $NCH_3$ | $CH_3$ | F | $OCH_3$ |
| 199 | O | O | iPr | F | $OCH_3$ |
| 200 | NH | O | iPr | F | $OCH_3$ |
| 201 | $NCH_3$ | O | iPr | F | $OCH_3$ |
| 202 | O | NH | iPr | F | $OCH_3$ |
| 203 | NH | NH | iPr | F | $OCH_3$ |
| 204 | $NCH_3$ | NH | iPr | F | $OCH_3$ |
| 205 | O | $NCH_3$ | iPr | F | $OCH_3$ |
| 206 | NH | $NCH_3$ | iPr | F | $OCH_3$ |
| 207 | $NCH_3$ | $NCH_3$ | iPr | F | $OCH_3$ |
| 208 | O | O | Cl | F | $OCH_3$ |
| 209 | NH | O | Cl | F | $OCH_3$ |
| 210 | $NCH_3$ | O | Cl | F | $OCH_3$ |
| 211 | O | NH | Cl | F | $OCH_3$ |
| 212 | NH | NH | Cl | F | $OCH_3$ |

TABLE A-continued

| Table A | $X^1$ | W | $R^a$ | $R^b$ | $R^c$ |
|---|---|---|---|---|---|
| 213 | $NCH_3$ | NH | Cl | F | $OCH_3$ |
| 214 | O | $NCH_3$ | Cl | F | $OCH_3$ |
| 215 | NH | $NCH_3$ | Cl | F | $OCH_3$ |
| 216 | $NCH_3$ | $NCH_3$ | Cl | F | $OCH_3$ |
| 217 | O | O | $CH_3$ | $CH_3$ | $CF_3$ |
| 218 | NH | O | $CH_3$ | $CH_3$ | $CF_3$ |
| 219 | $NCH_3$ | O | $CH_3$ | $CH_3$ | $CF_3$ |
| 220 | O | NH | $CH_3$ | $CH_3$ | $CF_3$ |
| 221 | NH | NH | $CH_3$ | $CH_3$ | $CF_3$ |
| 222 | $NCH_3$ | NH | $CH_3$ | $CH_3$ | $CF_3$ |
| 223 | O | $NCH_3$ | $CH_3$ | $CH_3$ | $CF_3$ |
| 224 | NH | $NCH_3$ | $CH_3$ | $CH_3$ | $CF_3$ |
| 225 | $NCH_3$ | $NCH_3$ | $CH_3$ | $CH_3$ | $CF_3$ |
| 226 | O | O | iPr | $CH_3$ | $CF_3$ |
| 227 | NH | O | iPr | $CH_3$ | $CF_3$ |
| 228 | $NCH_3$ | O | iPr | $CH_3$ | $CF_3$ |
| 229 | O | NH | iPr | $CH_3$ | $CF_3$ |
| 230 | NH | NH | iPr | $CH_3$ | $CF_3$ |
| 231 | $NCH_3$ | NH | iPr | $CH_3$ | $CF_3$ |
| 232 | O | $NCH_3$ | iPr | $CH_3$ | $CF_3$ |
| 233 | NH | $NCH_3$ | iPr | $CH_3$ | $CF_3$ |
| 234 | $NCH_3$ | $NCH_3$ | iPr | $CH_3$ | $CF_3$ |
| 235 | O | O | Cl | $CH_3$ | $CF_3$ |
| 236 | NH | O | Cl | $CH_3$ | $CF_3$ |
| 237 | $NCH_3$ | O | Cl | $CH_3$ | $CF_3$ |
| 238 | O | NH | Cl | $CH_3$ | $CF_3$ |
| 239 | NH | NH | Cl | $CH_3$ | $CF_3$ |
| 240 | $NCH_3$ | NH | Cl | $CH_3$ | $CF_3$ |
| 241 | O | $NCH_3$ | Cl | $CH_3$ | $CF_3$ |
| 242 | NH | $NCH_3$ | Cl | $CH_3$ | $CF_3$ |
| 243 | $NCH_3$ | $NCH_3$ | Cl | $CH_3$ | $CF_3$ |
| 244 | O | O | $CH_3$ | H | $CF_3$ |
| 245 | NH | O | $CH_3$ | H | $CF_3$ |
| 246 | NCH3 | O | $CH_3$ | H | $CF_3$ |
| 247 | O | NH | $CH_3$ | H | $CF_3$ |
| 248 | NH | NH | $CH_3$ | H | $CF_3$ |
| 249 | $NCH_3$ | NH | $CH_3$ | H | $CF_3$ |
| 250 | O | $NCH_3$ | $CH_3$ | H | $CF_3$ |
| 251 | NH | $NCH_3$ | $CH_3$ | H | $CF_3$ |
| 252 | $NCH_3$ | $NCH_3$ | $CH_3$ | H | $CF_3$ |
| 253 | O | O | iPr | H | $CF_3$ |
| 254 | NH | O | iPr | H | $CF_3$ |
| 255 | $NCH_3$ | O | iPr | H | $CF_3$ |
| 256 | O | NH | iPr | H | $CF_3$ |
| 257 | NH | NH | iPr | H | $CF_3$ |
| 258 | $NCH_3$ | NH | iPr | H | $CF_3$ |
| 259 | O | $NCH_3$ | iPr | H | $CF_3$ |
| 260 | NH | $NCH_3$ | iPr | H | $CF_3$ |
| 261 | $NCH_3$ | $NCH_3$ | iPr | H | $CF_3$ |
| 262 | O | O | Cl | H | $CF_3$ |
| 263 | NH | O | Cl | H | $CF_3$ |
| 264 | $NCH_3$ | O | Cl | H | $CF_3$ |
| 265 | O | NH | Cl | H | $CF_3$ |
| 266 | NH | NH | Cl | H | $CF_3$ |
| 267 | $NCH_3$ | NH | Cl | H | $CF_3$ |
| 268 | O | $NCH_3$ | Cl | H | $CF_3$ |
| 269 | NH | $NCH_3$ | Cl | H | $CF_3$ |
| 270 | $NCH_3$ | $NCH_3$ | Cl | H | $CF_3$ |
| 271 | O | O | $CH_3$ | Cl | $CF_3$ |
| 272 | NH | O | $CH_3$ | Cl | $CF_3$ |
| 273 | $NCH_3$ | O | $CH_3$ | Cl | $CF_3$ |
| 274 | O | NH | $CH_3$ | Cl | $CF_3$ |
| 275 | NH | NH | $CH_3$ | Cl | $CF_3$ |
| 276 | $NCH_3$ | NH | $CH_3$ | Cl | $CF_3$ |
| 277 | O | $NCH_3$ | $CH_3$ | Cl | $CF_3$ |
| 278 | NH | $NCH_3$ | $CH_3$ | Cl | $CF_3$ |
| 279 | NCH3 | $NCH_3$ | $CH_3$ | Cl | $CF_3$ |
| 280 | O | O | iPr | Cl | $CF_3$ |
| 281 | NH | O | iPr | Cl | $CF_3$ |
| 282 | $NCH_3$ | O | iPr | Cl | $CF_3$ |
| 283 | O | NH | iPr | Cl | $CF_3$ |
| 284 | NH | NH | iPr | Cl | $CF_3$ |
| 285 | $NCH_3$ | NH | iPr | Cl | $CF_3$ |
| 286 | O | $NCH_3$ | iPr | Cl | $CF_3$ |
| 287 | NH | $NCH_3$ | iPr | Cl | $CF_3$ |
| 288 | $NCH_3$ | $NCH_3$ | iPr | Cl | $CF_3$ |
| 289 | O | O | Cl | Cl | $CF_3$ |
| 290 | NH | O | Cl | Cl | $CF_3$ |
| 291 | $NCH_3$ | O | Cl | Cl | $CF_3$ |
| 292 | O | NH | Cl | Cl | $CF_3$ |
| 293 | NH | NH | Cl | Cl | $CF_3$ |
| 294 | $NCH_3$ | NH | Cl | Cl | $CF_3$ |
| 295 | O | $NCH_3$ | Cl | Cl | $CF_3$ |
| 296 | NH | $NCH_3$ | Cl | Cl | $CF_3$ |
| 297 | $NCH_3$ | $NCH_3$ | Cl | Cl | $CF_3$ |
| 298 | O | O | $CH_3$ | F | $CF_3$ |
| 299 | NH | O | $CH_3$ | F | $CF_3$ |
| 300 | $NCH_3$ | O | $CH_3$ | F | $CF_3$ |
| 301 | O | NH | $CH_3$ | F | $CF_3$ |
| 302 | NH | NH | $CH_3$ | F | $CF_3$ |
| 303 | $NCH_3$ | NH | $CH_3$ | F | $CF_3$ |
| 304 | O | $NCH_3$ | $CH_3$ | F | $CF_3$ |
| 305 | NH | $NCH_3$ | $CH_3$ | F | $CF_3$ |
| 306 | $NCH_3$ | $NCH_3$ | $CH_3$ | F | $CF_3$ |
| 307 | O | O | iPr | F | $CF_3$ |
| 308 | NH | O | iPr | F | $CF_3$ |
| 309 | NCH3 | O | iPr | F | $CF_3$ |
| 310 | O | NH | iPr | F | $CF_3$ |
| 311 | NH | NH | iPr | F | $CF_3$ |
| 312 | $NCH_3$ | NH | iPr | F | $CF_3$ |
| 313 | O | $NCH_3$ | iPr | F | $CF_3$ |
| 314 | NH | $NCH_3$ | iPr | F | $CF_3$ |
| 315 | $NCH_3$ | $NCH_3$ | iPr | F | $CF_3$ |
| 316 | O | O | Cl | F | $CF_3$ |
| 317 | NH | O | Cl | F | $CF_3$ |
| 318 | $NCH_3$ | O | Cl | F | $CF_3$ |
| 319 | O | NH | Cl | F | $CF_3$ |
| 320 | NH | NH | Cl | F | $CF_3$ |
| 321 | $NCH_3$ | NH | Cl | F | $CF_3$ |
| 322 | O | $NCH_3$ | Cl | F | $CF_3$ |
| 323 | NH | $NCH_3$ | Cl | F | $CF_3$ |
| 324 | $NCH_3$ | $NCH_3$ | Cl | F | $CF_3$ |

Table 1:

There are provided 324 compounds of formula Ia wherein $X^2$ is direct bond, $R^1$ is H, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 2:

There are provided 324 compounds of formula Ia wherein $X^2$ is $CH_2CH_2$, $R^1$ is H, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 3:

There are provided 324 compounds of formula Ia wherein $X^2$ is direct bond, $R^1$ is $CH_3$, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 4:

There are provided 324 compounds of formula Ia wherein $X^2$ is $CH_2CH_2$, $R^1$ is $CH_3$, Y is O, $R^{16}$ is $OCF_3$ and $X^1$, W, $R^a$, $R^b$ and $R^c$ are as defined in Table A.

Table 5:

There are provided 324 compounds of formula Ia wherein $X^2$ is direct bond, $R^1$ is H, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 6:

There are provided 324 compounds of formula Ia wherein $X^2$ is $CH_2CH_2$, $R^1$ is H, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 7:

There are provided 324 compounds of formula Ia wherein $X^2$ is direct bond, $R^1$ is $CH_3$, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 8:
There are provided 324 of formula Ia wherein $X^2$ is $CH_2CH_2$, $R^1$ is $CH_3$, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 9:
There are provided 324 compounds of formula Ia wherein $X^2$ is direct bond, $R^1$ is H, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 10:
There are provided 324 compounds of formula Ia wherein $X^2$ is $CH_2CH_2$, $R^1$ is H, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 11:
There are provided 324 compounds of formula Ia wherein $X^2$ is direct bond, $R^1$ is $CH_3$, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 12:
There are provided 324 compounds of formula Ia wherein $X^2$ is $CH_2CH_2$, $R^1$ is $CH_3$, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 13:
There are provided 324 compounds of formula Ia wherein $X^2$ is direct bond, $R^1$ is H, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 14:
There are provided 324 compounds of formula Ia wherein $X^2$ is $CH_2CH_2$, $R^1$ is H, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 15:
There are provided 324 compounds of formula Ia wherein $X^2$ is direct bond, $R^1$ is $CH_3$, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 16:
There are provided 324 compounds of formula Ia wherein $X^2$ is $CH_2CH_2$, $R^1$ is $CH_3$, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.

Table 17:
There are provided 324 compounds of formula Ia wherein X2 is CH2, R1 is H, Y is O, R16 is OCF3 and X1, W, Ra, Rb and Rc are as defined in Table A; or an agrochemically acceptable salt, stereoisomer, tautomer, N-oxides thereof.

Table 18:
There are provided 324 compounds of formula Ia wherein X2 is CH2, R1 is CH3, Y is O, R16 is OCF3 and X1, W, Ra, Rb and Rc are as defined in Table A; or an agrochemically acceptable salt, stereoisomer, tautomer, N-oxides thereof.

Table 19:
There are provided 324 compounds of formula Ia wherein X2 is CH2, R1 is H, Y is S, R16 is OCF3 and X1, W, Ra, Rb and Rc are as defined in Table A; or an agrochemically acceptable salt, stereoisomer, tautomer, N-oxides thereof.

Table 20:
There are provided 324 of formula Ia wherein X2 is CH2, R1 is CH3, Y is S, R16 is OCF3 and X1, W, Ra, Rb and Rc are as defined in Table A; or an agrochemically acceptable salt, stereoisomer, tautomer, N-oxides thereof.

Table 21:
There are provided 324 compounds of formula Ia wherein X2 is CH2, R1 is H, Y is O, R16 is OCF2CF3 and X1, W, Ra, Rb and Rc are as defined in Table A; or an agrochemically acceptable salt, stereoisomer, tautomer, N-oxides thereof.

Table 22:
There are provided 324 compounds of formula Ia wherein X2 is CH2, R1 is CH3, Y is O, R16 is OCF2CF3 and X1, W, Ra, Rb and Rc are as defined in Table A; or an agrochemically acceptable salt, stereoisomer, tautomer, N-oxides thereof.

Table 23:
There are provided 324 compounds of formula Ia wherein X2 is CH2, R1 is H, Y is S, R16 is OCF2CF3 and X1, W, Ra, Rb and Rc are as defined in Table A; or an agrochemically acceptable salt, stereoisomer, tautomer, N-oxides thereof.

Table 24:
There are provided 324 compounds of formula Ia wherein X2 is CH2, R1 is CH3, Y is S, R16 is OCF2CF3 and X1, W, Ra, Rb and Rc are as defined in Table A; or an agrochemically acceptable salt, stereoisomer, tautomer, N-oxides thereof.

(Ib)

Each of Tables 25 to 48 below comprises 324 compounds of the formula (Ib) in which $X^1$, W, $R^a$, $R^b$ and $R^c$ have the values given in each row in Table A, and $X^2$, $R^1$, Y and $R^{16}$ have the values given in the relevant Tables 25 to 48. Thus for instance compound 1.025 corresponds to a compound of formula (Ib) where $X^1$, W, $R^a$, $R^b$ and $R^c$ are as defined in row 1 of Table A and where $X^2$, $R^1$, Y and $R^{16}$ are as defined in Table 25; compound 123.042 corresponds to a compound of formula (Ib) where $X^1$, W, $R^a$, $R^b$ and $R^c$ are as defined in row 123 of Table A and where $X^2$, $R^1$, Y and $R^{16}$ are as defined in Table 42.

Table 25:
There are provided 324 compounds of formula Ia wherein $X^2$ is direct bond, $R^1$ is H, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 26:
There are provided 324 compounds of formula Ib wherein $X^2$ is $CH_2CH_2$, $R^1$ is H, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 27:
There are provided 324 compounds of formula Ib wherein $X^2$ is direct bond, $R^1$ is $CH_3$, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.

Table 28:

There are provided 324 compounds of formula Ib wherein $X^2$ is $CH_2CH_2$, $R^1$ is $CH_3$, Y is O, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.
Table 29:
There are provided 324 compounds of formula Ib wherein $X^2$ is direct bond, $R^1$ is H, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.
Table 30:
There are provided 324 compounds of formula Ib wherein $X^2$ is $CH_2CH_2$, $R^1$ is H, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.
Table 31:
There are provided 324 compounds of formula Ib wherein $X^2$ is direct bond, $R^1$ is $CH_3$, Y is S, $R^{16}$ is $OCF_3$ and $X^1$, W, $R^a$, $R^b$ and $R^c$ are as defined in Table A; or an agrochemically acceptable salt, stereoisomer, tautomer, N-oxides thereof.
Table 32:
There are provided 324 compounds of formula Ib wherein $X^2$ is $CH_2CH_2$, $R^1$ is $CH_3$, Y is S, $R^1$ is $OCF_3$ and $X^1$, W, $R^a$, $R^b$ and $R^c$ are as defined in Table A; or an agrochemically acceptable salt, stereoisomer, tautomer, N-oxides thereof.
Table 33:
There are provided 324 compounds of formula Ib wherein $X^2$ is direct bond, $R^1$ is H, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 34:
There are provided 324 compounds of formula Ib wherein $X^2$ is $CH_2CH_2$, $R^1$ is H, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 35:
There are provided 324 compounds of formula Ib wherein $X^2$ is direct bond, $R^1$ is $CH_3$, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 36:
There are provided 324 compounds of formula Ib wherein $X^2$ is $CH_2CH_2$, $R^1$ is $CH_3$, Y is O, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 37:
There are provided 324 compounds of formula Ib wherein $X^2$ is direct bond, $R^1$ is H, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 38:
There are provided 324 compounds of formula Ib wherein $X^2$ is $CH_2CH_2$, $R^1$ is H, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 39:
There are provided 324 compounds of formula Ib wherein $X^2$ is direct bond, $R^1$ is $CH_3$, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 40:
There are provided 324 compounds of formula Ib wherein $X^2$ is $CH_2CH_2$, $R^1$ is $CH_3$, Y is S, $R^{16}$ is $OCF_2CF_3$ and $X^1$, W, $R^a$, $R^b$ and $R^c$ are as defined in Table A; or an agrochemically acceptable salt, stereoisomer, tautomer, N-oxides thereof.
Table 41:
There are provided 324 compounds of formula Ib wherein X2 is CH2CH2, R1 is H, Y is O, R16 is OCF3 and X1, W, Ra, Rb and Rc are as defined in Table A; or an agrochemically acceptable salt, stereoisomer, tautomer, N-oxides thereof.
Table 42:
There are provided 324 compounds of formula Ib wherein X2 is CH2CH2, R1 is CH3, Y is O, R16 is OCF3 and X1, W, Ra, Rb and Rc are as defined in Table A; or an agrochemically acceptable salt, stereoisomer, tautomer, N-oxides thereof.
Table 43:
There are provided 324 compounds of formula Ib wherein X2 is CH2CH2, R1 is H, Y is S, R16 is OCF3 and X1, W, Ra, Rb and Rc are as defined in Table A.
Table 44:
There are provided 324 compounds of formula Ib wherein X2 is CH2CH2, R1 is CH3, Y is S, R16 is OCF3 and X1, W, Ra, Rb and Rc are as defined in Table A; or an agrochemically acceptable salt, stereoisomer, tautomer, N-oxides thereof.
Table 45:
There are provided 324 compounds of formula Ib wherein X2 is CH2CH2, R1 is H, Y is O, R16 is OCF2CF3 and X1, W, Ra, Rb and Rc are as defined in Table A; or an agrochemically acceptable salt, stereoisomer, tautomer, N-oxides thereof.
Table 46:
There are provided 324 compounds of formula Ib wherein X2 is CH2CH2, R1 is CH3, Y is O, R16 is OCF2CF3 and X1, W, Ra, Rb and Rc are as defined in Table A; or an agrochemically acceptable salt, stereoisomer, tautomer, N-oxides thereof.
Table 47:
There are provided 324 compounds of formula Ib wherein X2 is CH2CH2, R1 is H, Y is S, R16 is OCF2CF3 and X1, W, Ra, Rb and Rc are as defined in Table A; or an agrochemically acceptable salt, stereoisomer, tautomer, N-oxides thereof.
Table 48:
There are provided 324 compounds of formula Ib wherein X2 is CH2CH2, R1 is CH3, Y is S, R16 is OCF2CF3 and X1, W, Ra, Rb and Rc are as defined in Table A; or an agrochemically acceptable salt, stereoisomer, tautomer, N-oxides thereof.
Embodiment 22.1: A compound according to embodiment 1, wherein the compound is selected from

| Example No. | Structures | IUPAC Name |
|---|---|---|
| 1 | 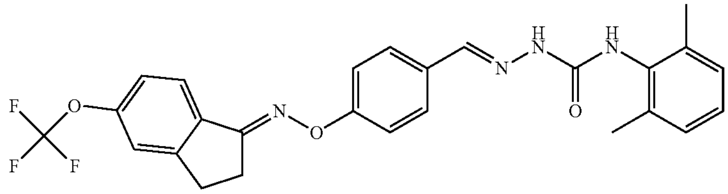 | 1-(2,6-dimethylphenyl)-3-[[4-[[5-(trifluoromethoxy)indan-1-ylidene]amino]oxyphenyl]methylene-amino]urea |
| 2 | 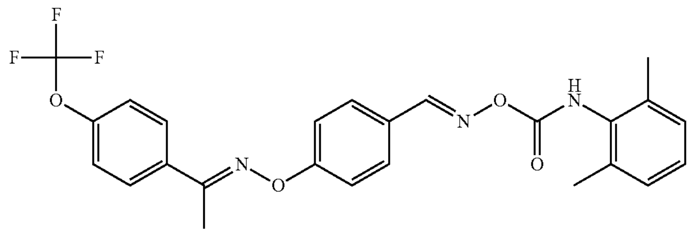 [SMILES: C/C(=N\Oc1ccc(/C=N/OC(=O)Nc2c(C)cccc2C)cc1)c1ccc(OC(F)(F)F)cc1] | [[4-[1-[4-(trifluoromethoxy)phenyl]ethylidene-amino]oxyphenyl]methyleneamino] N-(2,6-dimethylphenyl) carbamate |
| 3 | 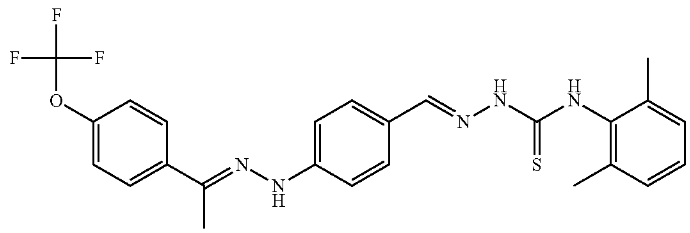 [SMILES: C/C(=N\Nc1ccc(/C=N/NC(=S)Nc2c(C)cccc2C)cc1)c1ccc(OC(F)(F)F)cc1] | 1-(2,6-dimethylphenyl)-3-[[4-[2-[1-[4-(trifluoromethoxy)phenyl]ethylidene]hydrazino]phenyl]methyleneamino]thiourea |
| 4 | 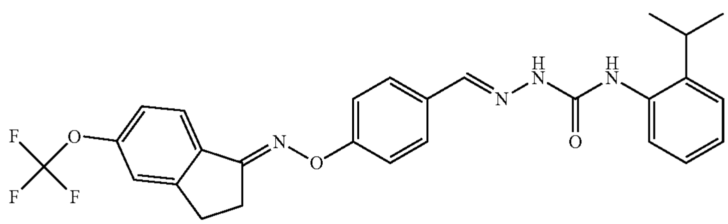 | 1-(2-isopropylphenyl)-3-[[4-[[5-(trifluoromethoxy)indan-1-ylidene]amino]oxyphenyl]methylene-amino]urea |
| 5 | 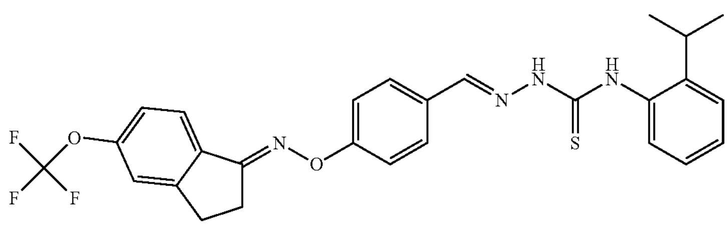 [SMILES: CC(C)c1ccccc1NC(=S)N/N=C/c1ccc(O/N=C2\CCc3cc(OC(F)(F)F)ccc32)cc1] | 1-(2-isopropylphenyl)-3-[[4-[[5-(trifluoromethoxy)indan-1-ylidene]amino]oxyphenyl]methylene-amino]thiourea |
| 6 | 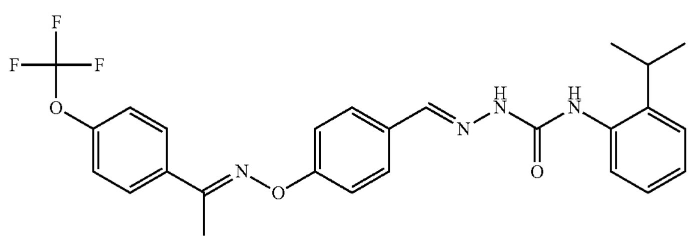 | 1-(2-isopropylphenyl)-3-[[4-[1-[4-(trifluoromethoxy)phenyl]ethylidene-amino]oxyphenyl]methylene-amino]urea |
| 7 | 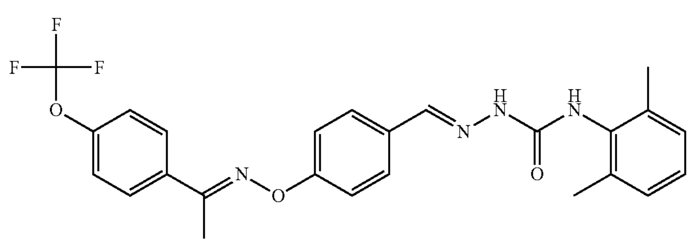 [SMILES: C/C(=N\Oc1ccc(/C=N/NC(=O)Nc2c(C)cccc2C)cc1)c1ccc(OC(F)(F)F)cc1] | 1-(2,6-dimethylphenyl)-3-[[4-[1-[4-(trifluoromethoxy)phenyl]ethylidene-amino]oxyphenyl]methylene-amino]urea |

-continued

| Example No. | Structures | IUPAC Name |
|---|---|---|
| 8 | 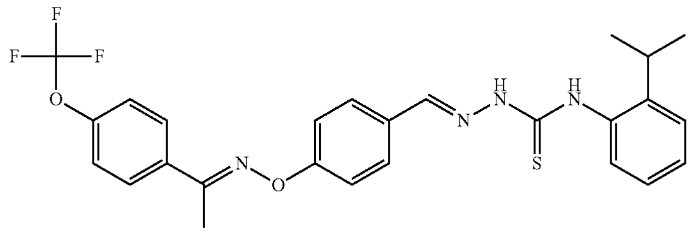 [SMILES: C/C(=N\Oc1ccc(/C=N/NC(=S)Nc2ccccc2C(C)C)cc1)c1ccc(OC(F)(F)F)cc1] | 1-(2-isopropylphenyl)-3-[[4-[1-[4-(trifluoromethoxy)phenyl]ethylidene-amino]oxyphenyl]methylene-amino]thiourea |
| 9 | 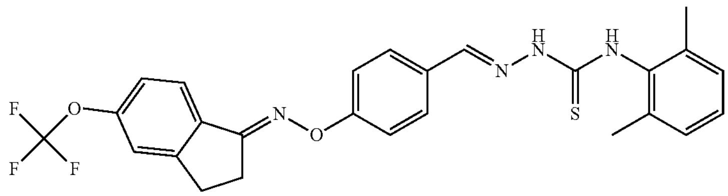 | 1-(2,6-dimethylphenyl)-3-[[4-[[5-(trifluoromethoxy)indan-1-ylidene]amino]oxyphenyl]methylene-amino]thiourea |
| 10 | 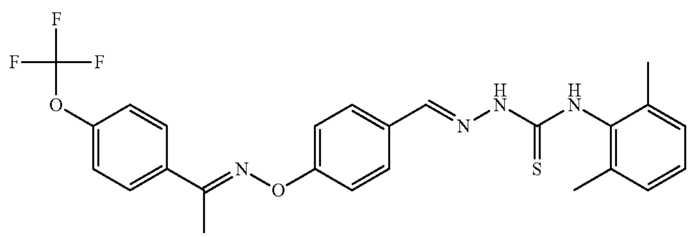 [SMILES: C/C(=N\Oc1ccc(/C=N/NC(=S)Nc2c(C)cccc2C)cc1)c1ccc(OC(F)(F)F)cc1] | 1-(2,6-dimethylphenyl)-3-[[4-[1-[4-(trifluoromethoxy)phenyl]ethylidene-amino]oxyphenyl]methylene-amino]thiourea |
| 11 | 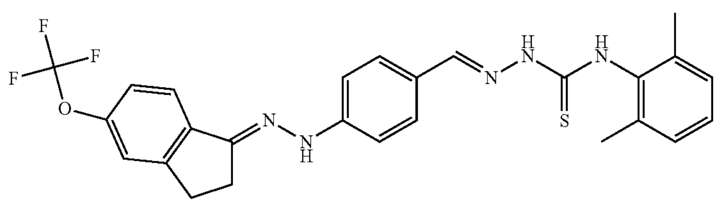 [SMILES: Cc1cccc(C)c1NC(=S)N/N=C/c1ccc(N/N=C2\CCc3cc(OC(F)(F)F)ccc32)cc1] | 1-(2,6-dimethylphenyl)-3-[[4-[2-[5-(trifluoromethoxy)indan-1-ylidene]hydrazino]phenyl]methylene-amino]thiourea |
| 12 | 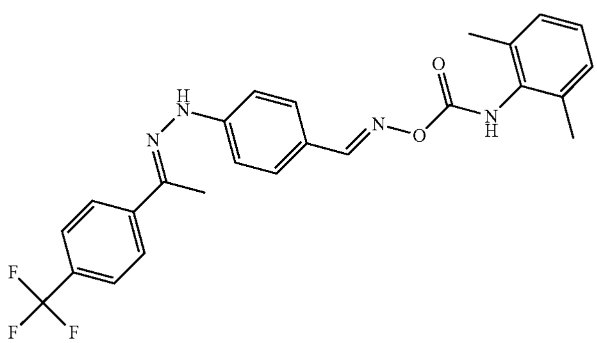 [SMILES: C/C(=N\Nc1ccc(/C=N/OC(=O)Nc2c(C)cccc2C)cc1)c1ccc(C(F)(F)F)cc1] | [[4-[2-[1-[4-(trifluoromethyl)phenyl]ethylidene]hydrazino]phenyl]methyleneamino] N-(2,6-dimethylphenyl)carbamate |
| 13 | 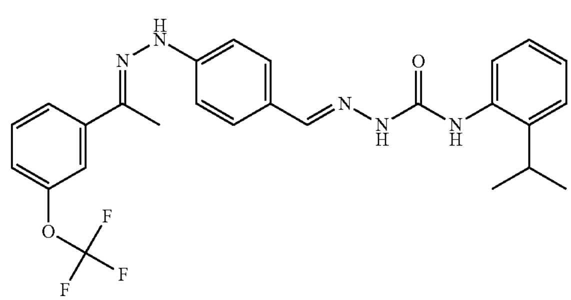 [SMILES: C/C(=N\Nc1ccc(/C=N/NC(=O)Nc2ccccc2C(C)C)cc1)c1cccc(OC(F)(F)F)c1] | 1-(2-isopropylphenyl)-3-[[4-[2-[1-[3-(trifluoromethoxy)phenyl]ethylidene]hydrazino]phenyl]methyleneamino]urea |

| Example No. | Structures | IUPAC Name |
|---|---|---|
| 14 | 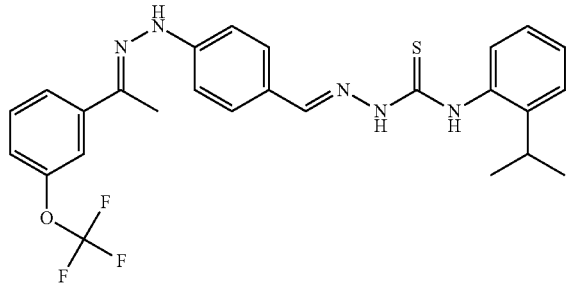 [SMILES: C/C(=N\Nc1ccc(/C=N/NC(=S)Nc2ccccc2C(C)C)cc1)c1cccc(OC(F)(F)F)c1] | 1-(2-isopropylphenyl)-3-[[4-[2-[1-[3-(trifluoromethoxy)phenyl]ethylidene]hydrazino]phenyl]methyleneamino]thiourea |
| 15 | 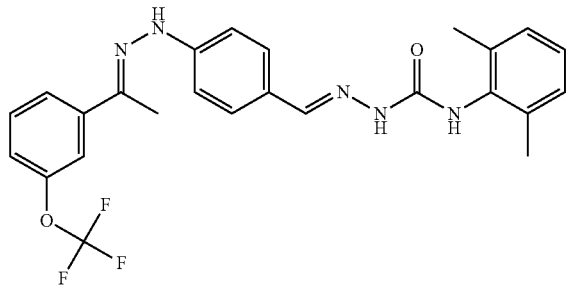 [SMILES: C/C(=N\Nc1ccc(/C=N/NC(=O)Nc2c(C)cccc2C)cc1)c1cccc(OC(F)(F)F)c1] | 1-(2,6-dimethylphenyl)-3-[[4-[2-[1-[3-(trifluoromethoxy)phenyl]ethylidene]hydrazino]phenyl]methylene-amino]urea |
| 16 | 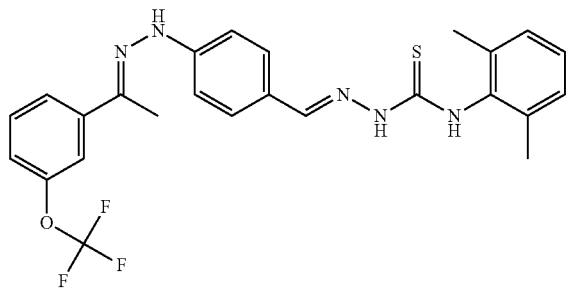 [SMILES: C/C(=N\Nc1ccc(/C=N/NC(=S)Nc2c(C)cccc2C)cc1)c1cccc(OC(F)(F)F)c1] | 1-(2,6-dimethylphenyl)-3-[[4-[2-[1-[3-(trifluoromethoxy)phenyl]ethylidene]hydrazino]phenyl]methylene-amino]thiourea |
| 17 | 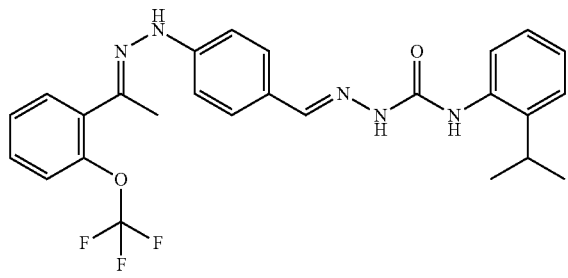 [SMILES: C/C(=N\Nc1ccc(/C=N/NC(=O)Nc2ccccc2C(C)C)cc1)c1ccccc1OC(F)(F)F] | 1-(2-isopropylphenyl)-3-[[4-[2-[1-[2-(trifluoromethoxy)phenyl]ethylidene]hydrazino]phenyl]methylene-amino]urea |
| 18 | 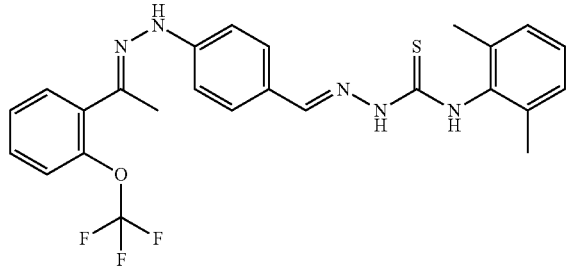 | 1-(2,6-dimethylphenyl)-3-[[4-[2-[1-[2-(trifluoromethoxy)phenyl]ethylidene]hydrazino]phenyl]methylene-amino]thiourea |

| Example No. | Structures | IUPAC Name |
|---|---|---|
| 19 | 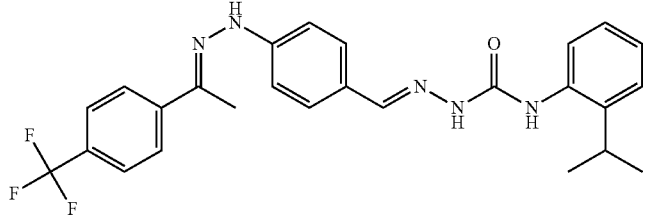 | 1-(2-isopropylphenyl)-3-[(E)-[4-[(2E)-2-[1-[4-(trifluoromethyl)phenyl]ethylidene]hydrazino]phenyl]methyleneamino]urea |
| 20 | 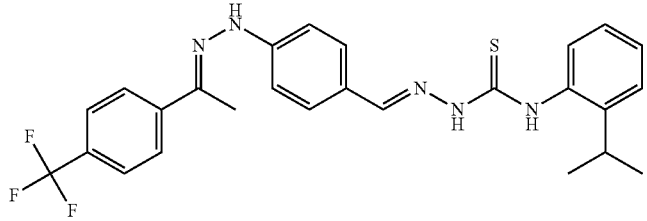 | 1-(2-isopropylphenyl)-3-[(E)-[4-[(2E)-2-[1-[4-(trifluoromethyl)phenyl]ethylidene]hydrazino]phenyl]methyleneamino]thiourea |
| 21 | 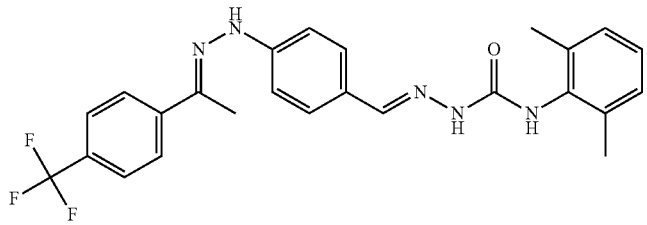 [SMILES: C/C(=N\Nc1ccc(/C=N/NC(=O)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]ethylidene]hydrazino]phenyl]methyleneamino]urea |
| 22 | 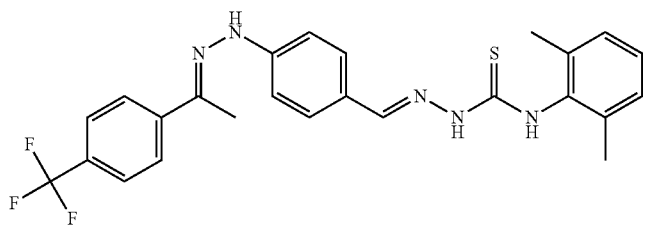 [SMILES: C/C(=N\Nc1ccc(/C=N/NC(=S)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]ethylidene]hydrazino]phenyl]methyleneamino]thiourea |
| 23 | 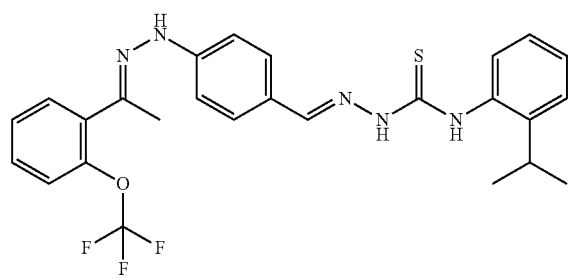 | 1-(2-isopropylphenyl)-3-[(E)-[4-[(2E)-2-[1-[2-(trifluoromethoxy)phenyl]ethylidene]hydrazino]phenyl]methylene-amino]thiourea |
| 24 | 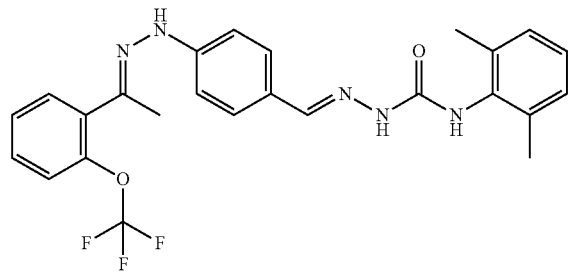 [SMILES: C/C(=N\Nc1ccc(/C=N/NC(=O)Nc2c(C)cccc2C)cc1)c1ccccc1OC(F)(F)F] | 1-(2,6-dimethylphenyl)-3-[(E)-[4-[(2E)-2-[1-[2-(trifluoromethoxy)phenyl]ethylidene]hydrazino]phenyl]methylene-amino]urea |

-continued

| Example No. | Structures | IUPAC Name |
|---|---|---|
| 25 | 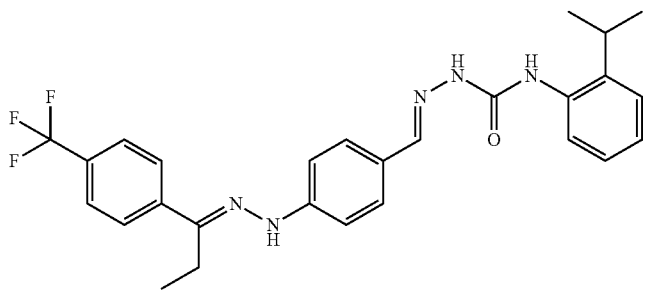 | 1-(2-isopropylphenyl)-3-[(E)-[4-[(2E)-2-[1-[4-(trifluoromethyl)phenyl]propylidene]hydrazino]phenyl]methyleneamino]urea |
| 26 | 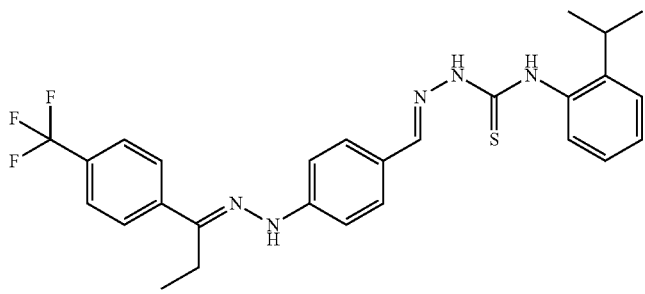 [SMILES: CC/C(=N\Nc1ccc(/C=N/NC(=S)Nc2ccccc2C(C)C)cc1)c1ccc(C(F)(F)F)cc1] | 1-(2-isopropylphenyl)-3-[(E)-[4-[(2E)-2-[1-[4-(trifluoromethyl)phenyl]propylidene]hydrazino]phenyl]methyleneamino]thiourea |
| 27 | 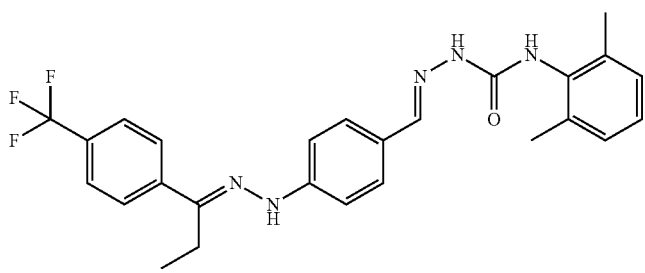 [SMILES: CC/C(=N\Nc1ccc(/C=N/NC(=O)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]propylidene]hydrazino]phenyl]methyleneamino]urea |
| 28 | 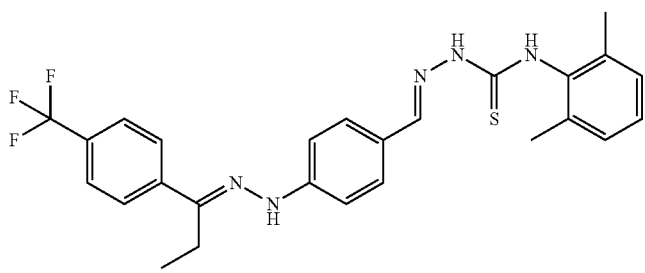 [SMILES: CC/C(=N\Nc1ccc(/C=N/NC(=S)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]propylidene]hydrazino]phenyl]methyleneamino]thiourea |
| 29 | 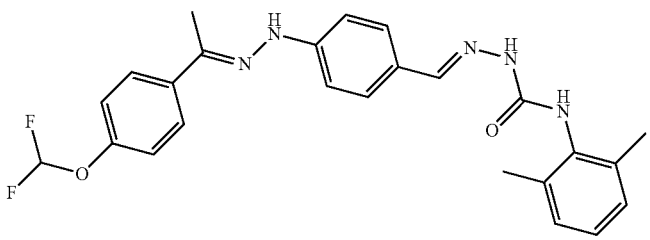 [SMILES: C/C(=N\Nc1ccc(/C=N/NC(=O)Nc2c(C)cccc2C)cc1)c1ccc(OC(F)F)cc1] | 1-[[4-[2-[1-[4-(difluoromethoxy)phenyl]ethylidene]hydrazino]phenyl]methyleneamino]-3-(2,6-dimethylphenyl)urea |

-continued

| Example No. | Structures | IUPAC Name |
|---|---|---|
| 30 | 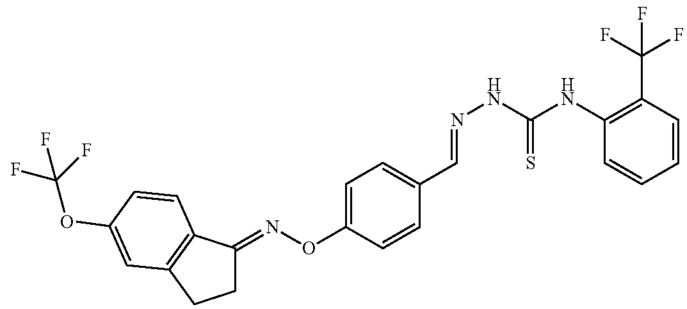 [SMILES: FC(F)(F)Oc1ccc2c(c1)CC/C2=N\Oc1ccc(/C=N/NC(=S)Nc2ccccc2C(F)(F)F)cc1] | 1-[[4-[[5-(trifluoromethoxy)indan-1-ylidene]amino]oxyphenyl]methylene-amino]-3-[2-(trifluoromethyl)phenyl]thiourea |
| 31 | | 1-[[4-[1-[4-(trifluoromethoxy)phenyl]ethylidene-amino]oxyphenyl]methylene-amino]-3-[2-(trifluoromethyl)phenyl]thiourea | or an agrochemically acceptable salt, stereoisomer, tautomer, N-oxides thereof.

The compounds according to any one of embodiments 1 to 22 are preventively and/or curatively valuable active ingredients in the field of pest control, even at low rates of application, which have a favorable biocidal spectrum and are well tolerated by warm-blooded species, fish and plants. Compounds according to any one of embodiments 1 to 22 may act against all or only individual developmental stages of normally sensitive, but also resistant, animal pests, such as insects or representatives of the order Acarina. The insecticidal or acaricidal activity of the compounds can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example, *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polypha-gotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example, *Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomy-za* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example, *Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis,*

*Scaptocoris castanea, Scotinophara* spp., *Thyanta* spp, *Triatoma* spp., and *Vatiga illudens;* from the order homoptera, for example, *Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aonidiella auranti, Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera,* and *Zyginidia scutellaris;* from the order Hymenoptera, for example, *Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.; from the order Isoptera, for example, *Coptotermes* spp, *Corniternes cumulans, Incisitermes* spp, *Macrotermes* spp, *Mastotermes* spp, *Microtermes* spp, *Reticulitermes* spp.; *Solenopsis geminate*; from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp, *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example, *Damalinea* spp. and *Trichodectes* spp.;

from the order Orthoptera, for example, *Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example, *Liposcelis* spp.;

from the order Siphonaptera, for example, *Ceratophyllus* spp., *Ctenocephalides* spp. and *Xenopsylla cheopis;* from the order Thysanoptera, for example, *Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; and/or from the order Thysanura, for example, *Lepisma saccharina.*

Examples of soil-inhabiting pests, which can damage a crop in the early stages of plant development, are:

from the order Lepidoptera, for example, *Acleris* spp., *Aegeria* spp., *Agrotis* spp., *Alabama argillaceae, Amylois* spp., *Autographa* spp., *Busseola fusca, Cadra cautella, Chilo* spp., *Crocidolomia binotalis, Diatraea* spp., *Diparopsis castanea, Elasmopalpus* spp., *Heliothis* spp., *Mamestra brassicae, Phthorimaea operculella, Plutella xylostella, Scirpophaga* spp., *Sesamia* spp., *Spodoptera* spp. and *Tortrix* spp.;

from the order Coleoptera, for example, *Agriotes* spp., *Anthonomus* spp., *Atomaria linearis, Chaetocnema tibialis, Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitotroga* spp., *Somaticus* spp., *Tanymecus* spp., *Tenebrio* spp., *Tribolium* spp., *Trogoderma* spp. and *Zabrus* spp.;

from the order Orthoptera, for example, *Gryllotalpa* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Homoptera, for example, *Eriosoma larigerum;* from the order Hymenoptera, for example, *Acromyrmex, Atta* spp., *Cephus* spp., *Lasius* spp., *Monomorium pharaonis, Neodiprion* spp., *Solenopsis* spp. and *Vespa* spp.;

from the order Diptera, for example, *Tipula* spp.;

crucifer flea beetles (*Phyllotreta* spp.), root maggots (*Delia* spp.), cabbage seedpod weevil (*Ceutorhynchus* spp.) and aphids.

The compounds according to any one of embodiments 1 to 22 may be useful for the control of nematodes. Thus, in an embodiment 23, the invention also relates to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines,*

*Heterodera schachtii, Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina*., spp *Hypsoperine* spp., *Macroposthonia* spp., *Melinius* spp., *Punctodera* spp., and *Quinisulcius* spp. In particular, the nematode species *Meloidogyne* spp., *Heterodera* spp., *Rotylenchus* spp. and *Pratylenchus* spp. can be controlled by the compounds according to any one of embodiment 1 to 22. The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

In an embodiment 24, there is also provided a method for controlling pests (such as mosquitoes and other disease vectors). In embodiment 25, the method for controlling pests comprises applying the compositions according to any one of embodiments 1 to 22 to the pests or their environment, to their locus, for example the soil or to a surface or substrate by brushing, rolling, spraying, spreading or dipping. By way of example, an IRS (indoor residual spraying) application of a surface such as a wall, ceiling or floor surface is contemplated by the method of the invention. In an embodiment 26, it is contemplated to apply such compositions to a substrate such as non-woven or a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

In embodiment 27, the invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one compound according to any one of embodiments 1 to 22 and which are to be selected to suit the intended aims and the prevailing circumstances.

Thus, in embodiment 28, the invention therefore relates to a pesticidal composition, which comprises at least one compound according to any one of embodiments 1 to 22 as active ingredient and at least one auxiliary.

Hence, in embodiment 29, the method for controlling such pests comprises applying a pesticidally effective amount of a composition according to embodiment 28 to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment 30, it is contemplated to apply a composition according to embodiment 28 for residual control of pests on a substrate such as a fabric material in the form of (or which can be used in the manufacture of) netting, clothing, bedding, curtains and tents.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants). Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
  active ingredient: 1 to 95%, preferably 5 to 20%
  surfactant: 1 to 30%, preferably 10 to 20%
  solvent: 5 to 98%, preferably 70 to 85%
Dusts:
  active ingredient: 0.1 to 10%, preferably 0.1 to 1%
  solid carrier: 99.9 to 90%, preferably 99.9 to 99%
Suspension Concentrates:
  active ingredient: 5 to 75%, preferably 10 to 50%
  water: 94 to 24%, preferably 88 to 30%
  surfactant: 1 to 40%, preferably 2 to 30%
Wettable Powders:
  active ingredient: 0.5 to 90%, preferably 1 to 80%
  surfactant: 0.5 to 20%, preferably 1 to 15%
  solid carrier: 5 to 99%, preferably 15 to 98%
Granulates:
  active ingredient: 0.5 to 30%, preferably 3 to 15%
  solid carrier: 99.5 to 70%, preferably 97 to 85%

The activity of compositions comprising compounds according to the invention can be broadened considerably, and adapted to prevailing circumstances, by including other active substances. The active substances can be of chemical or biological in type, and in the case of biological could be further modified from the biological species derived in nature. Active substances include substances that control, repel or attract pests that damage or harm useful plants in general, but also substances that improve the growth of a useful plant, such as plant growth regulators, and substances that improve the performance of the active substance, such as synergists. Examples are insecticides, acaricides, nematicides, molluscicides, aligicides, virusicides, rodenticide, bactericides, fungicides, chemosterilants, anthelmintics. Examples of a biological active substance include baculovirus, plant extract, and bacteria.

The mixtures of the compounds according to any one of embodiments 1 to 22 with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Individual active substances can occur in more than one group or class, and at more than one place within a group or class: information about the active substances, their spectrum, sources and classifications can be found from Compendium of Pesticide Common Names (see http://www.alanwood.net/pesticides/index.html) or from the Pesticide Manual created by the British Crop Production Counci (see http://bcpcdata.com/pesticide-manual.html).

Preferred mixtures are indicated below where a compound according to any one of embodiment 1 to 22 is indicated as "I".

Compositions comprising an adjuvant include I+compounds selected from the group of substances consisting of petroleum oils;

Compositions comprising an acaricide include I+1,1-bis (4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cypermethrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+dicliphos, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoate-methyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl 0-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+ometephosomate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+polychloroterpenes, I+polynactins, I+proclonol, I+profenofos, I+promacyl, I+propargite, I+propetamphos, I+propoxur, I+prothiodathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302;

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate;

Compositions comprising an avicide include I+chloralose, I+endrin, I+fenthion, I+pyridin-4-amine and I+strychnine;

Compositions comprising a biological control agent include I+*Adoxophyes orana* GV, I+*Agrobacterium radiobacter*, I+*Amblyseius* spp., I+*Anagrapha falcifera* NPV, I+*Anagrus atomus*, I+*Aphelinus abdominalis*, I+*Aphidius colemani*, I+*Aphidoletes aphidimyza*, I+*Autographa californica* NPV, I+*Bacillus firmus*, I+*Bacillus sphaericus* Neide, I+*Bacillus thuringiensis* Berliner, I+*Bacillus thuringiensis* subsp. *aizawai*, I+*Bacillus thuringiensis* subsp. *israelensis*, I+*Bacillus thuringiensis* subsp. *japonensis*, I+*Bacillus thuringiensis* subsp. *kurstaki*, I+*Bacillus thuringiensis* subsp. *tenebrionis*, I+*Beauveria bassiana*, I+*Beauveria brongniartii*, I+*Chrysoperla carnea*, I+*Cryptolaemus montrouzieri*, I+*Cydia pomonella* GV, I+*Dacnusa sibirica*, I+*Diglyphus isaea*, I+*Encarsia formosa*, I+*Eretmocerus eremicus*, I+*Helicoverpa zea* NPV, I+*Heterorhabditis bacteriophora* and *H. megidis*, I+*Hippodamia convergens*, I+*Leptomastix dactylopii*, I+*Macrolophus caliginosus*, I+*Mamestra brassicae* NPV, I+*Metaphycus helvolus*, I+*Metarhizium anisopliae* var. *acridum*, I+*Metarhizium anisopliae* var. *anisopliae*, I+*Neodiprion sertifer* NPV and *N. lecontei* NPV, I+*Orius* spp., I+*Paecilomyces fumosoroseus*, I+*Phytoseiulus persimilis*, I+*Spodoptera exigua* multicapsid nuclear polyhedrosis virus, I+*Steinernema bibionis*, I+*Steinernema carpocapsae*, I+*Steinernema feltiae*, I+*Steinernema glaseri*, I+*Steinernema riobrave*, I+*Steinernema riobravis*, I+*Steinernema scapterisci*, I+*Steinernema* spp., I+*Trichogramma* spp., I+*Typhlodromus occidentalis* and I+*Verticillium lecanii*;

Compositions comprising a soil sterilant include I+iodomethane and methyl bromide; Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa; Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2, 13-dien-1-yl acetate, I+octadeca-3,13-dien-1-yl acetate, I+orfralure, I+oryctalure, I+ostramone, I+siglure, I+sordidin, I+sulcatol, I+tetradec-11-en-1-yl acetate, I+trimedlure, I+trimedlure A, I+trimedlure $B_1$, I+trimedlure $B_2$, I+trimedlure C and I+trunc-call;

Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin;

Compositions comprising an insecticide include I+1-dichloro-1-nitroethane, I+1,1-dichloro-2,2-bis(4-ethylphenyl) ethane, I+, I+1,2-dichloropropane, I+1,2-dichloropropane with 1,3-dichloropropene, I+1-bromo-2-chloroethane, I+2, 2,2-trichloro-1-(3,4-dichlorophenyl)ethyl acetate, I+2,2-dichlorovinyl 2-ethylsulfinylethyl methyl phosphate, I+2-(1, 3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl (prop-2-ynyl)aminophenyl methylcarbamate, I+2-thiocyanatoethyl laurate, I+3-bromo-1-chloroprop-1-ene, I+3-methyl-1-phenylpyrazol-5-yl dimethyl-carbamate, I+4-methyl(prop-2-ynyl)amino-3,5-xylyl methylcarbamate, I+5, 5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+*Bacillus thuringiensis* delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenothion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I, I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxy-aminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone Ill, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O-5-dichloro-4-iodophenyl O-ethyl ethylphosphonothioate, I+O,O-diethyl O-4-methyl-2-oxo-2H-chromen-7-yl phosphorothioate, I+O,O-diethyl O-6-methyl-2-propylpyrimidin-4-yl phosphorothioate, I+O,O,O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+polychloroterpenes, I+potassium arsenite, I+potassium thiocyanate, I+prallethrin, I+precocene I, I+precocene II, I+precocene Ill, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacarb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim; Compositions comprising a molluscicide include I+bis(tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole; Compositions comprising a nematicide include 1+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+*Myrothecium verrucaria* composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone;

Compositions comprising a synergist include I+2-(2-butoxyethoxy)ethyl piperonylate, I+5-(1,3-benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide;

Compositions comprising an animal repellent include 1+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram; Further compositions include I+Brofluthrinate, I+Cycloxaprid, I+Diflovidazine, I+Flometoquin, I+Fluhexafon, I+Guadipyr, I+*Plutella xylostella* Granulosis virus, I+*Cydia pomonella* Granulosis virus, I+Harpin, I+Imicyafos, I+*Heliothis virescens* Nucleopolyhedrovirus, I+*Heliothis punctigera* Nucleopolyhedrovirus, I+*Helicoverpa armigera* Nucleopolyhedrovirus, I+*Helicoverpa zea* Nucleopolyhedrovirus, I+*Spodoptera frugiperda* Nucleopolyhedrovirus, I+*Plutella xylostella* Nucleopolyhedrovirus, I+*Pasteuria nishizawae*, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene;

Composition also include mixtures of compound of formula I and an active substance referenced by a code, such as I+code AE 1887196 (BSC-BX60309), I+code NNI-0745 GR, I+code IKI-3106, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS-CL73507, I+code S-1871, I+code DPX-RDS63, and I+code AKD-1193.

The active ingredient mixture of the compounds according to any one of embodiments 1 to 22 with active ingredients described above comprises a compound according to any one of embodiments 1 to 22 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

In embodiment 31, the mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound according to any one of embodiments 1 to 22 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds according to any one of embodiments 1 to 22 and the active ingredients as described above is not essential for working the present invention.

The compositions according to embodiment 31 can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to embodiment 31 are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds according to any one of embodiments 1 to 22 and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

In embodiment 32, the invention therefore relates to a method for the protection of plant propagation material from the attack by pests, which comprises treating the propagation material or the site, where the propagation material is planted, with a compound according to any one of embodiments 1 to 22 or with a composition according to embodiment 28 or 31, which comprises at least one compound according to any one of embodiments 1 to 22, as active ingredient and at least one auxiliary composition.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound according to any one of embodiments 1 to 22.

Seed treatment comprises all suitable seed treatment techniques known in the art, such as seed dressing, seed coating, seed dusting, seed soaking and seed pelleting. The seed treatment application of the compound according to any one of embodiments 1 to 22 can be carried out by any known methods, such as spraying or by dusting the seeds before sowing or during the sowing/planting of the seeds.

EXPERIMENTAL

Preparatory Examples: The following examples are intended to illustrate the invention and are not to be construed as being limitations thereon.

"Mp" means melting point in ° C. $^1$H NMR measurements were recorded on a Brucker 400 MHz spectrometer, chemical shifts are given in ppm relevant to a TMS standard. Spectra measured in deuterated solvents as indicated.

Example 1:

Preparation of [1-(2,6-dimethylphenyl)-3-[[4-[[5-(trifluoromethoxy)indan-1-ylidene]amino]oxyphenyl]methyleneamino]urea

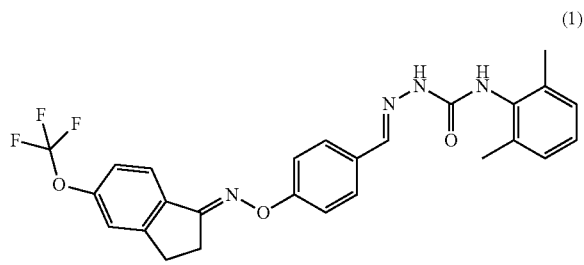 [SMILES: Cc1cccc(C)c1NC(=O)N/N=C/c1ccc(O/N=C2\CCc3cc(OC(F)(F)F)ccc32)cc1]

Step A-1: Preparation of 4-[[5-(trifluoromethoxy)indan-1-ylidene]amino]oxybenzonitrile

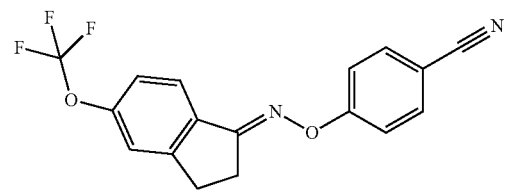 [SMILES: N#Cc1ccc(O/N=C2\CCc3cc(OC(F)(F)F)ccc32)cc1]

To a solution of 5-(trifluoromethoxy)indan-1-one oxime (1.0 eq., 2.07 g) in N,N-dimethylformamide (295 mL), 4-fluorobenzonitrile (1.0 eq., 1.08 g) and potassium tert-butoxyde (1.2 eq., 10.7 mL of 1M solution in tetrahydrofuran) were added dropwise under argon at 0° C. The mixture was then allowed to warm to room temperature. After 1 h, the reaction mixture was slowly poured into a mixture of HCl (1M)/ethyl acetate. The organic layer was washed with water, brine, dried over Na$_2$SO$_4$, filtrated and evaporated. The residue was submitted to column chromatography to give the title compound as a solid.

$^1$H NMR (400 MHz, CDCl$_3$) δ ppm: 7.86 (d, 1H), 7.56-7.71 (m, 2H), 7.31-7.44 (m, 2H), 7.12-7.26 (m, 2H), 3.18 (s, 4H)

Step A-2: Preparation of 4-[[5-(trifluoromethoxy)indan-1-ylidene]amino]oxybenzaldehyde

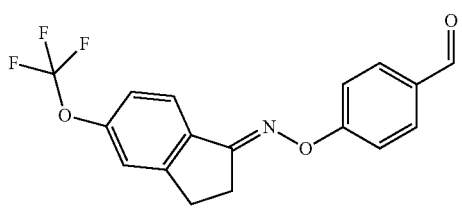 [SMILES: O=Cc1ccc(O/N=C2\CCc3cc(OC(F)(F)F)ccc32)cc1]

To a solution of 4-[([6-(trifluoromethoxy)indan-1-ylidene]amino]oxybenzonitrile (1.0 eq., 1.968 g) in dichloromethane (59 mL) was added DIBAL-H (1.0 mol/L) in dichloromethane (1.1 eq., 6.5 mL, 8.0 g) at 0° C. The mixture was stirred at this temperature for 1 h, then quenched by careful addition of water at 0° C. and allowed to warm to room temperature. The aqueous layer was extracted twice with ethyl acetate, the organic phase dried over sodium sulphate and the solvent evaporated. The crude reaction mixture was used without purification in the following step.

Step A-3: Preparation of [1-(2,6-dimethylphenyl)-3-[[4-[[5-(trifluoromethoxy)indan-1-ylidene]amino]oxyphenyl]methyleneamino]urea (1)

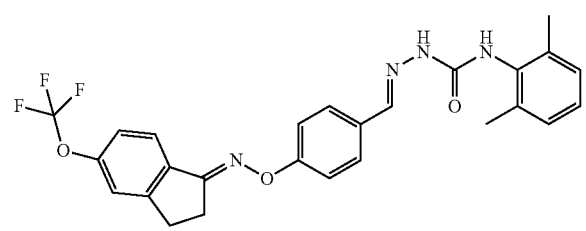

To a solution of 4-[[5-(trifluoromethoxy)indan-1-ylidene]amino]oxybenzaldehyde (1.0 eq., 0.1 g) in methanol (2.9 mL) was added 1-amino-3-(2,6-dimethylphenyl)urea (1.05 eq., 0.056 g) at room temperature. The reaction mixture was then stirred at 65° C. overnight. The resulting white precipitate was filtered, washed twice with methanol and pentane.

Mp=174-176° C. $^1$H NMR (400 MHz, DMSO-d$_6$) δ ppm: 10.44-10.50 (m, 1H), 8.44-8.51 (m, 1H), 7.87-7.92 (m, 2H), 7.80-7.86 (m, 2H), 7.47-7.52 (m, 1H), 7.32-7.38 (m, 1H), 7.24-7.31 (m, 2H), 7.09 (s, 3H), 3.10-3.21 (m, 4H), 2.21 (s, 6H)

Example 2:

Preparation of [([4-[1-[4-(trifluoromethoxy)phenyl]ethylideneamino]oxyphenyl]methyleneamino] N-(2,6-dimethylphenyl)carbamate (2)

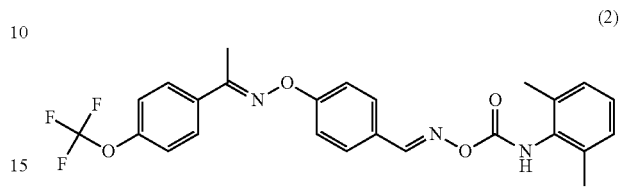

Step B-1: Preparation of 4-[1-[4-(trifluoromethoxy)phenyl]ethylideneamino]oxybenzonitrile

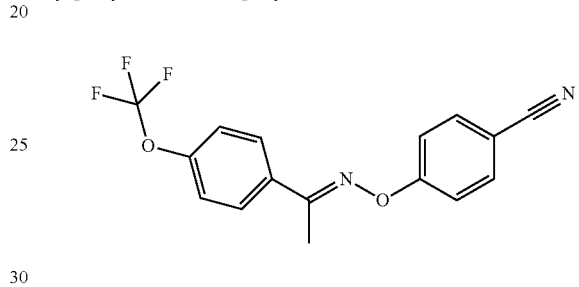

4-nitrobenzonitrile (1.0 eq., 0.48 g) was added to a mixture of 1-[4-(trifluoromethoxy)phenyl]ethanone oxime (1.0 eq., 0.72 g) and dipotassium carbonate (1.0 eq., 0.45 g) in acetonitrile (16 mL). The reaction mixture was heated at 85° C. and stirred at this temperature until full conversion was observed. The mixture was then allowed to cool down to room temperature before filtering the precipitate. The solid was washed with diethyl ether and then was submitted to column chromatography to give the title compound as a solid.

$^1$H NMR (400 MHz, CDCl$_3$) δ ppm: 7.82 (d, 2H), 7.65 (d, 2H), 7.37 (d, 2H), 7.30 (d, 2H), 2.49 (s, 3H).

Step B-2: Preparation of 4-[1-[4-(trifluoromethoxy)phenyl]ethylideneamino]oxybenzaldehyde

To a solution of 4-[1-[3-(trifluoromethoxy)phenyl]ethylideneamino]oxybenzonitrile (1.0 eq., 0.64 g) in dichloromethane (20 mL) was added DIBAL-H (1.0 mol/L) in dichloromethane (1.1 eq., 2.2 mL) at 0° C.

The mixture was stirred at this temperature for 1 h, then quenched by careful addition of water at 0° C. and allowed to warm to room temperature. The aqueous layer was extracted twice with ethyl acetate, the organic phase dried over sodium sulphate and the solvent evaporated. The crude reaction mixture was used without purification in the following step.

Step B-3: Preparation of [1-[4-(trifluoromethoxy)phenyl]ethylideneamino]oxybenzaldehyde oxime

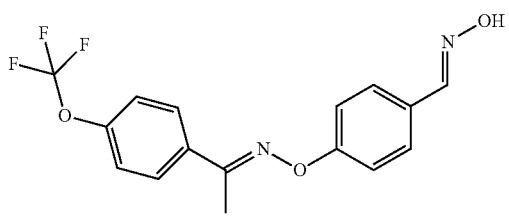 [SMILES: C/C(=N\Oc1ccc(/C=N/O)cc1)c1ccc(OC(F)(F)F)cc1]

To a solution of 4-[1-[4-(trifluoromethoxy)phenyl]ethylideneamino]oxybenzaldehyde (1.0 eq., 0.06 g) in methanol (0.9 mL) were added hydroxylammonium chloride (2.3 eq., 0.02 mL) then sodium acetate trihydrate (2.5 eq., 0.04 g). The reaction mixture was then heated at 70° C. and stirred for 1 h. The mixture was then allowed to cool down to room temperature before filtering the precipitate. The liquid was evaporated and then dissolved in a mixture of ethyl acetate/HCl (1N). The aqueous layer was extracted twice with ethyl acetate, the organic phase dried over sodium sulphate and the solvent evaporated, to afford the title compound as a solid.

$^1$H NMR (400 MHz, DMSO-$d_6$) δ ppm: 8.11 (s, 1H), 7.97 (d, 2H), 7.60 (d, 2H), 7.48 (d, 2H), 7.31 (d, 2H), 2.47 (s, 3H).

Step B-4: Preparation of [1-[4-(trifluoromethoxy)phenyl]ethylideneamino]oxyphenyl]methyleneamino]N-(2,6-dimethylphenyl)carbamate (compound 2)

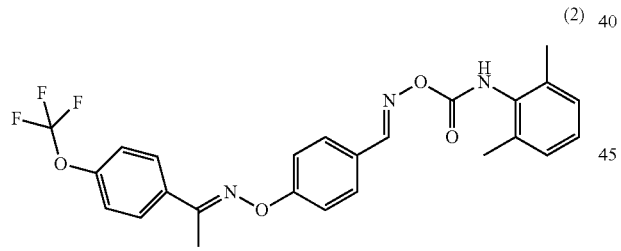

To a solution of 1-[4-(trifluoromethoxy)phenyl]ethylideneamino]oxybenzaldehyde oxime (1.0 eq., 59 mg) in tetrahydrofuran (5.5 mL) was added 2,6-dimethylphenyl-isocyanate (3.0 eq., 79 mg) under argon at room temperature. The reaction mixture was then stirred at 65° C. overnight. The resulting white precipitate was filtered, and then was submitted to column chromatography to give the title compound as a solid. Mp=145-152° C.

1H NMR (400 MHz, CDCl3) δ ppm: 8.41-8.48 (m, 1H), 7.83-7.89 (m, 2H), 7.66-7.76 (m, 3H), 7.37-7.43 (m, 2H), 7.31-7.34 (m, 2H), 7.12-7.19 (m, 3H), 2.47-2.54 (m, 3H), 2.33-2.40 (m, 6H).

Example 3:

Preparation of 1-(2,6-dimethylphenyl)-3-[[4-[2-[1-[4-(trifluoromethoxy)phenyl]ethylidene]hydrazino]phenyl]methyleneamino]thiourea

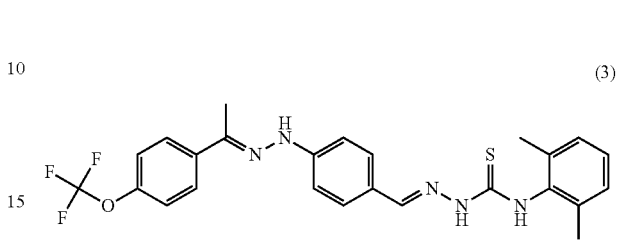

Step C-1: Preparation of tert-butyl N-(4-methanehydrazonoylphenyl)carbamate

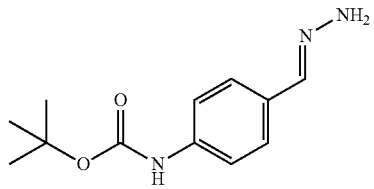 [SMILES: CC(C)(C)OC(=O)Nc1ccc(/C=N/N)cc1]

tert-butyl N-(4-formylphenyl)carbamate (1.0 eq., 0.75 g) was added to a solution of hydrazine hydrate (10.0 eq., 4.8 g) in ethanol (34 mL) at 80° C. The resulting mixture was stirred at reflux for 1 h, the allowed to cool down to room temperature. The organic phase dried over sodium sulphate and the solvent evaporated. The crude reaction mixture was used without purification in the following step.

Step C-2: Preparation of tert-butyl N-[4-[[(2,6-dimethylphenyl)carbamothioylhydrazono]methyl]phenyl]carbamate

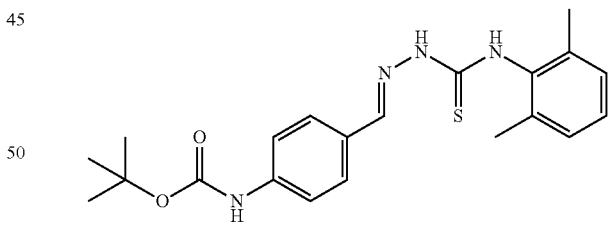

To a solution of 2-isothiocyanato-1,3-dimethyl-benzene (2.8 eq., 1.3 g) in tetrahydrofuran (29 mL) was added tert-butyl N-(4-methanehydrazonoylphenyl)carbamate (1.0 eq., 0.7 g). The reaction mixture was then stirred at 65° C. overnight. The resulting white precipitate was filtered off, the filtrate was evaporated and was then submitted to column chromatography to give the title compound as a solid.

1H NMR (400 MHz, DMSO-d6) δ ppm: 11.65 (s, 1H), 9.77 (s, 1H), 9.54 (s, 1H), 8.04 (s, 1H), 7.78 (d, 2H), 7.49 (d, 2H), 7.11 (m, 3H), 2.18 (s, 6H), 1.48 (s, 9H).

Step C-3: Preparation of 1-[(4-aminophenyl)methyleneamino]-3-(2,6-dimethylphenyl)thiourea

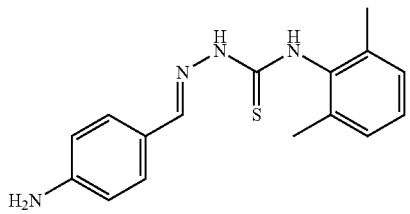 [SMILES: Cc1cccc(C)c1NC(=S)N/N=C/c1ccc(N)cc1]

To a cold solution of tert-butyl N-[4-[[(2,6-dimethylphenyl)carbamothioylhydrazono]methyl]phenyl]carbamate (1.0 eq., 0.55 g) in dichloromethane (7 mL) was added 2,2,2-trifluoroacetic acid (5.0 eq., 0.79 g) at room temperature. The reaction mixture was then stirred overnight at the same temperature. The solvent was evaporated and the resulting mixture was poured into ethyl acetate/water. Sodium hydroxide (1M) was added to the aqueous layer until pH was basic. The aqueous layer was extracted twice with ethyl acetate, the organic phase dried over sodium sulphate and the solvent evaporated. The crude reaction mixture was purified by flash chromatography, to afford the title compound as a solid.

1H NMR (400 MHz, DMSO-d6) δ ppm: 11.41 (s, 1H), 9.60 (s, 1H), 7.94 (s, 1H), 7.53 (d, 2H), 7.09 (m, 3H), 6.54 (d, 2H), 5.60 (s, 2H), 2.18 (s, 6H).

Step C-4: Preparation of 1-(2,6-dimethylphenyl)-3-[(4-hydrazinophenyl)methyleneamino]thiourea

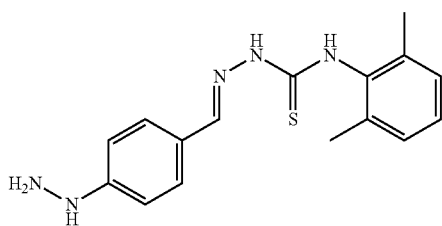 [SMILES: Cc1cccc(C)c1NC(=S)N/N=C/c1ccc(NN)cc1]

To solution of 1-[4-aminophenyl)methyleneamino]-3-(2,6-dimethylphenyl)thiourea (1.0 eq., 0.25 g) in concentrated hydrogen chloride (3.1 mL) at −10° C. was added dropwise a solution of sodium nitrite (1.3 aq., 0.07 g) in water (0.3 mL), carefully monitoring that the temperature didn't exceed 5° C. The reaction mixture was stirred for 1 h at 0° C., then cooled down to −40° C. A solution of dichlorotin dihydrate (2.6 eq., 0.49 g) in concentrated hydrogen chloride (0.5 mL) was added dropwise to the reaction mixture, which was then stirred 1 h at 0° C. The mixture was poured into dichloromethane/sodium hydroxide (2M), then sodium hydroxide was added until basic pH. The aqueous layer was extracted twice with ethyl acetate, the organic phase dried over sodium sulphate and the solvent evaporated. The crude reaction mixture was used without purification in the following step.

Step C-5: Preparation of 1-(2,6-dimethylphenyl)-3-[[4-[2-[1-[4-(trifluoromethoxy)phenyl]ethylidene]hydrazino]phenyl]methyleneamino]thiourea (compound 3)

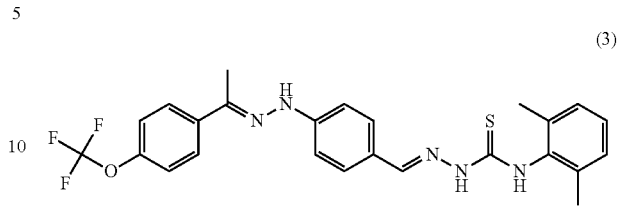

(3)

To a solution of 1-(2,6-dimethylphenyl)-3-[(4-hydrazinophenyl)methyleneamino]thiourea (1.0 eq., 90 mg) in tetrahydrofuran (2.9 mL) was added 1-[4-(trifluoromethoxy)phenyl]ethanone (1.0 eq., 58 mg) at room temperature. The reaction mixture was then stirred at room temperature overnight. The mixture was poured into dichloromethane/water, the aqueous layer was extracted twice with dichloromethane, the organic phase dried over sodium sulphate and the solvent evaporated. The crude was submitted to column chromatography to give the title compound as an amorphous solid.

1H NMR (400 MHz, DMSO-d6) δ ppm: 11.52-11.58 (m, 1H), 9.69-9.73 (m, 1H), 9.62-9.68 (m, 1H), 8.03-8.05 (m, 1H), 7.87-7.94 (m, 2H), 7.72-7.80 (m, 2H), 7.35-7.42 (m, 2H), 7.22-7.29 (m, 2H), 7.08-7.13 (m, 3H), 2.25-2.31 (m, 3H), 2.16-2.20 (m, 6H).

Lc MS Method A: Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 Waters UPLC HSS, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

LC MS Method B: Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

LC MS Method C: Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8, Temp: 60° C., DAD Wavelength range (nm): 210 to 500, Solvent Gradient: A=water+5% MeOH+0.05% HCOOH, B=Acetonitrile+ 0.05% HCOOH: gradient: gradient: 0 min 40% B, 60% A; 1.2-1.5 min 100% B; Flow (ml/min) 0.85.

TABLE Z

Examples of compounds according to any one of embodiments 1 to 22

| Example No. | Structures | Melting Point [° C.] | LC MS/ NMR | LC MS Method |
|---|---|---|---|---|
| 1 | 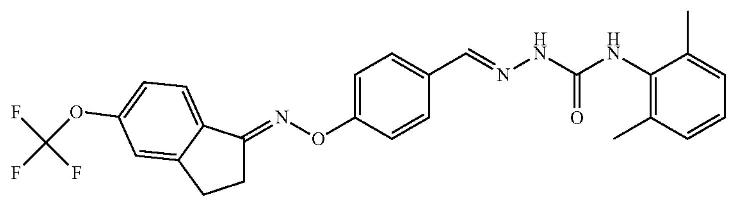 [SMILES: Cc1cccc(C)c1NC(=O)N/N=C/c1ccc(O/N=C2\CCc3cc(OC(F)(F)F)ccc32)cc1] | 174-176 | 497 (M + H)+ $R_t$ = 1.25 min | A |
| 2 | 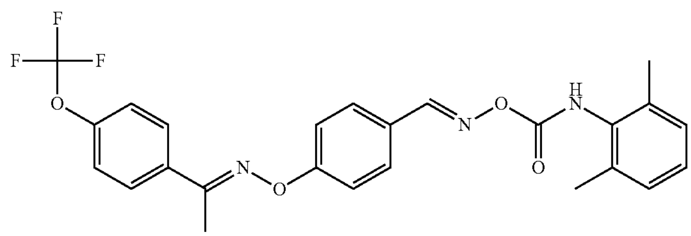 [SMILES: C/C(=N\Oc1ccc(/C=N/OC(=O)Nc2c(C)cccc2C)cc1)c1ccc(OC(F)(F)F)cc1] | 145-152 | 486 (M + H)+ $R_t$ = 1.27 min | A |
| 3 | 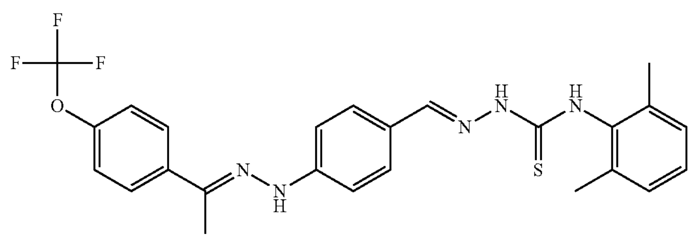 [SMILES: C/C(=N\Nc1ccc(/C=N/NC(=S)Nc2c(C)cccc2C)cc1)c1ccc(OC(F)(F)F)cc1] | — | 500 (M + H)+ $R_t$ = 1.22 min | A |
| 4 | 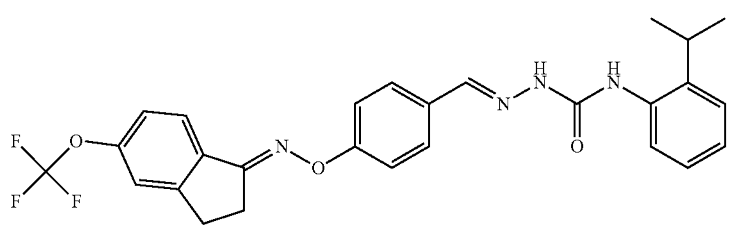 [SMILES: CC(C)c1ccccc1NC(=O)N/N=C/c1ccc(O/N=C2\CCc3cc(OC(F)(F)F)ccc32)cc1] | 170-172 | 511 (M + H)+ $R_t$ = 1.32 min | A |
| 5 | 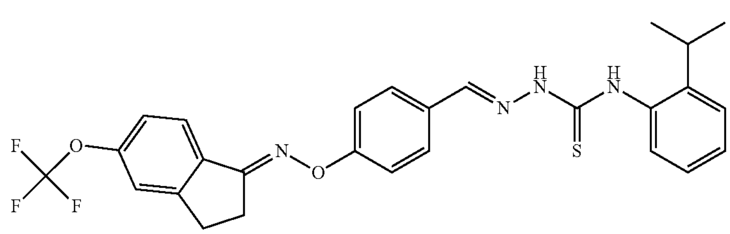 | 164-166 | 527 (M + H)+ $R_t$ = 1.32 min | A |
| 6 | 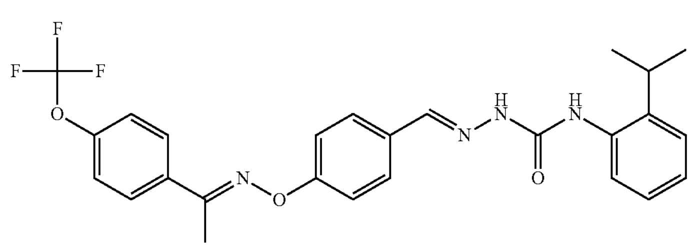 | 148-152 | 499 (M + H)+ $R_t$ = 1.30 min | A |

TABLE Z-continued
Examples of compounds according to any one of embodiments 1 to 22
| Example No. | Structures | Melting Point [° C.] | LC MS/ NMR | LC MS Method |
|---|---|---|---|---|
| 7 | 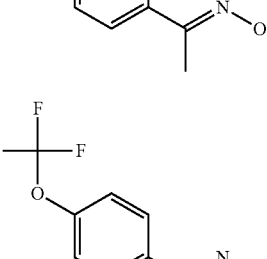 | 165-167 | 485 (M + H)+ R$_t$ = 1.23 min | A |
| 8 | 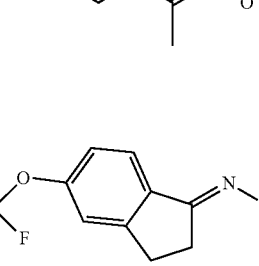 | 163-165 | 515 (M + H)+ R$_t$ = 1.31 min | A |
| 9 | 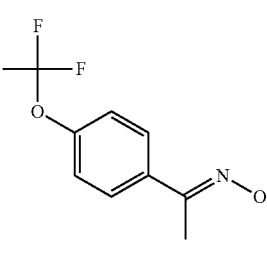 | 172-180 | 513 (M + H)+ R$_t$ = 1.28 min | A |
| 10 | 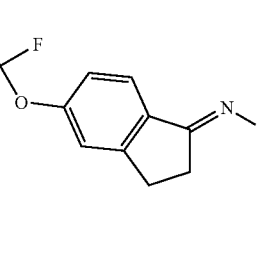 | 181-183 | 501 (M + H)+ R$_t$ = 1.27 min | A |
| 11 | 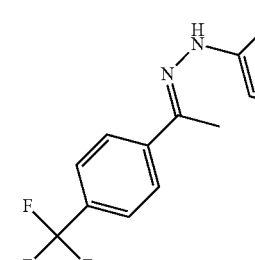 | — | 512 (M + H)+ R$_t$ = 1.23 min | A |
| 12 | 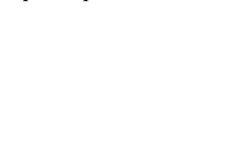 | — | 468 (M + H)+ R$_t$ = 1.21 min | A |

TABLE Z-continued

Examples of compounds according to any one of embodiments 1 to 22

| Example No. | Structures | Melting Point [° C.] | LC MS/ NMR | LC MS Method |
|---|---|---|---|---|
| 13 | 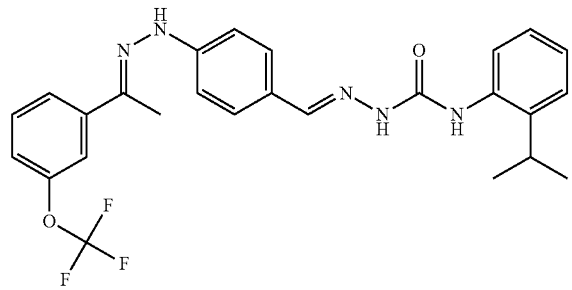 | — | 498 (M + H)+ R$_t$ = 1.29 min | A |
| 14 | 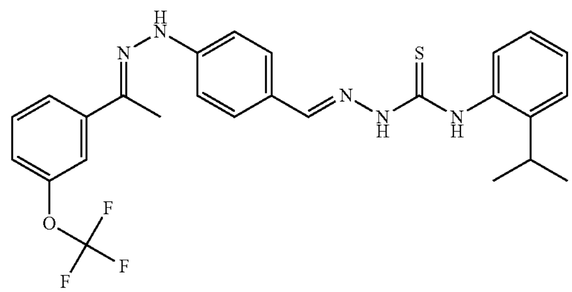 | — | 514 (M + H)+ R$_t$ = 1.31 min | A |
| 15 | 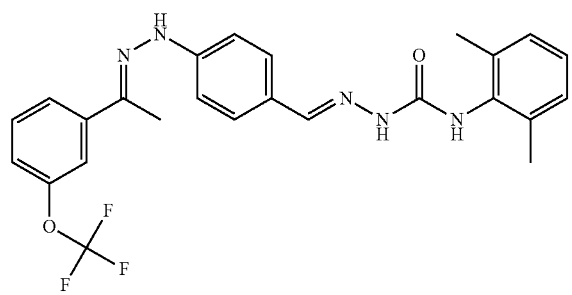 [SMILES: C/C(=N\Nc1ccc(/C=N/NC(=O)Nc2c(C)cccc2C)cc1)c1cccc(OC(F)(F)F)c1] | 215-223 | 484 (M + H)+ R$_t$ = 1.18 min | A |
| 16 | 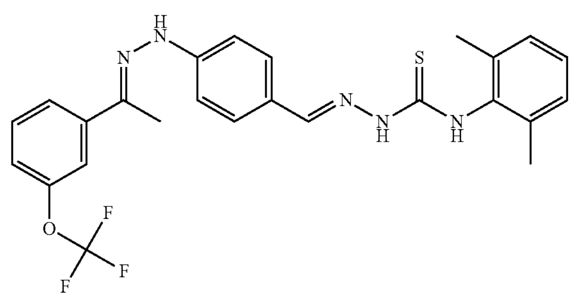 | 215-223 | 500 (M + H)+ R$_t$ = 1.22 min | A |
| 17 | 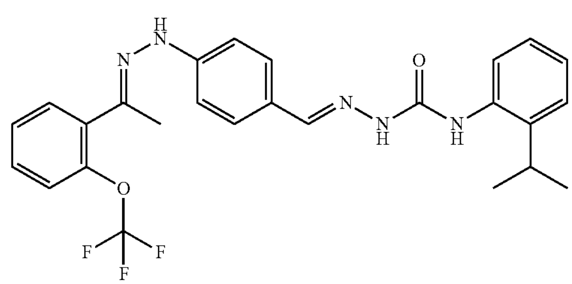 | — | 498 (M + H)+ R$_t$ = 1.23 min | A |

TABLE Z-continued

Examples of compounds according to any one of embodiments 1 to 22

| Example No. | Structures | Melting Point [° C.] | LC MS/NMR | LC MS Method |
|---|---|---|---|---|
| 18 | 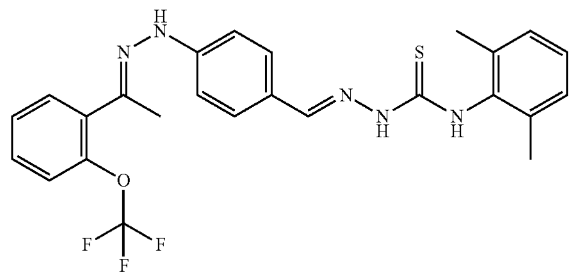 | — | 500 (M + H)+ R$_t$ = 1.20 min | A |
| 19 | 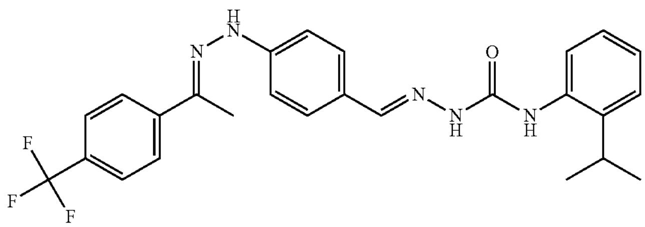 [SMILES: C/C(=N\Nc1ccc(/C=N/NC(=O)Nc2ccccc2C(C)C)cc1)c1ccc(C(F)(F)F)cc1] | 228-240 | 482 (M + H)+ R$_t$ = 1.23 min | A |
| 20 | 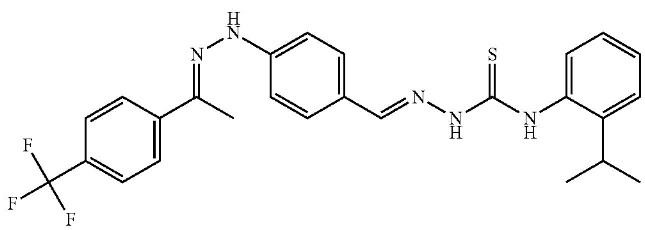 | 198-209 | 498 (M + H)+ R$_t$ = 1.25 min | A |
| 21 | 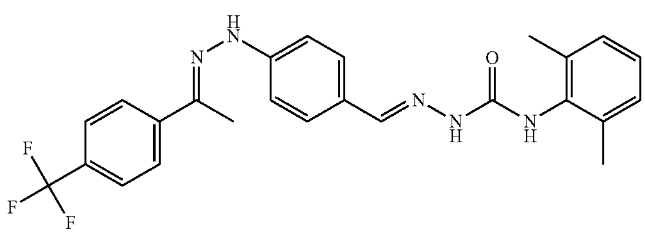 [SMILES: C/C(=N\Nc1ccc(/C=N/NC(=O)Nc2c(C)cccc2C)cc1)c1ccc(C(F)(F)F)cc1] | 215-225 | 468 (M + H)+ R$_t$ = 1.17 min | A |
| 22 | 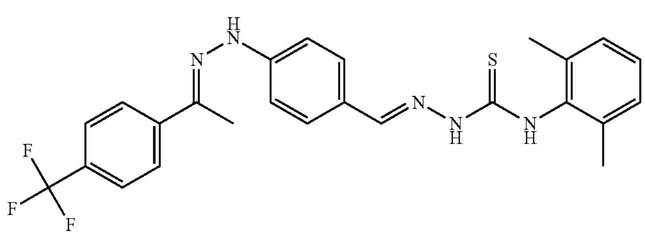 | 232-240 | 484 (M + H)+ R$_t$ = 1.21 min | A |
| 23 | 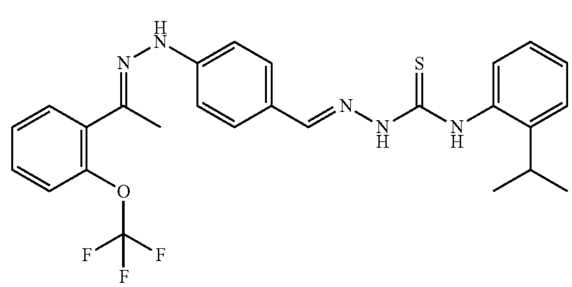 | 184-189 | 514 (M + H)+ R$_t$ = 1.29 min | A |

TABLE Z-continued

Examples of compounds according to any one of embodiments 1 to 22

| Example No. | Structures | Melting Point [° C.] | LC MS/ NMR | LC MS Method |
|---|---|---|---|---|
| 24 | 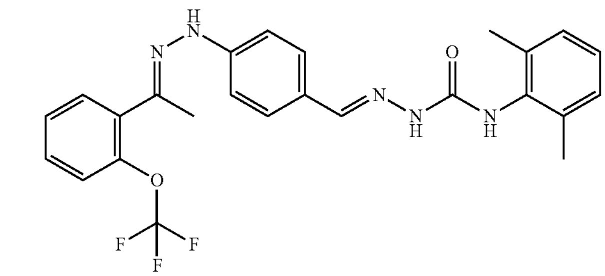 | 215-224 | 484 (M + H)+ R$_t$ = 1.16 min | A |
| 25 | 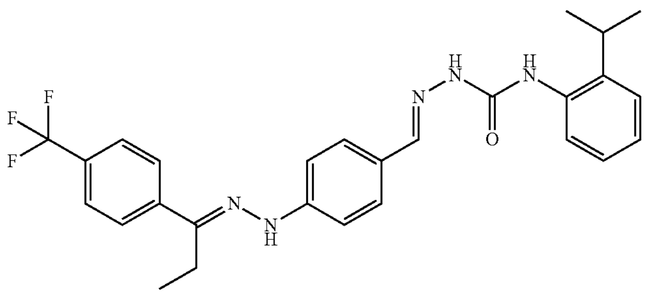 [SMILES: CC/C(=N\Nc1ccc(/C=N/NC(=O)Nc2ccccc2C(C)C)cc1)c1ccc(C(F)(F)F)cc1] | 210-222 | 496 (M + H)+ R$_t$ = 1.27 min | A |
| 26 | 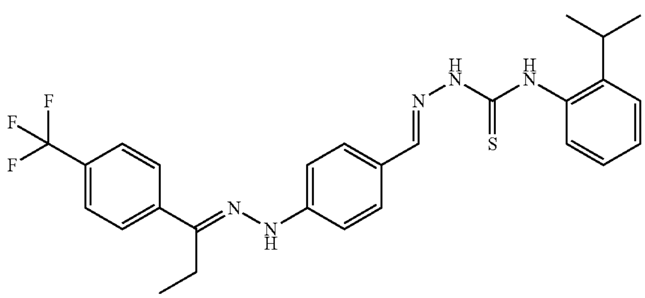 [SMILES: CC/C(=N\Nc1ccc(/C=N/NC(=S)Nc2ccccc2C(C)C)cc1)c1ccc(C(F)(F)F)cc1] | 205-210 | 512 (M + H)+ R$_t$ = 1.28 min | A |
| 27 | 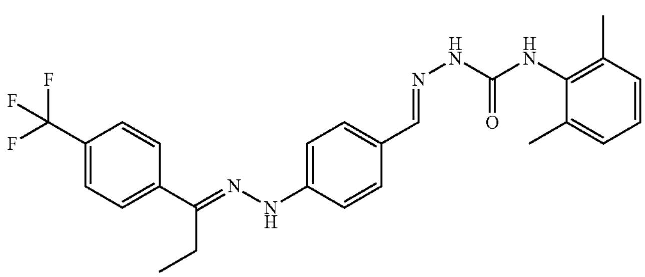 [SMILES: CC/C(=N\Nc1ccc(/C=N/NC(=O)Nc2c(C)cccc2C)cc1)c1ccc(C(F)(F)F)cc1] | 212-226 | 482 (M + H)+ R$_t$ = 1.20 min | A |
| 28 | 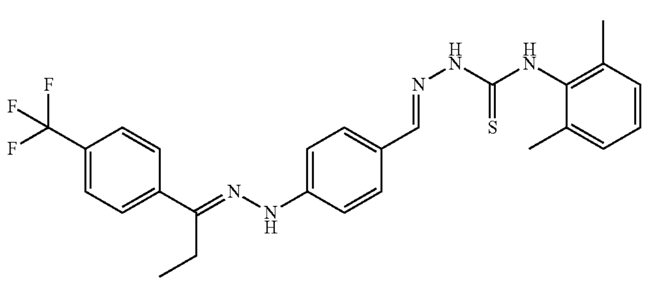 | — | 498 (M + H)+ R$_t$ = 1.24 min | A |

TABLE Z-continued

Examples of compounds according to any one of embodiments 1 to 22

| Example No. | Structures | Melting Point [° C.] | LC MS/ NMR | LC MS Method |
|---|---|---|---|---|
| 29 | 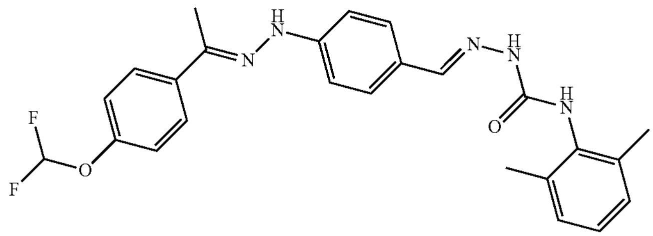 [SMILES: C/C(=N\Nc1ccc(/C=N/NC(=O)Nc2c(C)cccc2C)cc1)c1ccc(OC(F)F)cc1] | — | 466 (M + H)+ R$_t$ = 1.10 min | A |
| 30 | 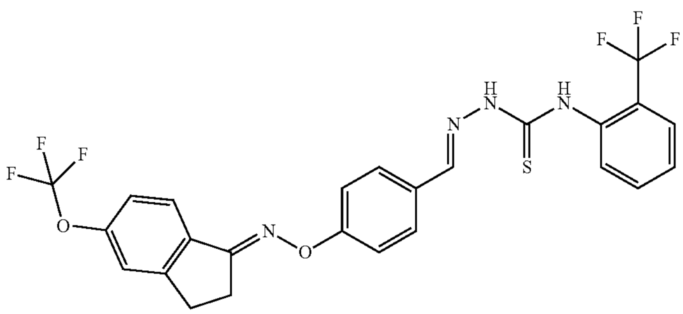 [SMILES: FC(F)(F)Oc1ccc2c(c1)CC/C2=N\Oc1ccc(/C=N/NC(=S)Nc2ccccc2C(F)(F)F)cc1] | 156-165 | 553 (M + H)+ R$_t$ = 1.31 min | A |
| 31 | 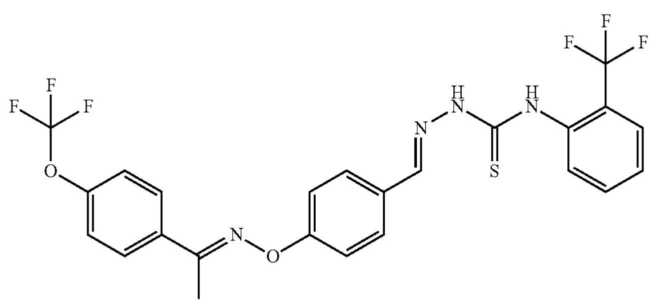 [SMILES: C/C(=N\Oc1ccc(/C=N/NC(=S)Nc2ccccc2C(F)(F)F)cc1)c1ccc(OC(F)(F)F)cc1] | 166-170 | 541 (M + H)+ R$_t$ = 1.29 min | A |

Biological Examples (%=Percent by Weight, Unless Otherwise Specified)

Example B1:

*Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying, the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample.

The following compounds resulted in at least 80% control at an application rate of 200 ppm: 1, 2, 3, 4, 5, 7, 9, 10, 11, 20, 21, 22, 26, 27, 28 and 29.

Example B2:

*Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: 1, 2, 3, 4, 5, 6, 7, 8, 9, 10, 11, 14, 15, 16, 18, 19, 20, 21, 22, 23, 25, 26, 27, 28 and 29.

Example B3:

*Diabrotica balteata* (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: 1, 2, 3, 4, 5, 6, 7, 8, 9, 10, 11, 12, 13, 14, 16, 19, 20, 21, 22, 25, 26, 27, 28, 30 and 31.

The invention claimed is:
1. A compound of formula (I)

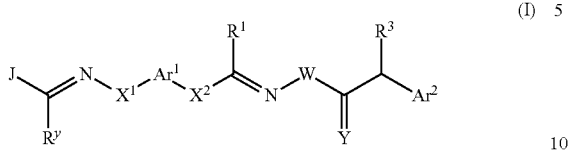
(I)

wherein
Ar¹ is phenyl which is unsubstituted or substituted by one to three substituents independently selected from $C_1$-$C_6$alkyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_6$alkoxy and $C_1$-$C_6$haloalkoxy;
Ar² is phenyl which is unsubstituted or substituted by one to three substituents independently selected from $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, $C_1$-$C_6$alkoxy, $C_1$-$C_6$haloalkoxy and —S—$C_1$-$C_6$alkyl;
$X^1$ is O or $NR^6$;
$X^2$ is a bond, —$CH_2$— or —$CH_2CH_2$—;
W is O or $NR^2$;
Y is oxygen or sulfur;
$R^1$ is hydrogen or $C_1$-$C_6$alkyl;
$R^2$ is selected from hydrogen, $C_1$-$C_6$alkyl and $C_1$-$C_6$haloalkyl;
$R^3$ is selected from hydrogen, $C_1$-$C_6$alkyl and $C_1$-$C_6$haloalkyl;
$R^6$ is hydrogen or $C_1$-$C_6$alkyl;
J is a group selected from $J^{1'}$, $J^{2'}$, $J^{3'}$, $J^9$ and $J^{11}$:

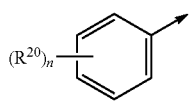
$J^{1'}$

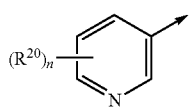
$J^{2'}$

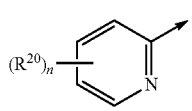
$J^{3'}$

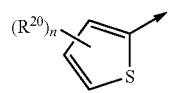
$J^9$

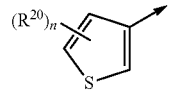
$J^{11}$ wherein n is 0, 1 or 2, and $R^{20}$ is independently selected from hydrogen, $C_3$-$C_6$halocycloalkyl and $C_1$-$C_6$haloalkoxy;
$R^Y$ is $C_1$-$C_6$alkyl; or
J and $R^Y$ together with the carbon atom to which they are attached form a bicyclic ring of formula

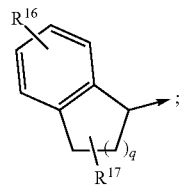

q is 1 or 2;
$R^{16}$ and $R^{17}$ are independently selected from hydrogen, $C_3$-$C_6$halocycloalkyl and $C_1$-$C_6$haloalkoxy;
or an agrochemically acceptable salt, stereoisomer, tautomer, N-oxide thereof.

2. A compound according to claim 1, of formula (Ia)

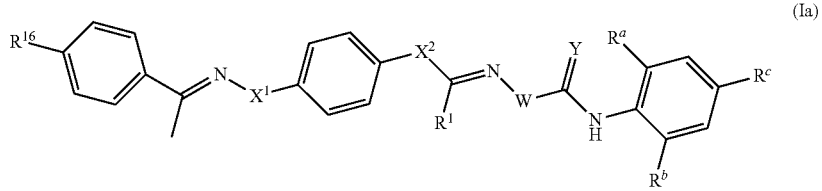
(Ia)

or formula (Ib)

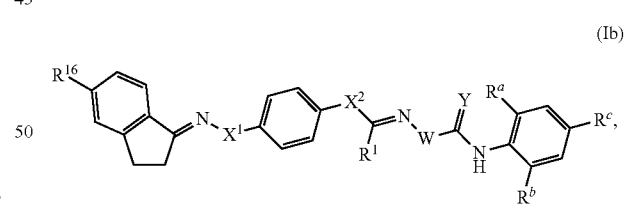
(Ib)

wherein
$R^a$, $R^b$ and $R^c$ are independently selected from hydrogen, $C_1$-$C_6$alkyl, $C_1$-$C_6$haloalkyl, halogen, $C_1$-$C_6$alkoxy and $C_1$-$C_6$haloalkoxy;
$X^1$ is O or $NR^6$;
$X^2$ is a bond, —$CH_2$—or —$CH_2CH_2$—;
W is O or $NR^2$;
Y is oxygen or sulfur;
$R^1$ is hydrogen or methyl;
$R^2$ is hydrogen or $C_1$-$C_6$alkyl;
$R^6$ is hydrogen or $C_1$-$C_6$alkyl;
$R^{16}$ is $C_1$-$C_6$haloalkoxy;
or an agrochemically acceptable salt, stereoisomer, tautomer, N-oxide thereof.

3. A compound according to claim 1, of formula (Ia)

(Ia)

wherein
$R^a$ is $R^b$ and $R^c$ are independently selected from hydrogen, methyl, isopropyl, trifluoromethyl, chloro, fluoro, methoxy and —OCF$_3$;
$X^1$ is selected from O, NH and NCH$_3$;
$X^2$ is a bond;
W is selected from O, NH and NCH$_3$;
Y is oxygen or sulfur;
$R^1$ is hydrogen or methyl;
$R^{16}$ is —OCF$_3$ or —OCF$_2$CF$_3$;
or an agrochemically acceptable salt, stereoisomer, tautomer, N-oxide thereof.

4. A compound according to claim 1, of formula (Ib)

(Ib)

wherein
$R^a$, $R^b$ and $R^c$ are independently selected from hydrogen, $C_1$-$C_6$alkyl, $C_1$-$C_6$haloalkyl, halogen, $C_1$-$C_6$alkoxy and $C_1$-$C_6$haloalkoxy;
$X^1$ is O or NR$^6$;
$X^2$ is a bond, —CH$_2$— or —CH$_2$CH$_2$—;
W is O or NR$^2$;
Y is oxygen or sulfur;
$R^1$ is hydrogen or methyl;
$R^2$ is hydrogen or $C_1$-$C_6$alkyl;
$R^6$ is hydrogen or $C_1$-$C_6$alkyl;
$R^{16}$ is $C_1$-$C_6$haloalkoxy;
or an agrochemically acceptable salt, stereoisomer, tautomer, N-oxide thereof.

5. A compound according to claim 1, of formula (Ib)

(Ib)

wherein $R^a$ is $R^b$ and $R^c$ are independently selected from hydrogen, methyl, isopropyl, trifluoromethyl, chloro, fluoro, methoxy and —OCF$_3$;
$X^1$ is selected from O, NH and NCH$_3$;
$X^2$ is a bond;
W is selected from O, NH and NCH$_3$;
Y is oxygen or sulfur;
$R^1$ is hydrogen or methyl;
$R^{16}$ is —OCF$_3$ or —OCF$_2$CF$_3$;
or an agrochemically acceptable salt, stereoisomer, tautomer, N-oxide thereof.

6. A compound selected from

| Example No. | Structures | IUPAC Name |
|---|---|---|
| 1 | 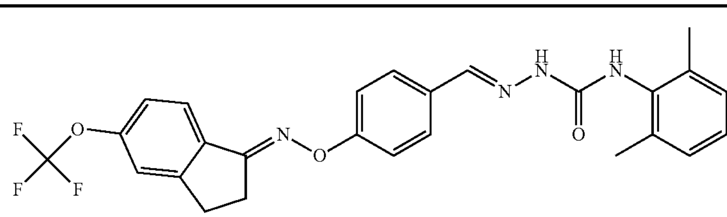 | 1-(2,6-dimethylphenyl)-3-[[4-[[5-(trifluoromethoxy)indan-1-ylidene]amino]oxyphenyl]methyleneamino]urea |
| 2 | 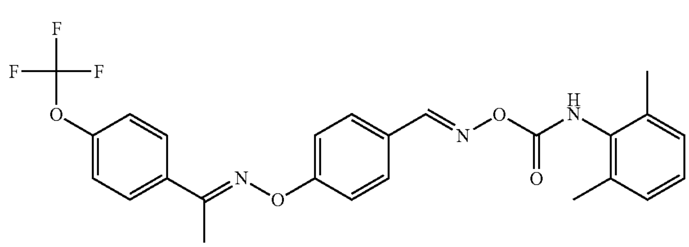 [SMILES: C/C(=N\Oc1ccc(/C=N/OC(=O)Nc2c(C)cccc2C)cc1)c1ccc(OC(F)(F)F)cc1] | [[4-[1-[4-(trifluoromethoxy)phenyl]ethylideneamino]oxyphenyl]methyleneamino]N-(2,6-dimethylphenyl)carbamate |

-continued

| Example No. | Structures | IUPAC Name |
|---|---|---|
| 3 | 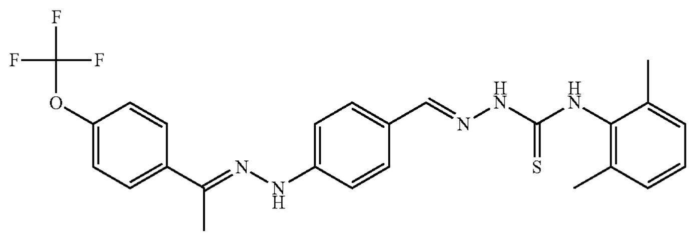 [SMILES: C/C(=N\Nc1ccc(/C=N/NC(=S)Nc2c(C)cccc2C)cc1)c1ccc(OC(F)(F)F)cc1] | 1-(2,6-dimethylphenyl)-3-[[4-[2-[1-[4-(trifluoromethoxy)phenyl]ethylidene]hydrazino]phenyl]methyleneamino]thiourea |
| 4 | 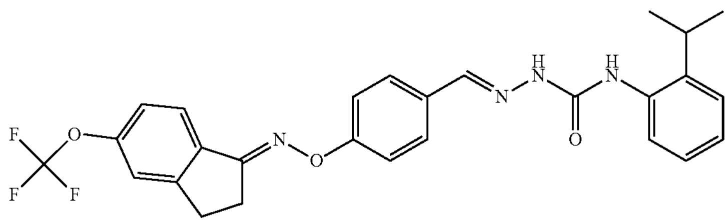 [SMILES: CC(C)c1ccccc1NC(=O)N/N=C/c1ccc(O/N=C2\CCc3cc(OC(F)(F)F)ccc32)cc1] | 1-(2-isopropylphenyl)-3-[[4-[[5-(trifluoromethoxy)indan-1-ylidene]amino]oxyphenyl]methyleneamino]urea |
| 5 | 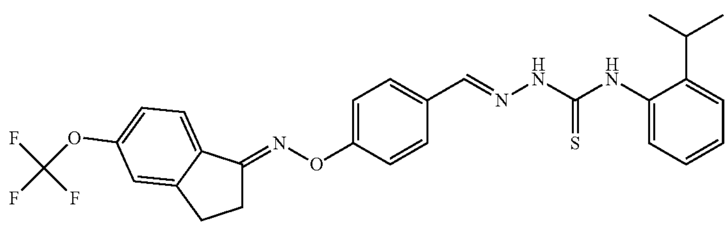 [SMILES: CC(C)c1ccccc1NC(=S)N/N=C/c1ccc(O/N=C2\CCc3cc(OC(F)(F)F)ccc32)cc1] | 1-(2-isopropylphenyl)-3-[[4-[[5-(trifluoromethoxy)indan-1-ylidene]amino]oxyphenyl]methyleneamino]thiourea |
| 6 | 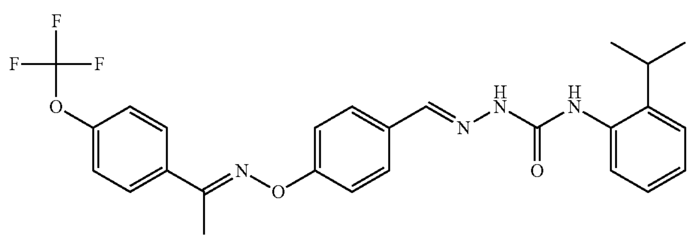 [SMILES: C/C(=N\Oc1ccc(/C=N/NC(=O)Nc2ccccc2C(C)C)cc1)c1ccc(OC(F)(F)F)cc1] | 1-(2-isopropylphenyl)-3-[[4-[1-[4-(trifluoromethoxy)phenyl]ethylidene-amino]oxyphenyl]methyleneamino]urea |
| 7 | 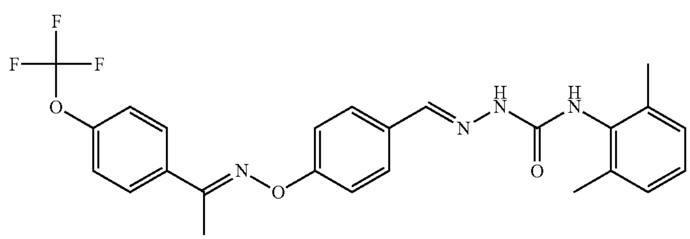 [SMILES: C/C(=N\Oc1ccc(/C=N/NC(=O)Nc2c(C)cccc2C)cc1)c1ccc(OC(F)(F)F)cc1] | 1-(2,6-dimethylphenyl)-3-[[4-[1-[4-(trifluoromethoxy)phenyl]ethylidene-amino]oxyphenyl]methyleneamino]urea |
| 8 | 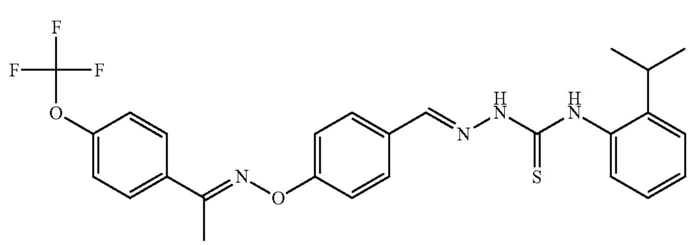 [SMILES: C/C(=N\Oc1ccc(/C=N/NC(=S)Nc2ccccc2C(C)C)cc1)c1ccc(OC(F)(F)F)cc1] | 1-(2-isopropylphenyl)-3-[[4-[1-[4-(trifluoromethoxy)phenyl]ethylidene-amino]oxyphenyl]methyleneamino]thiourea |

| Example No. | Structures | IUPAC Name |
|---|---|---|
| 9 | 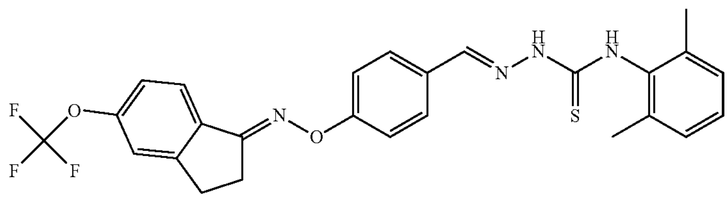 [SMILES: Cc1cccc(C)c1NC(=S)N/N=C/c1ccc(O/N=C2\CCc3cc(OC(F)(F)F)ccc32)cc1] | 1-(2,6-dimethylphenyl)-3-[[4-[[5-(trifluoromethoxy)indan-1-ylidene]amino]oxyphenyl]methyleneamino]thiourea |
| 10 | 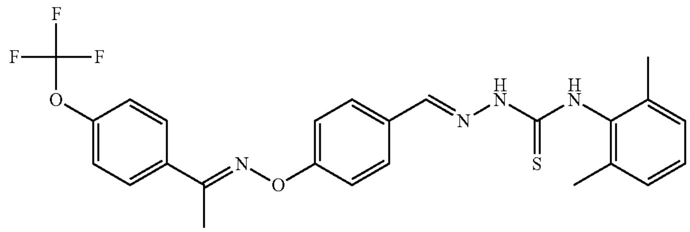 [SMILES: C/C(=N\Oc1ccc(/C=N/NC(=S)Nc2c(C)cccc2C)cc1)c1ccc(OC(F)(F)F)cc1] | 1-(2,6-dimethylphenyl)-3-[[4-[1-[4-(trifluoromethoxy)phenyl]ethylideneamino]oxyphenyl]methyleneamino]thiourea |
| 11 | 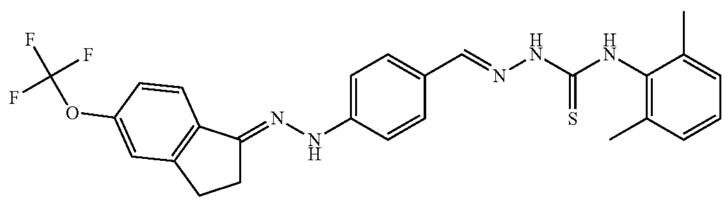 [SMILES: Cc1cccc(C)c1NC(=S)N/N=C/c1ccc(N/N=C2\CCc3cc(OC(F)(F)F)ccc32)cc1] | 1-(2,6-dimethylphenyl)-3-[[4-[2-[5-(trifluoromethoxy)indan-1-ylidene]hydrazino]phenyl]methyleneamino]thiourea |
| 12 | 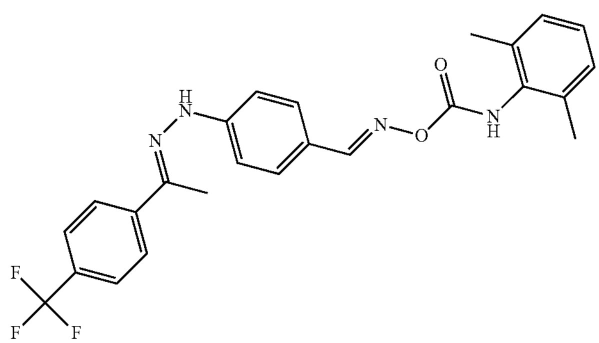 [SMILES: C/C(=N\Nc1ccc(/C=N/OC(=O)Nc2c(C)cccc2C)cc1)c1ccc(C(F)(F)F)cc1] | [[4-[2-[1-[4-(trifluoromethyl)phenyl]ethylidene]hydrazino]phenyl]methyleneamino] N-(2,6-dimethylphenyl)carbamate |
| 13 | 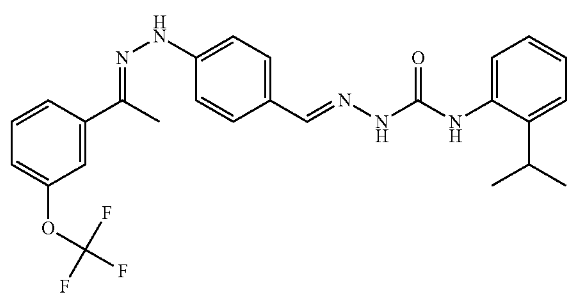 | 1-(2-isopropylphenyl)-3-[[4-[2-[1-[3-(trifluoromethoxy)phenyl]ethylidene]hydrazino]phenyl]methyleneamino]urea |
| 14 | 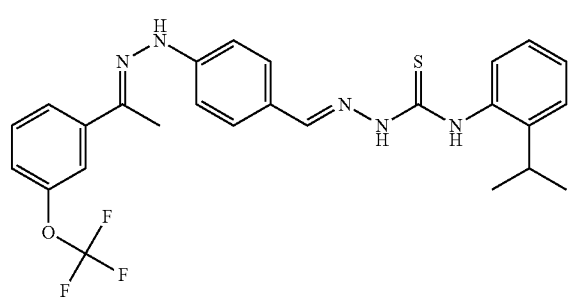 | 1-(2-isopropylphenyl)-3-[[4-[2-[1-[3-(trifluoromethoxy)phenyl]ethylidene]hydrazino]phenyl]methyleneamino]thiourea |

-continued

| Example No. | Structures | IUPAC Name |
|---|---|---|
| 15 | 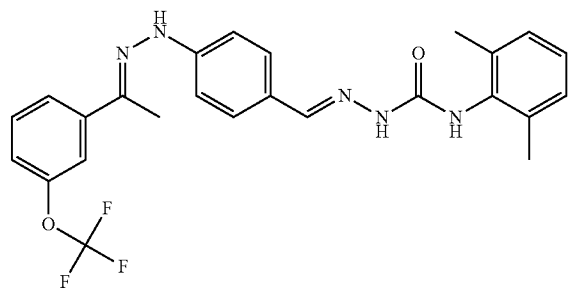 | 1-(2,6-dimethylphenyl)-3-[[4-[2-[1-[3-(trifluoromethoxy)phenyl]ethylidene]hydrazino]phenyl]methyleneamino]urea |
| 16 | 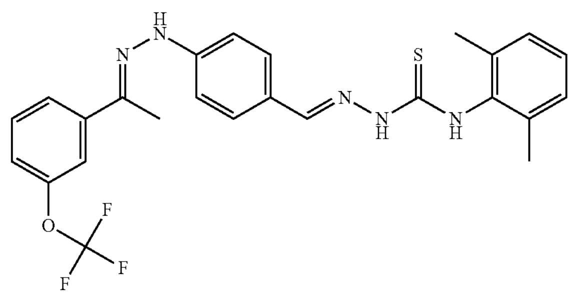 | 1-(2,6-dimethylphenyl)-3-[[4-[2-[1-[3-(trifluoromethoxy)phenyl]ethylidene]hydrazino]phenyl]methyleneamino]thiourea |
| 17 | 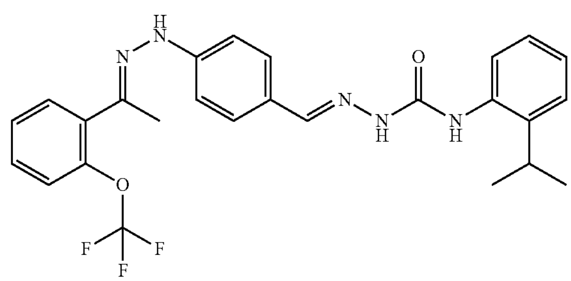 [SMILES: C/C(=N\Nc1ccc(/C=N/NC(=O)Nc2ccccc2C(C)C)cc1)c1ccccc1OC(F)(F)F] | 1-(2-isopropylphenyl)-3-[[4-[2-[1-[2-(trifluoromethoxy)phenyl]ethylidene]hydrazino]phenyl]methyleneamino]urea |
| 18 | 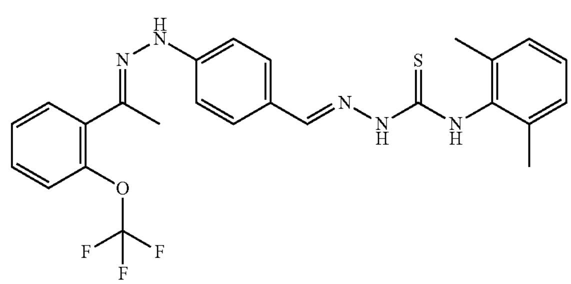 | 1-(2,6-dimethylphenyl)-3-[[4-[2-[1-[2-(trifluoromethoxy)phenyl]ethylidene]hydrazino]phenyl]methyleneamino]thiourea |
| 19 | 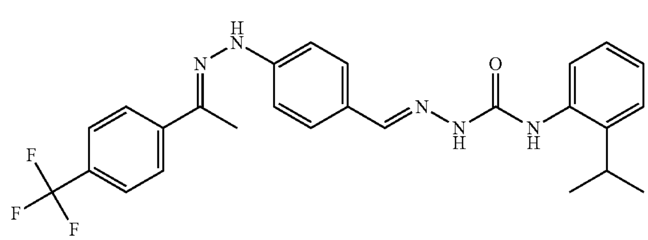 [SMILES: C/C(=N\Nc1ccc(/C=N/NC(=O)Nc2ccccc2C(C)C)cc1)c1ccc(C(F)(F)F)cc1] | 1-(2-isopropylphenyl)-3-[(E)-[4-[(2E)-2-[1-[4-(trifluoromethyl)phenyl]ethylidene]hydrazino]phenyl]methyleneamino]urea |

-continued

| Example No. | Structures | IUPAC Name |
|---|---|---|
| 20 | 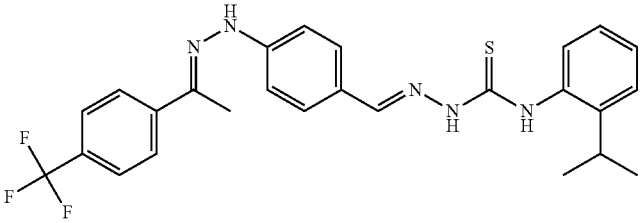 | 1-(2-isopropylphenyl)-3-[(E)-[4-[(2E)-2-[1-[4-(trifluoromethyl)phenyl]ethylidene]hydrazino]phenyl]methyleneamino]thiourea |
| 21 | 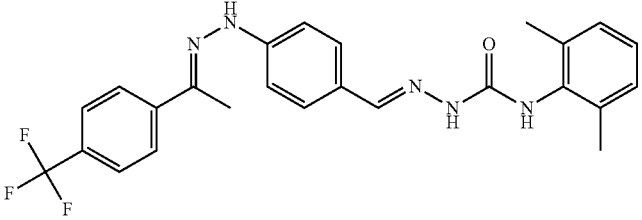 [SMILES: C/C(=N\Nc1ccc(/C=N/NC(=O)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]ethylidene]hydrazino]phenyl]methyleneamino]urea |
| 22 | 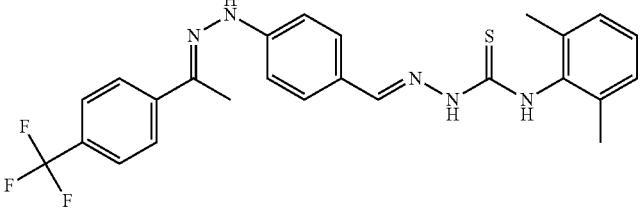 | 1-(2,6-dimethylphenyl)-3-[(E)-[4-[(2E)-2-[1-[4-(trifluoromethyl)phenyl]ethylidene]hydrazino]phenyl]methyleneamino]thiourea |
| 23 | 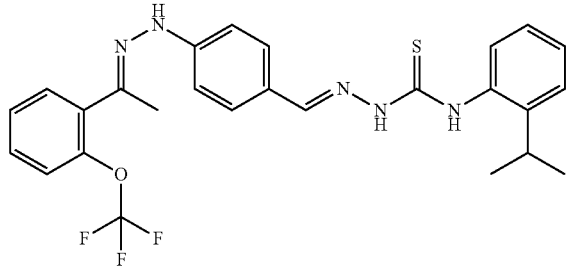 | 1-(2-isopropylphenyl)-3-[(E)-[4-[(2E)-2-[1-[2-(trifluoromethoxy)phenyl]ethylidene]hydrazino]phenyl]methylene-amino]thiourea |
| 24 | 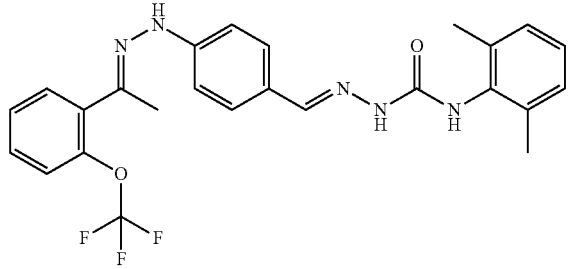 | 1-(2,6-dimethylphenyl)-3-[(E)-[4-[(2E)-2-[1-[2-(trifluoromethoxy)phenyl]ethylidene]hydrazino]phenyl]methylene-amino]urea |
| 25 | 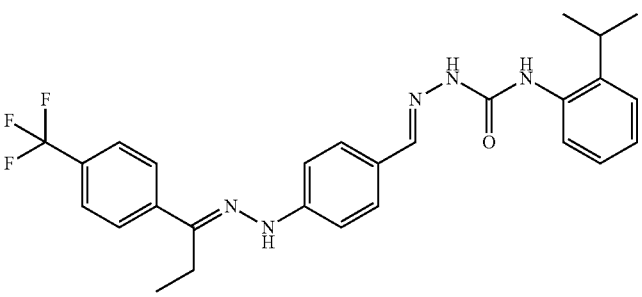 [SMILES: CC/C(=N\Nc1ccc(/C=N/NC(=O)Nc2ccccc2C(C)C)cc1)c1ccc(C(F)(F)F)cc1] | 1-(2-isopropylphenyl)-3-[(E)-[4-[(2E)-2-[1-[4-(trifluoromethyl)phenyl]propylidene]hydrazino]phenyl]methyleneamino]urea |

| Example No. | Structures | IUPAC Name |
|---|---|---|
| 26 | 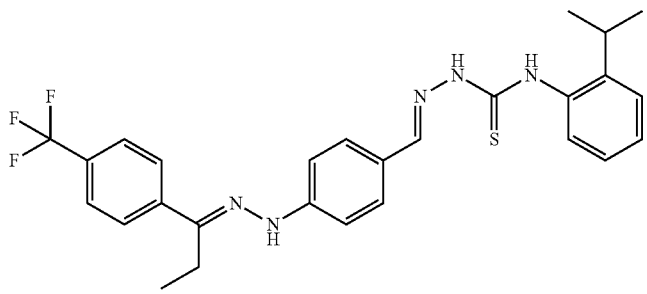 | 1-(2-isopropylphenyl)-3-[(E)-[4-[(2E)-2-[1-[4-(trifluoromethyl)phenyl]propylidene]hydrazino]phenyl]methyleneamino]thiourea |
| 27 | 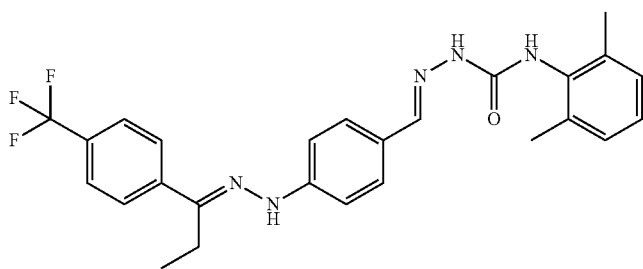 [SMILES: CC/C(=N\Nc1ccc(/C=N/NC(=O)Nc2c(C)cccc2C)cc1)c1ccc(C(F)(F)F)cc1] | 1-(2,6-dimethylphenyl)-3-[(E)-[4-[(2E)-2-[1-[4-(trifluoromethyl)phenyl]propylidene]hydrazino]phenyl]methyleneamino]urea |
| 28 | 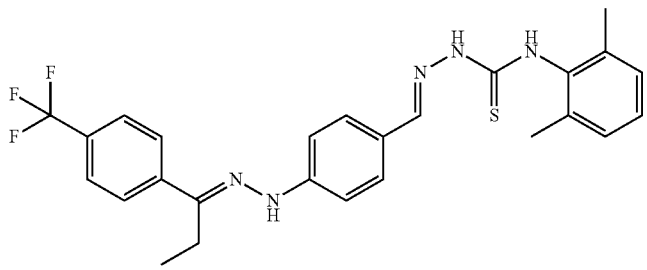 | 1-(2,6-dimethylphenyl)-3-[(E)-[4-[(2E)-2-[1-[4-(trifluoromethyl)phenyl]propylidene]hydrazino]phenyl]methyleneamino]thiourea |
| 29 | 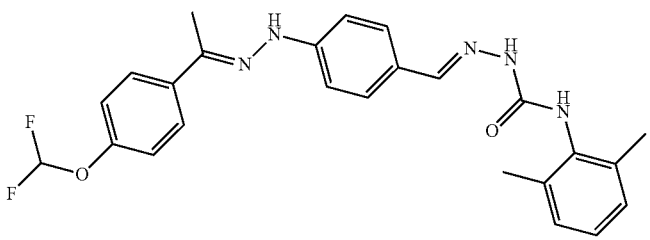 | 1-[[4-[2-[1-[4-(difluoromethoxy)phenyl]ethylidene]hydrazino]phenyl]methyleneamino]-3-(2,6-dimethylphenyl)urea |
| 30 | 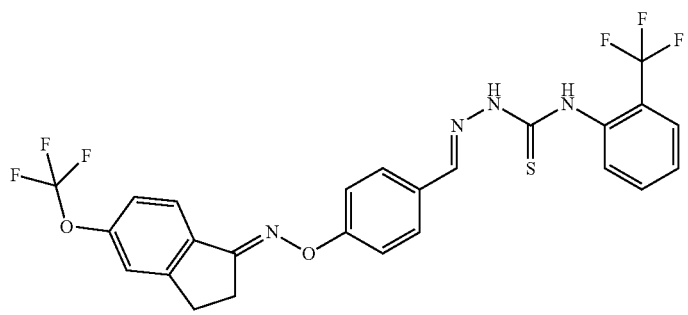 [SMILES: FC(F)(F)Oc1ccc2c(c1)CC/C2=N\Oc1ccc(/C=N/NC(=S)Nc2ccccc2C(F)(F)F)cc1] | 1-[[4-[[5-(trifluoromethoxy)indan-1-ylidene]amino]oxyphenyl]methylene-amino]-3-[2-(trifluoromethyl)phenyl]thiourea |

| Example No. | Structures | IUPAC Name |
|---|---|---|
| 31 | 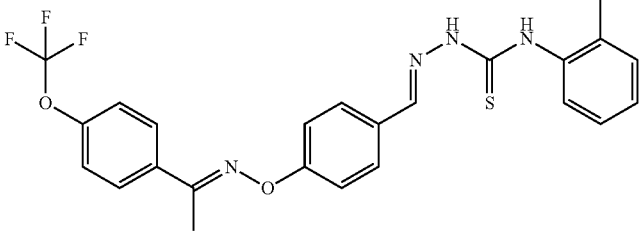 | 1-[[4-[1-[4-(trifluoromethoxy)phenyl]ethylidene-amino]oxyphenyl]methylene-amino]-3-[2-(trifluoromethyl)phenyl]thiourea | or an agrochemically acceptable salt, stereoisomer, tautomer, N-oxide thereof.

7. A pesticidal composition, which comprises at least one compound according to claim 1, or an agrochemically acceptable salt, stereoisomer, tautomer, N-oxide thereof, as active ingredient and at least one auxiliary.

8. The composition according to claim 7, which further comprises one or more other insecticidally, acaricidally, nematicidally and/or fungicidally active agents.

9. A method for controlling pests, which comprises applying a composition according to claim 7 to the pests or their environment with the exception of a method for treatment of the human or animal body by surgery or therapy and diagnostic methods practiced on the human or animal body.

10. A method for the protection of plant propagation material from the attack by pests, which comprises treating the propagation material or the site, where the propagation material is planted, with a composition according to claim 7.

11. A coated plant propagation material, wherein the coating of the plant propagation material comprises a compound as defined in claim 1.

* * * * *